(12) United States Patent
Shim et al.

(10) Patent No.: US 8,008,312 B2
(45) Date of Patent: Aug. 30, 2011

(54) CXCR4 ANTAGONISTS FOR THE TREATMENT OF HIV INFECTION

(75) Inventors: Hyunsuk Shim, Atlanta, GA (US);
Dennis C. Liotta, Atlanta, GA (US);
James P. Snyder, Atlanta, GA (US);
Weiqiang Zhan, Decatur, GA (US);
Zhongxing Liang, Tucker, GA (US)

(73) Assignee: Emory University, Atlanta, GA (US)

( * ) Notice: Subject to any disclaimer, the term of this patent is extended or adjusted under 35 U.S.C. 154(b) by 1089 days.

(21) Appl. No.: 11/329,301

(22) Filed: Jan. 9, 2006

(65) Prior Publication Data
US 2006/0264451 A1 Nov. 23, 2006

Related U.S. Application Data

(60) Provisional application No. 60/642,375, filed on Jan. 7, 2005, provisional application No. 60/642,374, filed on Jan. 7, 2005, provisional application No. 60/682,655, filed on May 18, 2005.

(51) Int. Cl.
*A01N 43/54* (2006.01)
*A61K 31/505* (2006.01)
*C07D 239/02* (2006.01)
*C07D 401/00* (2006.01)
*C07D 403/00* (2006.01)
*C07D 405/00* (2006.01)
*C07D 487/00* (2006.01)

(52) U.S. Cl. ........ 514/275; 544/330; 544/331; 544/332; 544/242; 543/263; 514/332

(58) Field of Classification Search .................. 514/275; 544/330, 331, 332, 242; 543/263
See application file for complete search history.

(56) References Cited

U.S. PATENT DOCUMENTS

| | | | |
|---|---|---|---|
| 5,874,438 A | 2/1999 | Schohe-Loop et al. | |
| 5,993,817 A | 11/1999 | Yoneda et al. | |
| 6,344,545 B1 | 2/2002 | Allaway et al. | |
| 6,358,915 B1 | 3/2002 | Patierno et al. | |
| 6,420,354 B1 | 7/2002 | Marquess et al. | |
| 6,429,308 B1 | 8/2002 | Iijima et al. | |
| 6,433,149 B1 | 8/2002 | Blaschuk et al. | |
| 6,475,488 B1 | 11/2002 | Pasqualini et al. | |
| 6,534,626 B1 | 3/2003 | Oravecz et al. | |
| 6,750,348 B1 * | 6/2004 | Bridger et al. | 546/139 |
| 2004/0132642 A1 | 7/2004 | Hwang | |
| 2004/0254221 A1 | 12/2004 | Yamamazi et al. | |
| 2007/0054930 A1 | 3/2007 | Shim et al. | |
| 2008/0227799 A1 | 9/2008 | Liotta et al. | |
| 2009/0099194 A1 | 4/2009 | Liotta et al. | |

FOREIGN PATENT DOCUMENTS

| | | |
|---|---|---|
| EP | 515684 | 12/1992 |
| WO | WO 91/11994 | 8/1991 |
| WO | WO 97/00956 A1 | 1/1997 |
| WO | WO 99/47158 A2 | 9/1999 |
| WO | 99-63984 A1 | 12/1999 |
| WO | WO 00/56729 A1 | 9/2000 |
| WO | WO 01/38352 A2 | 5/2001 |
| WO | WO 01/56591 A1 | 8/2001 |
| WO | 01-70727 A1 | 9/2001 |
| WO | WO 01/85196 A2 | 11/2001 |
| WO | 02-02516 A3 | 1/2002 |
| WO | WO 02/02516 | 1/2002 |
| WO | WO 02/094261 A1 | 11/2002 |
| WO | WO 03/029218 A1 | 4/2003 |
| WO | WO 2004/020462 A1 | 3/2004 |
| WO | WO 2004/024178 A1 | 3/2004 |
| WO | WO 2004/093817 A2 | 4/2004 |
| WO | WO 2004/059285 A2 | 7/2004 |
| WO | WO 2004/087068 A2 | 10/2004 |
| WO | WO 2004/091518 A2 | 10/2004 |
| WO | WO 2004/106493 A2 | 12/2004 |
| WO | 2005-049607 A1 | 6/2005 |
| WO | WO 2005/049607 | 6/2005 |
| WO | 2005-085189 A2 | 9/2005 |

OTHER PUBLICATIONS

STIC_search_Apr. 2009.*
Wolff, Manfred E., Burgers Medicinal Chemistry and Drug Discovery, Fifth Ed., vol. 1: Principles and Practice, John Wiley & Sons, 1995, 975.*
Banker, Gilbert S. et al., Modem Pharmaceutics, Marcel Dekker, New York, 1996.*
Reyes et al. (Tetrahedron (2002), 58(42), 8573-8579).*
Abdel-Magid, A.F., et al., "Reductive Amination of Aldehydes and Ketones with Sodium Triace-toxyborohydride. Studies on Direct and Indirect Reductive Amination Procedures(1)," *J. Org. Chem.* 61(11):3849-3862 (May 31, 1996).
Abi-Younes, S., et al., "The stromal cell-derived factor-1 chemokine is a potent platelet agonist highly expressed in atherosclerotic plaques," *Circ. Res.*, 86(2), 131-138 (Feb. 4, 2000)).
Alkhatib, G., et al., "CC CKR5: a RANTES, MIP-1alpha, MIP-1beta receptor as a fusion cofactor for macrophage-tropic HIV-1," *Science*, 272(5270):1955-1958 (Jun. 28, 1996).
Blades, M.C., et al., "Stromal cell-derived factor 1 (CXCL12) induces human cell migration into human lymph nodes transplanted into SCID mice," *J. Immunol.* 168(9):4308-4317 (May 1, 2002).
Bleul, C.C., et al., "The lymphocyte chemoattractant SDF-1 is a ligand for LESTR/fusin and blocks HIV-1 entry," *Nature*, 382(6594):829-833 (Aug. 29, 1996).
Braun, C.E., et al., "Guanidine structure and hypoglycemia: some carbocyclic diguanidines," *J. Org. Chem.*, 3(2):146-152 (1938).
Bressler, N.M., and Bressler, S.B., "Preventative ophthalmology. Age-related macular degeneration," *Ophthalmology*, 102(8):1206-1211 (Aug. 1995).
Butcher, E.C., et al. "Lymphocyte trafficking and regional immunity," *Adv. Immunol.*, 72:209-253 (1999).

(Continued)

Primary Examiner — Sreeni Padmanabhan
Assistant Examiner — Umamaheswari Ramachandran
(74) *Attorney, Agent, or Firm* — James C. Mason; Emory Patent Group

(57) ABSTRACT

The invention provides compounds, pharmaceutical compositions and methods of use of certain compounds that are antagonists of the chemokine CXCR4 receptor, and in particular to inhibit viral entry of certain viruses. Certain compounds in particular can reduce entry of immunodeficiency virus (HIV) into a cell while not reducing the capacity of stem cells to proliferate, and therefore can be useful for long term treatment regimes. The compounds are useful in particular in the treatment or prevention of HIV infections.

3 Claims, 6 Drawing Sheets

OTHER PUBLICATIONS

Campbell, J.J., and Butcher, E.C., "Chemokines in tissue-specific and microenvironment-specific lymphocyte homing," *Curr. Opin. Immunol.*, 12(3):336-341 (Jun. 2000).

Chen, W.J., et al. "Recombinant human CXC-chemokine receptor-4 in melanophores are linked to Gi protein: seven transmembrane coreceptors for human immunodeficiency virus entry into cells," *Mol. Pharmacol.*, 53(2):177-181 (Feb. 1998).

Connor, R.I., et al., "Change in coreceptor use correlates with disease progression in HIV-1-infected individuals," *J. Exp. Med.*, 185(4):621-628 (Feb. 17, 1997).

Crane, I.J., et al., "CXCR4 receptor expression on human retinal pigment epithelial cells from the blood-retina barrier leads to chemokine secretion and migration in response to stromal cell-derived factor 1 alpha," *J. Immunol.*, 165(8):4372-4378 (Oct. 15, 2000).

Davis, C.B., et al. "Signal transduction due to HIV-1 envelope interactions with chemokine receptors CXCR4 or CCR5," *J. Exp. Med.*, 186(10):1793-1798 (Nov. 17, 1997).

Deng, H.K., et al., "Expression cloning of new receptors used by simian and human immunodeficiency viruses," *Nature*, 388(6639):296-300 (Jul. 17, 1997).

Donzella, G.A., et al., "AMD3100, a small molecule inhibitor of HIV-1 entry via the CXCR4 coreceptor," *Nat. Med.*, 4(1):72-77 (Jan. 1998).

Doranz, B.J., et al., "A dual-tropic primary HIV-1 isolate that uses fusin and the beta-chemokine receptors CKR-5, CKR-3, and CKR-2b as fusion cofactors," *Cell*, 85(7):1149-1158 (Jun. 28, 1996).

Dwinell, M.B., et al., "Chemokine receptor expression by human intestinal epithelial cells," *Gastroenterology*, 117(2):359-367 (Aug. 1999).

Eitner, F., et al., "Chemokine receptor (CXCR4) mRNA-expressing leukocytes are increased in human renal allograft rejection," *Transplantation*, 66(11):1551-1557 (Dec. 15, 1998).

Feng, Y, et al., "HIV-1 entry cofactor: functional cDNA cloning of a seven-transmembrane, G protein-coupled receptor," *Science*, 272(5263):872-877 (May 10, 1996).

Förster, R., et al., "CCR7 coordinates the primary immune response by establishing functional microenvironments in secondary lymphoid organs," *Cell*, 99(1):23-33 (Oct. 1, 1999).

Fujii, N., et al., "The therapeutic potential of CXCR4 antagonists in the treatment of HIV," *Expert Opin. Investig. Drugs*, 12(2):185-195 (Feb. 2003).

Gonzalo, J.A., et al., "Critical involvement of the chemotactic axis CXCR4/stromal cell-derived factor-1 alpha in the inflammatory component of allergic airway disease," *J. Immunol.*, 165(1),499-508 (Jul. 1, 2000).

Grove, G., "Epidermal cell kinetics in psoriasis," *Int. J. Dermatol.*, 18(2):111-122 (Mar. 1979).

Gupta, S.K., et al., "Chemokine receptors in human endothelial cells. Functional expression of CXCR4 and its transcriptional regulation by inflammatory cytokines," *J. Biol. Chem.*, 273(7):4282-4287 (Feb. 13, 1998).

Harris, E. D., Jr., "Rheumatoid arthritis. Pathophysiology and implications for therapy," *N. Eng. J. Med.*, 322(18):1277-1289 (May 3, 1990).

Hatse, S., et al., "Chemokine receptor inhibition by AMD3100 is strictly confined to CXCR4," *FEBS Lett* 527(1-3):255-262 (Sep. 11, 2002).

Hendrix, C.W., et al., "Safety, pharmacokinetics, and antiviral activity of AMD3100, a selective CXCR4 receptor inhibitor, in HIV-1 infection," *J. Acquir. Immune Defic. Syndr.*, 37(2):1253-1262 (Oct. 1, 2004).

Homey, B., et al., "Cutting edge: the orphan chemokine receptor G protein-coupled receptor-2 (GPR-2, CCR10) binds the skin-associated chemokine CCL27 (CTACK/ALP/ILC)," *J. Immunol.*, 164(7):3465-3470 (Apr. 1, 2000).

Kang, Y., et al., "A multigenic program mediating breast cancer metastasis to bone," *Cancer Cell*, 3(6):537-549 (Jun. 2003).

Kijowski, J., et al., "The SDF-1-CXCR4 axis stimulates VEGF secretion and activates integrins but does not affect proliferation and survival in lymphohematopoietic cells," *Stem Cells* 19(5):453-466 (2001).

Linton, B.R., et al., "Thermodynamic aspects of dicarboxylate recognition by simple artificial receptors," *J. Org. Chem.*, 66(22):7313-7319 (Nov. 2, 2001).

Majka, M., et al., "Biological significance of chemokine receptor expression by normal human megakaryoblasts," *Folia. Histochem. Cytobiol.* 39(3):235-244 (2001).

Mićović, V.M., and Mihailović, M.LJ., "The Reduction of Acid Amides with Lithium Aluminum Hydride," *J. Org. Chem.*, 18(9):1190-1200(1953).

Mitra, P., et al., "CXCR4 mRNA expression in colon, esophageal and gastric cancers and hepatitis C infected liver," *Int. J. Oncol.*, 14(5):917-925 (May 1999).

Morales, J., et al., "CTACK, a skin-associated chemokine that preferentially attracts skin-homing memory T cells," *Proc. Natl. Acad. Sci. U.S.A.*, 96(25):14470-14475 (Dec. 7, 1999).

Müller, A., et al., "Involvement of chemokine receptors in breast cancer metastasis," *Nature*, 410(6824):50-56 (Mar. 1, 2001).

Murdoch, C., et al., "Functional expression of chemokine receptor CXCR4 on human epithelial cells," *Immunology*, 98(1):36-41 (Sep. 1998).

Murdock, K.C., et al., "Antitumor agents. 2. Bisguanylhydrazones of anthracene-9,10-dicarboxaldehydes," *J. Med. Chem.* 25(5):505-518 (May 1982).

Nagase, H., et al., "Expression of CXCR4 in eosinophils: functional analyses and cytokine-mediated regulation," *J. Immunol.*, 164(11):5935-5943 (Jun. 1, 2000).

Nanki, T., and Lipsky, P.E., et al., "Cutting edge: stromal cell-derived factor-1 is a costimulator for CD4+ T cell activation," *J. Immunol.*, 164(10):5010-5014 (May 15, 2000).

Onuffer, J.J., and Horuk, R., "Chemokines, chemokine receptors and small-molecule antagonists: recent developments," *Trends Pharmacol. Sci.*, 23(10):459-467 (Oct. 2002).

Peled, A., et al., "Dependence of human stem cell engraftment and repopulation of NOD/SCID mice on CXCR4," *Science*, 283(5403):845-848 (Feb. 5, 1999).

Post, D. E., and Van Meir, E. G., "Generation of bidirectional hypoxia/HIF-responsive expression vectors to target gene expression to hypoxic cells," *Gene Ther.*, 8(23):1801-1807 (Dec. 2001).

Reyes, M.J., et al., "Pyridinium N-(2'-azinyl)aminides: regioselective synthesis of N-(2-pyridyl) substituted polyamines," *Tetrahedron*, 58(42):8573-8579 (Oct. 14, 2002).

Ross, R., "The pathogenesis of atherosclerosis: a perspective for the 1990s," *Nature*, 362(6423):801-809 (Apr. 29, 1993).

Sanchez, X., et al., "Activation of HIV-1 coreceptor (CXCR4) mediates myelosuppression," *J. Biol. Chem.*, 272(34):27529-27531 (Oct. 31, 1997).

Schols, D., et al., "Bicyclams, a class of potent anti-HIV agents, are targeted at the HIV coreceptor fusin/CXCR-4," *Antiviral Res.*, 35(3):147-156 (Aug. 1997).

Scozzafava, A., et al. "Non-peptidic chemokine receptors antagonists as emerging anti-HIV agents," *J. Enzyme Inhib. Med. Chem.*, 17(2):69-76 (Apr. 2002).

Sotsios, Y., et al., "The CXC chemokine stromal cell-derived factor activates a Gi-coupled phosphoinositide 3-kinase in T lymphocytes," *J. Immunol.*, 163(11): 5954-5963 (Dec. 1, 1999).

Staller, P., et al., "Chemokine receptor CXCR4 downregulated by von Hippel-Lindau tumour suppressor pVHL," *Nature*, 425(6955):307-311 (Sep. 18, 2003).

Tamamura, H., et al., "A low-molecular-weight inhibitor against the chemokine receptor CXCR4: a strong anti-HIV peptide T140," *Biochem. Biophys. Res. Commun.*, 253(3): 877-882 (Dec. 30, 1998).

Tamamura, H., et al., "Development of specific CXCR4 inhibitors possessing high selectivity indexes as well as complete stability in serum based on an anti-HIV peptide T140," *Bioorg. Med. Chem. Lett.*, 11(14):1897-1902 (Jul. 23, 2001).

Tamamura, H., et al., "Pharmacophore identification of a specific CXCR4 inhibitor, T140, leads to development of effective anti-HIV agents with very high selectivity indexes," *Bioorg. Med. Chem. Lett.*, 10(23):2633-2637 (Dec. 4, 2000).

Trent, J.O., et al., "Lipid bilayer simulations of CXCR4 with inverse agonists and weak partial agonists," *J. Biol. Chem.*, 278(47):47136-47144 (Nov. 21, 2003) (Epublication Sep. 4, 2003).

Vlahakis, S.R., et al., "G protein-coupled chemokine receptors induce both survival and apoptotic signaling pathways," *J. Immunol.* 169(10):5546-5554 (Nov. 15, 2002).

Volin, M.V., et al., "Chemokine receptor CXCR4 expression in endothelium," *Biochem Biophys Res Commnun.*, 242(1):46-53 (Jan. 6, 1998).

Xia, M.Q., and Hyman, B.T., "Chemokines/chemokine receptors in the central nervous system and Alzheimer's disease," *J. NeuroVirol.*, 5(1):32-41 (Feb. 1999).

Yssel, H., et al., "The role of IgE in asthma," *Clin. Exp. Allergy*; 28(28 Suppl. 5):104-109; discussion 117-118 (Nov. 1998).

Zaitseva, M., et al., "Expression and function of CCR5 and CXCR4 on human Langerhans cells and macrophages: implications for HIV primary infection," *Nat. Med.*, 3(12):1369-1375 (Dec. 1997).

Zlotnik, A., and Yoshie, O., "Chemokines: a new classification system and their role in immunity," *Immunity*, 12(2):121-127 (Feb. 2000).

Zou, R.-Y., et al., "1,4-Bis(pyridine-2-aminomethyl)benzene," *Acta Crystallographica Section E*, E59(9):(online)o1312-o1313 (Sep. 2003) (Provided as publisher's abstract).

Gagliardi et al., "Antiangiogenic and antiproliferative activity of surimin analogues," *Cancer Chemother. Pharmacol.* 1998, vol. 41, pp. 117-124.

Tu et al., Toward the Design of Novel Polynuclear Platinum Antitumor Complexes, Inorganic Chemistry, 2003, vol. 42 No. 19, pp. 5795-5797.

Coats et al.; Correlation analysis of pyrimidine folic acid antagonists as antibacterial agents; *Eur. J. of Medicinal Chem.*; 14(3), May 1, 1979; pp. 261-270.

Sellarajah, S. et al.; Synthesis of analogues of congo red and evaluation of their anti-prion activity; *J. of Medicinal Chem.*; vol. 47; Jan. 1, 2004; pp. 5515-5534.

Zhan W. et al.; Discovery of small molecule CXCR antagonists; *J. of Medicinal Chem.*; vol. 50 (23); Nov. 1, 2007; pp. 5655-5664.

Zhan, et al., Discovery of Small Molecule CXCR4 Antagonists, J of Medicinal Chemistry, 2007, 50; pp. 5655-5664.

Zhu, et al, "Dipyrimidine Amines: A Novel Class of Chemokine Receptor Type 4 Antagonist with High Specificity", J of Medicinal Chemistry, 2010, 53; pp. 8556-8568.

Charter, Neil, 2011, Profiling Report—Target CXCR4.

Daugherty, Bruce, 2011, CXCR4 ligand binding assay Using [3 H]-MSX-122.

Otto-Bruc, Annie, 2011, in Vitro Pharmacology: Human CXCR4 Receptor Functional Assay Study of AMD3100 and MSX-122.

\* cited by examiner

Figure 3. Incubating MDA-MB-231 cells with 100 ng/ml of SDF-1 for 30 min stimulated phosphorylation of Akt. This activation was blocked with TN14003 or AMD3100 in a dose-dependent manner.

4HCl   $C_{18}H_{22}Cl_4N_4$
       MW - 436.21

WZZL811S

CXCR4 ANTAGONISTS FOR THE TREATMENT OF HIV INFECTION

CROSS-REFERENCE TO RELATED APPLICATIONS

This application claims priority to U.S. Provisional Application No. 60/642,375, filed Jan. 7, 2005, U.S. Provisional Application No. 60/642,374, filed Jan. 7, 2005 and U.S. Provisional Application No. 60/682,655, filed May 18, 2005 now abandoned.

FIELD OF THE INVENTION

The invention provides compounds, pharmaceutical compositions and methods of use of certain compounds that are antagonists of the chemokine CXCR4 receptor. The compounds are useful to modulate a medical condition that is modulated by CXCR4 receptor activity or signaling, and in particular in the treatment or prevention of human immunodeficiency virus infections (HIV).

BACKGROUND

As of the end of 2004, an estimated 39.4 million people worldwide were living with HIV/AIDS, and the Centers for Disease Control and Prevention (CDC) estimate that 850,000 to 950,000 U.S. residents are living with HIV infection (UN-AIDS/WHO AIDS epidemic update, December 2004; Fleming, P. L. et al. HIV Prevalence in the United States, 2000. 9th Conference on Retroviruses and Opportunistic Infections, Seattle, Wash., Feb. 24-28, 2002. Abstract 11). Although new infections have decreased in recent years, an estimated 4.9 million new HIV infections occurred worldwide during 2004 and approximately 40,000 new HIV infections occur each year in the United States.

HIV entry within the target cells involves a series of molecular events. The three main steps of virus entry within the cell are: (i) attachment of the virus to the host cells; (ii) interaction of the virus with the co-receptors; (iii) fusion of the virus and host cell membranes. Considering the complexity of the molecular events involved in viral infection, all three of these steps have been considered for the drug design of HIV entry inhibitors. The T-lymphocyte cell surface protein CD4 is the primary receptor involved in the interaction with the viral glycoprotein gp120, but a cellular co-receptor is also needed for the successful entry of the virus within the cell. At least two types of such co-receptors have been identified so far, both of which are chemokine receptors. These chemokine receptors are therefore gateways for HIV entry, determinants of viral tropism and sensitivity.

Chemokines are a superfamily of small, secreted cytokines that induce, through their interaction with G-protein-coupled receptors, cytoskeletal rearrangements and directional migration of several cell types (Butcher, et al. (1999) *Adv Immunol* 72: 209-253; Campbell and Butcher (2000) *Curr Opin Immunol* 12: 336-341; Zlotnik and Yoshie (2000) *Immunity* 12: 121-127). The chemokine receptor, CXCR4, is known in viral research as a major coreceptor for the entry of T cell line-tropic HIV (Feng, et al. (1996) *Science* 272: 872-877; Davis, et al. (1997) *J Exp Med* 186: 1793-1798; Zaitseva, et al. (1997) *Nat Med* 3: 1369-1375; Sanchez, et al. (1997) *J Biol Chem* 272: 27529-27531). T Stromal cell derived factor 1 (SDF-1) is a chemokine that interacts specifically with CXCR4. When SDF-1 binds to CXCR4, CXCR4 activates $G\alpha_i$-protein-mediated signaling (pertussis toxin-sensitive) (Chen, et al. (1998) *Mol Pharmacol* 53: 177-181), including downstream kinase pathways such as Ras/MAP Kinases and phosphatidylinositol 3-kinase (PI3K)/Akt in lymphocyte, megakaryocytes, and hematopoietic stem cells (Bleul, et al. (1996) *Nature* 382: 829-833; Deng, et al. (1997) *Nature* 388: 296-300; Kijowski, et al. (2001) *Stem Cells* 19: 453-466; Majka, et al. (2001) *Folia. Histochem. Cytobiol.* 39: 235-244; Sotsios, et al. (1999) *J. Immunol.* 163: 5954-5963; Vlahakis, et al. (2002) *J. Immunol.* 169: 5546-5554).

Compounds targeting CXCR4 have been developed which are aimed at treatment of HIV infection. For example, U.S. Pat. No. 6,429,308 to Hisamitsu Pharmaceutical Co., Inc. discloses an antisense oligonucleotide to CXCR4 to inhibit the expression of the CXCR4 protein for use as an anti-HIV agent.

Peptide antagonists of CXCR4 receptors have also been disclosed. Tamamura et al (Tamamura, et al. (2000) *Bioorg. Med. Chem. Lett.* 10: 2633-2637; Tamamura, et al. (2001) *Bioorg. Med. Chem. Lett.* 11: 1897-1902) reported the identification of a specific peptide-based CXCR4 inhibitor, T140. T140 is a 14-residue peptide that possessed high levels of anti-HIV activity and antagonism of T cell line-tropic HIV-1 entry among all antagonists of CXCR4 (Tamamura, et al. (1998) *Biochem. Biophys. Res. Commun.* 253: 877-882). The compound has been altered to increase its efficacy and bioavailability by, for example, amidating the C-terminal of T-140 and reducing the total positive charges by substituting basic residues with nonbasic polar amino acids to generate TN14003, which is less cytotoxic and more stable in serum compared to T140. The concentration of TN14003 required for 50% protection of HIV-induced cytopathogenicity in MT-4 cells is 0.6 nM in contrast to 410 µM leading to 50% toxicity. U.S. Pat. No. 6,344,545 to Progenics Pharmaceuticals, Inc. describes methods for preventing HIV-1 infection of CD4+ cells with peptide fragments. U.S. Pat. No. 6,534,626 to the U.S. Department of Health & Human Services describes certain peptide chemokine variants for treating HIV infections.

Although advances have been made, inadequate absorption, distribution, metabolism, excretion or toxicity properties of peptide inhibitors have limited their clinical use. Small non-peptide drugs remain a major goal of medicinal chemistry programs in this area.

At the present time, the metal-chelating cyclams and bicyclams represent one of the few reported non-peptide molecules to effectively block CXCR4 (Onuffer and Horuk (2002) *Trends Pharmacol Sci* 23: 459-467.36). One of these non-peptide molecules is AMD3100, which entered clinical trials as an anti-HIV drug that blocks CXCR4-mediated viral entry (Donzella, et al. (1998) *Nat Med* 4: 72-77; Hatse, et al. (2002) *FEBS Lett* 527: 255-262; Fujii, et al. (2003) *Expert Opin Investig Drugs* 12: 185-195; Schols, et al. (1997) *Antiviral Res* 35: 147-156).

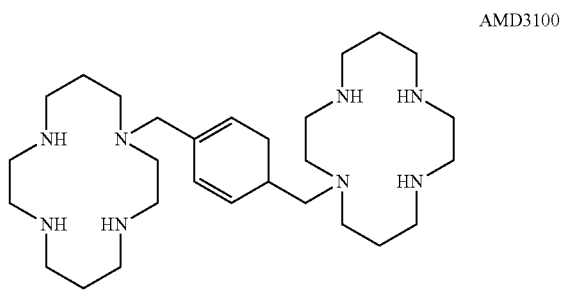

AMD3100

However, a clinical study showed cardiac-related side effect of AMD3100 (Scozzafava, et al. (2002) *J Enzyme Inhib Med Chem* 17: 69-7641). In fact, AMD3100, was recently withdrawn from the clinical trials due in part to a cardiac-related side effect (Hendrix, et al. (2004) *Journal of Acquired Immune Deficiency Syndromes* 37(2)). The latter was not a result of the compound's ability to block CXCR4 function, but due to its presumed structural capacity for encapsulating metals.

Other nitrogen containing bicyclic molecules have also been developed as CXCR4 antagonists. European Patent Publication No. 1 431 290 and PCT Publication No. WO 02/094261 to Kureha Chemical Industry Co., Ltd cover CXCR4 inhibitors that are potentially useful in treating various diseases including HIV infection.

U.S. Patent Publication No. 2004/0254221 to Yamamazi, et al. also provides compounds and use thereof to treat various diseases including HIV infections that are CXCR4 antagonists. The compounds are of the general formula:

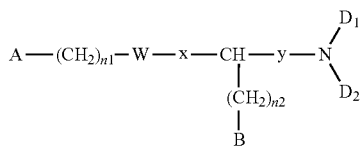

in which A is $A_1$-$G_1$-N($R_1$)—; $A_1$ is hydrogen or an optionally substituted, mono- or polycyclic, heteroaromatic or aromatic ring; $G_1$ is a single bond or —C($R_2$)($R_3$)—; $R_1$, $R_2$, and $R_3$ can be optionally substituted hydrocarbon groups; W is an optionally substituted hydrocarbon or heterocyclic ring; x is —C(=O)NH—; y is —C(=O)—; and $D_1$ is hydrogen atom, alkyl with a polycyclic aromatic ring, or amine.

PCT Publication No. WO 00/56729 and U.S. Pat. No. 6,750,348 to AnorMED describe certain heterocyclic small molecule CXCR4 binding compounds, teaching that these are useful for the protection against HIV infection. The compounds are of the general formula:

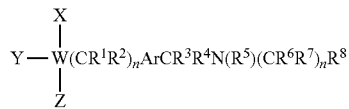

in which W can be a nitrogen or carbon atom; Y is absent or is hydrogen; $R^1$ to $R^7$ can be hydrogen or straight, branched or cyclic $C_{1-6}$ alkyl; $R^8$ is a substituted heterocyclic or aromatic group; Ar is an aromatic or heteroaromatic ring; and X is specified ring structure.

PCT Publication No. WO 2004/091518 to AnorMED also describes certain substituted nitrogen containing compounds that bind to CXCR4 receptors. The compounds are described as having the effect of increasing progenitor cells and/or stem cells, enhancing production of white blood cells, and exhibiting antiviral properties. PCT Publication No. WO 2004/093817 to AnorMED also discloses substituted heterocyclic CXCR4 antagonists which are described as useful to alleviate inflammatory conditions and elevate progenitor cells, as well as white blood cell counts. Similarly, PCT Publication No. WO 2004/106493 to AnorMED describes heterocyclic compounds that bind to CXCR4 and CCR5 receptors consisting of a core nitrogen atom surrounded by three pendant groups, wherein two of the three pendant groups are preferably benzimidazolyl methyl and tetrahydroquinolyl, and the third pendant group contains nitrogen and optionally contains additional rings. The compounds demonstrate protective effects against infections of target cells by a human immunodeficiency virus (HIV).

It is an object of the invention to provide new compounds, methods and compositions for the treatment of viral infection, notably HIV.

SUMMARY

Compounds, methods and pharmaceutical compositions for the treatment or prevention of diseases viral diseases, notably HIV, or symptoms associated with HIV infection or AIDS (acquired immune deficiency syndrome) are provided. While not wanting to be bound by theory, it is believed that the compounds provided herein may interfere with the binding of the native SDF-1 ligand to the CXCR4 receptor and inhibit activation of the receptor and subsequent downstream signaling pathways. The invention provides compounds, methods and pharmaceutical compositions for the treatment of pathogenic conditions including certain viral diseases, in particular HIV infection, and particularly for the reduction of cell invasion by the virus. The compounds, methods and compositions include an effective treatment amount of a compound of Formulas (I)-(XVII), or a pharmaceutically acceptable salt, ester or prodrug thereof.

In one embodiment, a method, compound and pharmaceutical composition for the treatment or prevention of HIV infection, or for reduction of symptoms associated with AIDS, in a host in need thereof is provided including a compound of Formula I, or a pharmaceutically acceptable salt, ester or prodrug thereof:

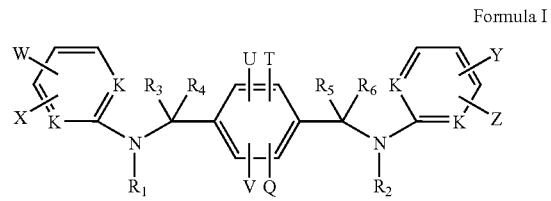

Formula I wherein
each K is independently N or CH;
Q, T, U, V, W, X, Y and Z are independently selected from H, R, acyl, F, Cl, Br, I, OH, OR, $NH_2$, NHR, $NR_2$, SR, SR, $S_2R$, S—NHR, $S_2$—NHR, S—NRR', $S_2$—NRR', NHacyl, N(acyl)$_2$, $CO_2H$, $CO_2R$, where R and R' are independently selected from straight chain, branched or cyclic alkyl or aralkyl groups, as well as aryl and heteroaryl groups; and
$R_1$, $R_2$, $R_3$, $R_4$, $R_5$ and $R_6$ are independently selected from H, straight chain, branched or cyclic alkyl, aralkyl, aryl heteroaryl, acyl (RC—) and imidoyl (RC(NH)— or RC(NR')—) groups.

In another embodiment, the compound has the formula:

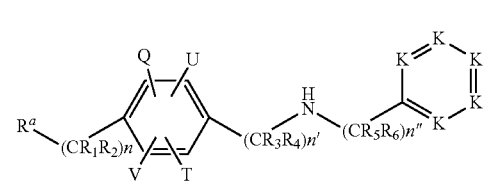

1b wherein each K is independently N or CH;
Q, T, U, and V are independently selected from H, R, acyl, F, Cl, Br, I, OH, OR, $NH_2$, NHR, $NR_2$, SR, SR, $S_2R$, S—NHR, $S_2$—NHR, S—NRR', $S_2$—NRR', NHacyl, N(acyl)$_2$, CO$_2$H, CO$_2$R, where each R and R' are independently selected from straight chain, branched or cyclic alkyl or aralkyl groups, as well as aryl and heteroaryl groups;

R$^a$ is independently selected from R, acyl, F, Cl, Br, I, OH, OR, NH$_2$, NHR, NO$_2$, NR$_2$, SO$_2$, SR, S$_2$R, S—NHR, S$_2$—NHR, S—NRR', S$_2$—NRR', NHacyl, N(acyl)$_2$, C(=O)R, CO$_2$H, CO$_2$R;

n, n' and n" are independently 0, 1, 2, 3, 4, or 5; and

R$_1$, R$_2$, R$_3$, R$_4$, R$_5$ and R$_6$ are independently selected from H, straight chain, branched or cyclic alkyl, aralkyl, aryl heteroaryl, acyl (RC—) and imidoyl (RC(NH)— or RC(NR')—) groups.

In another embodiment the compound has the formula:

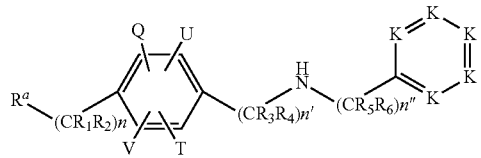

each K is independently N or CH;

Q, T, U, and V are independently selected from H, R, acyl, F, Cl, Br, I, OH, OR, NH$_2$, NHR, NR$_2$, SR, SR, S$_2$R, S—NHR, S$_2$—NHR, S—NRR', S$_2$—NRR', NHacyl, N(acyl)$_2$, CO$_2$H, CO$_2$R, where each R and R' are independently selected from straight chain, branched or cyclic alkyl or aralkyl groups, as well as aryl and heteroaryl groups;

R$^a$, n, n' and n" and R$_1$, R$_2$, R$_3$, R$_4$, R$_5$ and R$_6$ are as defined above.

In another embodiment, a method, compound and pharmaceutical composition for the treatment or prevention of HIV infection, or for reduction of symptoms associated with AIDS, in a host in need thereof is provided including a compound of Formula IIa or IIb, or a pharmaceutically acceptable salt, ester or prodrug thereof:

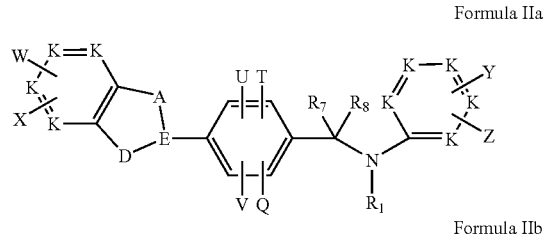

wherein each K is independently N or CH;

Q, T, U, V, W, X, Y and Z are as defined above;

A and B are one and two atom tethers independently selected from —CR=, —CR$_3$R$_4$—, —CR$_3$=, —N=, —O—, —NR$_3$—, —S—, —CR$_3$—CR$_4$—, —CR$_3$R$_4$—CR$_5$R$_6$—, —CR$_3$=N—, —CR$_0$R$_4$—NR$_5$—, —N=CR$_3$—, and —NR$_3$—CR$_4$R$_5$—;

R and R' are as defined above;

-D-E- and -G-J- are independently either —NR$_3$—CR$_4$— or —N=C—; and

R$_1$, R$_2$, R$_3$, R$_4$, R$_5$, R$_6$, R$_7$ and R$_8$ are independently selected from H, straight chain, branched or cyclic alkyl, aralkyl, aryl heteroaryl, acyl (RC—) and imidoyl (RC(NH)— or RC(NR')—) groups.

In another embodiment, a method, compound and pharmaceutical composition for the treatment or prevention of HIV infection, or for reduction of symptoms associated with AIDS, in a host in need thereof is provided including a compound of Formula III, or a pharmaceutically acceptable salt, ester or prodrug thereof:

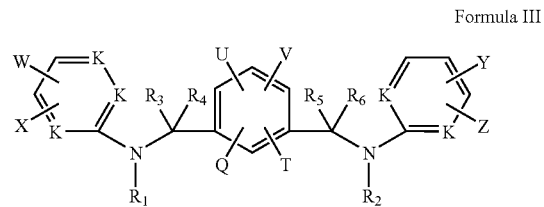

wherein each K is independently N or CH;

Q, T, U, V, W, X, Y and Z are as defined above; and

R, R', R$_1$, R$_2$, R$_3$, R$_4$, R$_5$ and R$_6$ are as defined above.

In a further embodiment, a method, compound and pharmaceutical composition for the treatment or prevention of HIV infection, or for reduction of symptoms associated with AIDS, in a host in need thereof is provided including a compound of Formula IVa or IVb, or a pharmaceutically acceptable salt, ester or prodrug thereof:

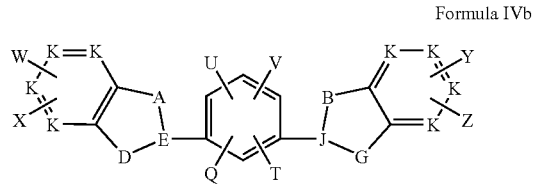

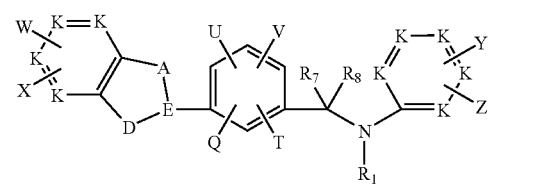

wherein each K is independently N or CH;

Q, T, U, V, W, X, Y and Z are as defined above;

R, R', R$_1$, R$_2$, R$_3$, R$_4$, R$_5$, R$_6$, R$_7$ and R$_8$ are as defined above; and A and B and -D-E- and -G-J- are as defined above.

In another embodiment, a method, compound and pharmaceutical composition for the treatment or prevention of HIV infection, or for reduction of symptoms associated with AIDS, in a host in need thereof is including a compound of Formula Va, Vb or Vc, or a pharmaceutically acceptable salt, ester or prodrug thereof:

Formula Va

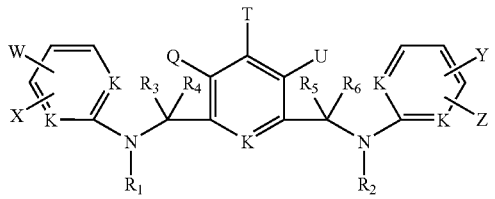

Formula Vb

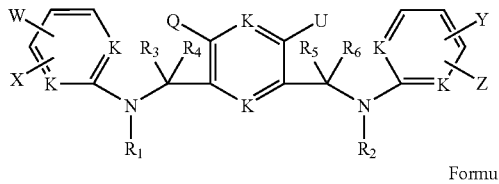

Formula Vc

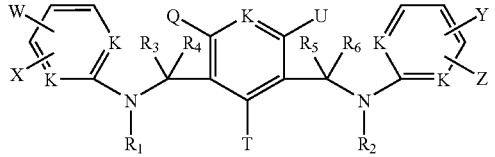

wherein
each K is independently N or CH;
Q, T, U, W, X, Y and Z are as defined above; and
R, R', $R_1$, $R_2$, $R_3$, $R_4$, $R_5$ and $R_6$ are as defined above.

In a further embodiment, a method, compound and pharmaceutical composition for the treatment or prevention of HIV infection, or for reduction of symptoms associated with AIDS, in a host in need thereof is provided including a compound of Formula VIa or VIb, or a pharmaceutically acceptable salt, ester or prodrug thereof:

Formula VIa

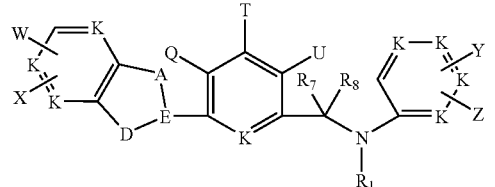

Formula VIb

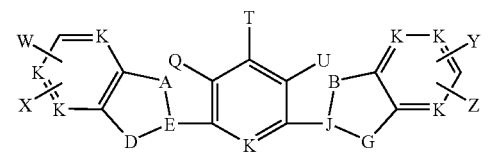

wherein
each K is independently N or CH;
Q, T, U, W, X, Y and Z are as defined above;
R, R', $R_1$, $R_2$, $R_3$, $R_4$, $R_5$, $R_6$, $R_7$ and $R_8$ are as defined above; and
A and B and -D-E- and -G-J- are as defined above.

In yet another embodiment, a method, compound and pharmaceutical composition for the treatment or prevention of HIV infection, or for reduction of symptoms associated with AIDS, in a host in need thereof is provided including a compound of Formula VII, or a pharmaceutically acceptable salt, ester or prodrug thereof:

Formula VII

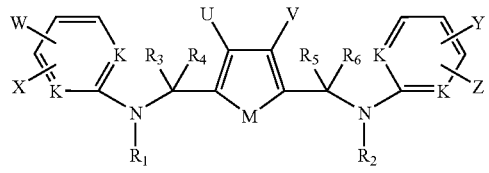

wherein
each K is independently N or CH;
U, V, W, X, Y and Z are as defined above;
$R_1$, $R_2$, $R_3$, $R_4$, $R_5$ and $R_6$ are as defined above; and
M is O, S or $NR_3$.

In a further embodiment, a method, compound and pharmaceutical composition for the treatment or prevention of HIV infection, or for reduction of symptoms associated with AIDS, in a host in need thereof is provided including a compound of Formula VIIIa or VIIIb, or a pharmaceutically acceptable salt, ester or prodrug thereof:

Formula VIIIa

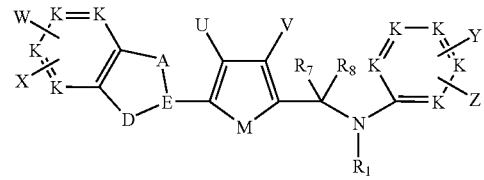

Formula VIIIb

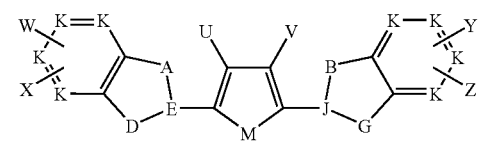

wherein
each K is independently N or CH;
U, V, W, X, Y and Z are as defined above;
$R_1$, $R_2$, $R_3$, $R_4$, $R_5$, $R_6$, $R_7$ and $R_8$ are as defined above; and
A and B and -D-E- and -G-J- are as defined above; and
M is O, S or $NR_3$.

In a ninth principal embodiment, a method, compound and pharmaceutical composition for the treatment or prevention of HIV infection, or for reduction of symptoms associated with AIDS, in a host in need thereof is provided including a compound of Formula IX, or a pharmaceutically acceptable salt, ester or prodrug thereof:

Formula IX

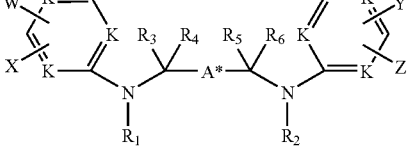

wherein
each K is independently N or CH;
W, X, Y and Z are as defined above;
$R_1$, $R_2$, $R_3$, $R_4$, $R_5$ and $R_6$ are as defined above;
A* is independently selected from the group consisting of formulas a-g:

(a) 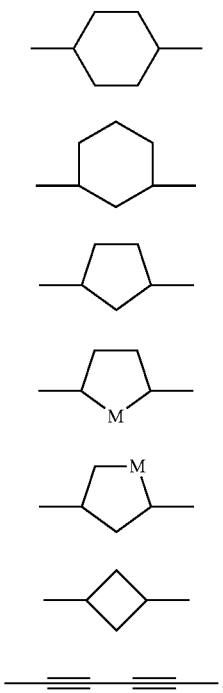

(b)

(c)

(d)

(e)

(f)

(g) 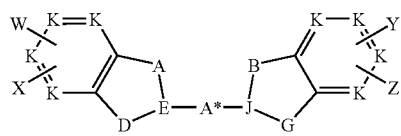;

and

M is O, S or NR$_3$.

In another embodiment, a method, compound and pharmaceutical composition for the treatment or prevention of HIV infection, or for reduction of symptoms associated with AIDS, in a host in need thereof is provided including a compound of Formula X, or a pharmaceutically acceptable salt, ester or prodrug thereof:

Formula X

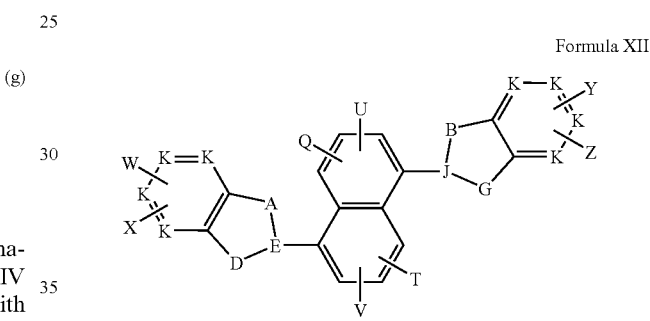

wherein each K is independently N or CH;

W, X, Y and Z are as defined above;

$R_1, R_2, R_3, R_4, R_5, R_6, R_7$ and $R_8$ are as defined above; and

A and B and -D-E- and -G-J- are as defined above; and

A* is as defined above; and

M is as defined above.

In another principal embodiment, a method, compound and pharmaceutical composition for the treatment or prevention of HIV infection, or for reduction of symptoms associated with AIDS, in a host in need thereof is provided including a compound of Formula XI, or a pharmaceutically acceptable salt, ester or prodrug thereof:

Formula XI

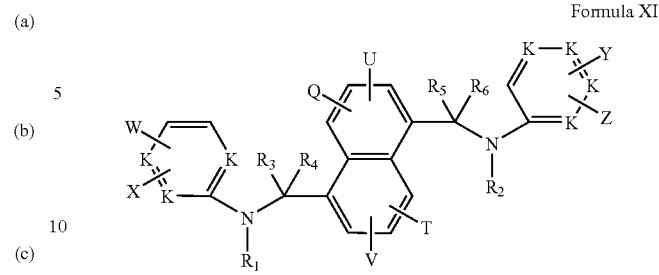

wherein each K is independently N or CH;

Q, T, U, V, W, X, Y and Z are as defined above; and $R_1, R_2, R_3, R_4, R_5$ and $R_6$ are as defined above.

In another embodiment, a method, compound and pharmaceutical composition for the treatment or prevention of HIV infection, or for reduction of symptoms associated with AIDS, in a host in need thereof is provided including a compound of Formula XII, or a pharmaceutically acceptable salt, ester or prodrug thereof:

Formula XII

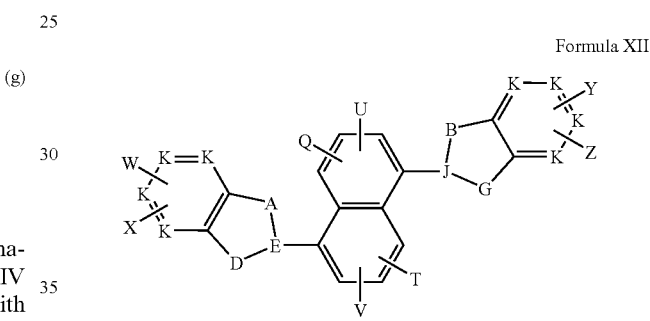

wherein each K is independently N or CH;

Q, T, U, V, W, X, Y and Z are as defined above;

$R_1, R_2, R_3, R_4, R_5, R_6, R_7$ and $R_8$ are as defined above; and

A and B and -D-E- and -G-J- are as defined above.

In another embodiment, a method, compound and pharmaceutical composition for the treatment or prevention of HIV infection, or for reduction of symptoms associated with AIDS, in a host in need thereof is provided including a compound of Formula XIII, or a pharmaceutically acceptable salt, ester or prodrug thereof:

Formula XIII

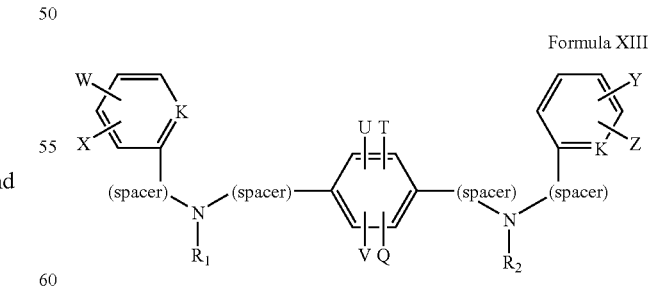

wherein

K, Q, T, U, V, W, X, Y and Z are as defined above;

$R_1, R_2, R_3, R_4, R_5$ and $R_6$ are as defined above; and

"spacer" is independently a bond, straight chained or branched $C_1$-$C_5$ alkyl, $C_2$-$C_5$ alkenyl, $C_2$-$C_5$ alkynyl, $C_1$-$C_5$ alkoxy, $C_2$-$C_5$ alkenoxy, and $C_2$-$C_5$ alkynoxy wherein the alkyl group can be substituted by a heteroatom (such as N, O or S) for example —CH$_2$—OCH$_2$—, —CH$_2$CH$_2$—OCH$_2$, —CH$_2$CH$_2$—OCH$_2$CH$_2$—, —CH$_2$—OCH$_2$CH2-, —CH$_2$CH$_2$—OCH$_2$CH$_2$CH$_2$—, —CH$_2$CH$_2$CH$_2$—OCH$_2$—, —CH$_2$CH$_2$CH$_2$—OCH$_2$CH$_2$—, —CH$_2$CH$_2$—OCH$_2$CH$_2$CH$_2$—, —(CH$_2$)$_n$—OH(CH$_3$)—(CH$_2$)$_n$—, CH$_2$—OH(CH$_3$)—O—CH$_2$, —(CH$_2$)n-, —(CH$_2$)n-CO—, —(CH$_2$)n-N—, —(CH$_2$)n-O—, —(CH$_2$)n-S—, —(CH$_2$O)—, —(OCH$_2$)—, —(SCH$_2$)—, —(CH$_2$S—), -(aryl-O)—, —(O-aryl)-, -(alkyl-O)—, —(O-alkyl)- wherein n is independently 0, 1, 2, 3, 4, 5, 6, 7, 8, 9, or 10.

In another principal embodiment, a method, compound and pharmaceutical composition for the treatment or prevention of HIV infection, or for reduction of symptoms associated with AIDS, in a host in need thereof is provided including a compound of Formula XIVa or XIVb, or a pharmaceutically acceptable salt, ester or prodrug thereof:

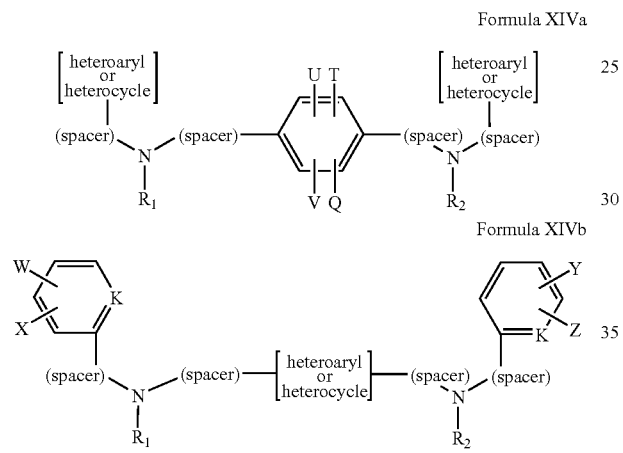

Formula XIVa

Formula XIVb wherein

K, Q, T, U, V, W, X, Y and Z are as defined above;

R$_1$, R$_2$, R$_3$, R$_4$, R$_5$ and R$_6$ are as defined above;

"spacer" is as defined above; and

"heterocycle" and "heteroaromatic" are as defined herein.

In one embodiment, a method of treating or preventing HIV infection, or of reducing symptoms associated with AIDS is provided including administering a compound of Formula (I)-(XVII) to a host. In certain embodiments, the compound can be provided to a host in combination with treatment of the infection with a second active compound. In a separate embodiment, the compound is provided to a patient that has been treated for viral infection to keep viral load low, or reduce mortality associated with a particular infection, for example by reducing progression of AIDS related symptoms. The compound of Formula (I)-(XVII) can also be provided in conjunction with another active compound.

In one particular embodiment, a method of treating or preventing HIV infection, or of reducing symptoms associated with AIDS is provided including administering to a host in need thereof an effective amount of a compound of Formula XV, or a pharmaceutically acceptable salt, ester or prodrug thereof, is provided:

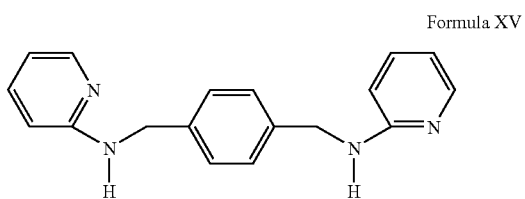

Formula XV

In a particular subembodiment, the compound is a salt of a compound of Formula XV, particularly a chloride salt.

In another particular embodiment, a method of treating or preventing HIV infection, or of reducing symptoms associated with AIDS is provided that includes contacting the cells with a compound of Formula XVI, or a pharmaceutically acceptable salt, ester or prodrug thereof, is provided:

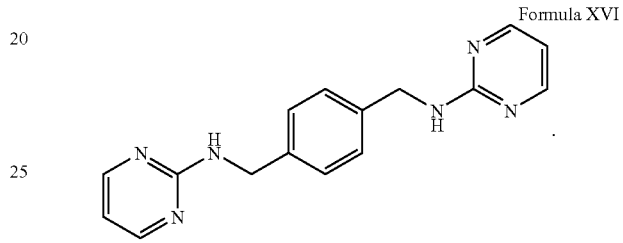

Formula XVI

In another particular embodiment, a method of treating or preventing HIV infection, or of reducing symptoms associated with AIDS is provided that includes contacting the cells with a compound of Formula XVII, or a pharmaceutically acceptable salt, ester or prodrug thereof, is provided:

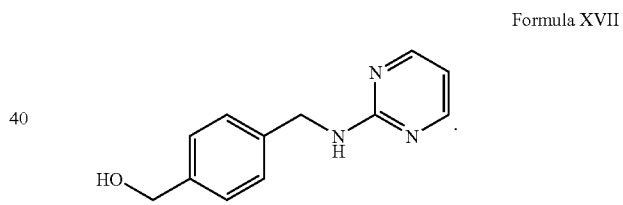

Formula XVII

In a separate embodiment, a method of treating or preventing HIV infection, or of reducing symptoms associated with AIDS by administering a compound of Formulas (I)-(XVII) to a host in need of treatment is provided. The compounds of the invention can be administered to a host in need thereof to reduce the incidence of recurrence of infection.

In another embodiment, the invention provides a method of treating a host infected with other infections associated with CXCR4 receptor activation, for example, liver diseases associated with flavivirus or pestivirus infection, and in particular, HCV or HBV, by administering an effective amount of a compound described herein. The cell can be in a host animal, including a human.

In another embodiment, pharmaceutical compositions including at least one compound of Formulas (I)-(XVII) are provided. In certain embodiments, at least a second active compound is administered to the host to achieve combination therapy. The second active compound can be another antiviral agent.

DETAILED DESCRIPTION OF THE INVENTION

Figure 1:
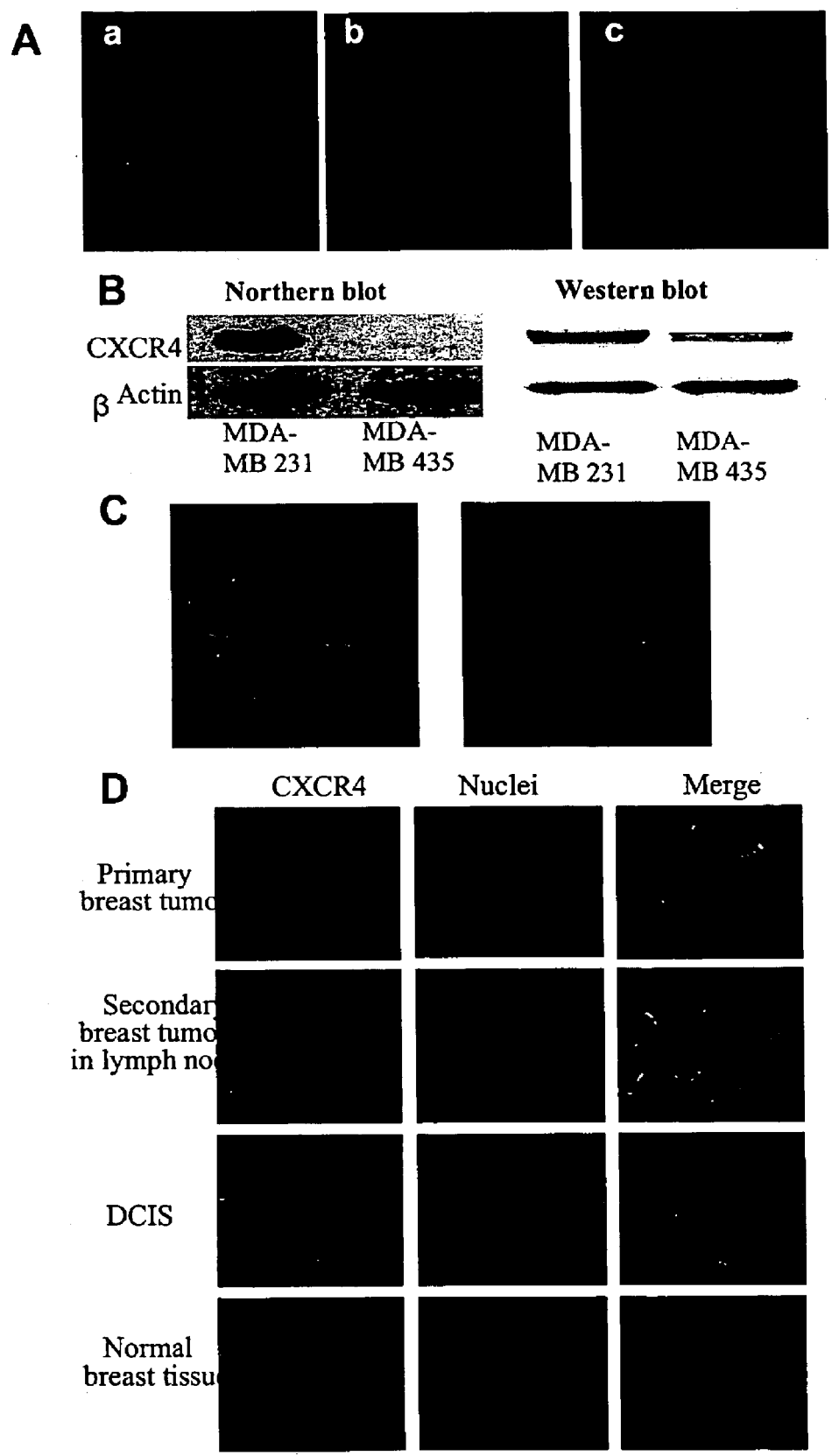
FIG. 1 shows images of stained cells and blots indicating the specificity of TN14003. A: The binding of TN14003 to CXCR4 was blocked by preincubation of 400 ng/ml SDF-1. Cells were immunostained by using biotin-labeled control peptide (a) or biotin-labeled TN14003 (b & c) and streptavidin-conjugated rhodamine (red). Cells were preincubated with SDF-1 for 10 min and then fixed in ice-cold acetone (c). B: Northern blot analysis and western blot analysis results show the different expression levels, of CXCR4 from breast cancer cell lines, MDA-MB-231 and MDA-MB-435. β-actin was used as a loading control for both. C: Confocal micrographs of CXCR4 protein on cell's surface from MDA-MB-231 and MDA-MB-435 cell lines by using biotinylated TN14003 and streptavidin-conjugated R-PE (red color). Nuclei were counter-stained by cytox blue. D: Representative immunofluorescence staining of CXCR4 with the biotinylated TN14003 on paraffin embedded tissue sections of breast cancer patients and normal breast tissue.

Compounds, methods and compositions to treat or prevent HIV infection, reduce viral load or alleviate progression towards or the symptoms of AIDS in a host in need thereof.

Compounds described herein have the capacity to interact with CXCR4 receptors and potentially inhibit receptor signaling. It was found that these compounds have increased bioavailability and efficacy in inhibiting CXCR4 receptors and SDF-1-dependent signaling over known CXCR4 antagonists.

Active Compound, and Physiologically Acceptable Salts and Prodrugs Thereof

In one embodiment, a compound of Formula I, or a pharmaceutically acceptable salt, ester or prodrug thereof, is provided for the treatment or prevention of HIV infection, or for reduction of symptoms associated with AIDS, in a host in need thereof:

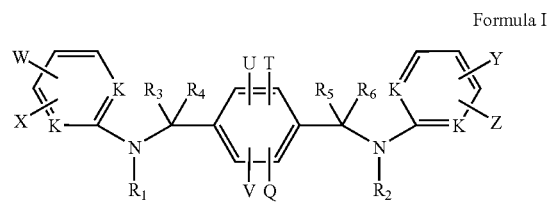

Formula I wherein
each K is independently N or CH;
Q, T, U, V, W, X, Y and Z are independently selected from H, R, acyl, F, Cl, Br, I, OH, OR, $NH_2$, NHR, $NR_2$, SR, SR, $S_2R$, S—NHR, $S_2$—NHR, S—NRR', $S_2$—NRR', NHacyl, $N(acyl)_2$, $CO_2H$, $CO_2R$, where R and R' are independently selected from straight chain, branched or cyclic alkyl or aralkyl groups, as well as aryl and heteroaryl groups; and
$R_1$, $R_2$, $R_3$, $R_4$, $R_5$ and $R_6$ are independently selected from H, straight chain, branched or cyclic alkyl, aralkyl, aryl heteroaryl, acyl (RC—) and imidoyl (RC(NH)— or RC(NR')—) groups In one subembodiment of Formula I, Y and Z are each hydrogen. Alternatively, W and X are each hydrogen. In yet another subembodiment, W, X, Y and Z are all hydrogen.

Zou et al. (Zou, et al. (2003) *Acta Cryst.* E59: online 1312-o1313) described the synthesis of a potentially tetradentate ligand, 1,4-bis-(pyridine-2-aminomethyl)benzene. Zou described this compound as a potential ligand for metal ions.

In a subembodiment, a compound of Formula I-1 to I-10, or a pharmaceutically acceptable salt, ester or prodrug thereof, is provided for the treatment or prevention of HIV infection, or for reduction of symptoms associated with AIDS, in a host in need thereof:

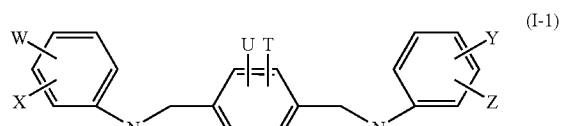

(I-1)

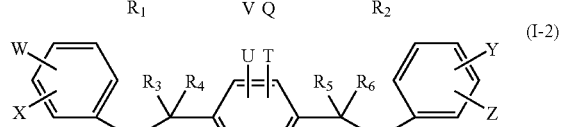

(I-2)

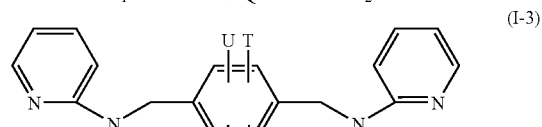

(I-3)

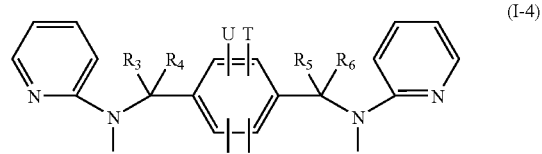

(I-4)

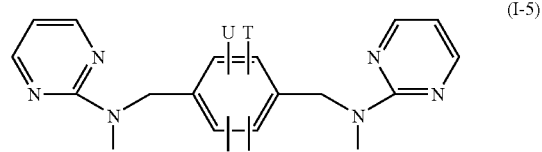

(I-5)

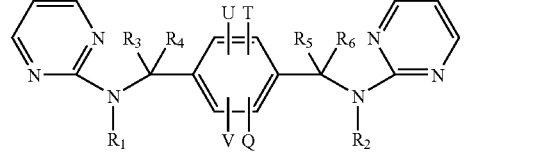

(I-6)

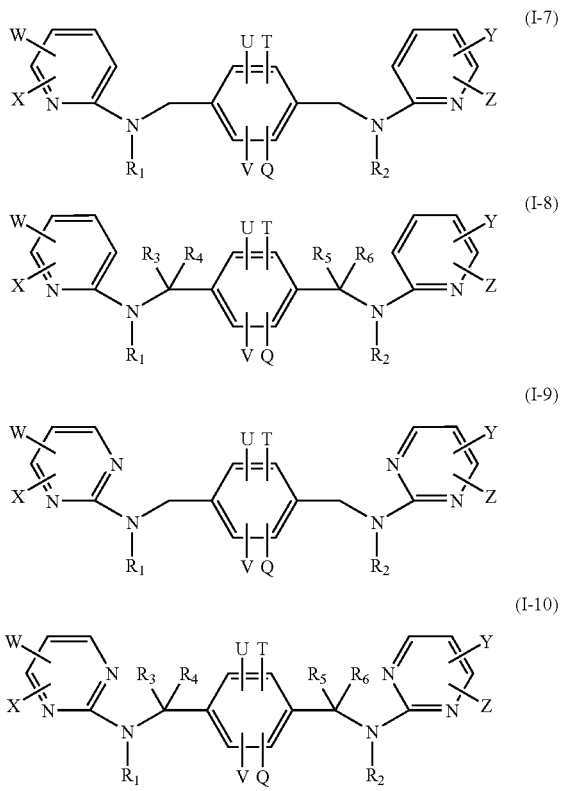

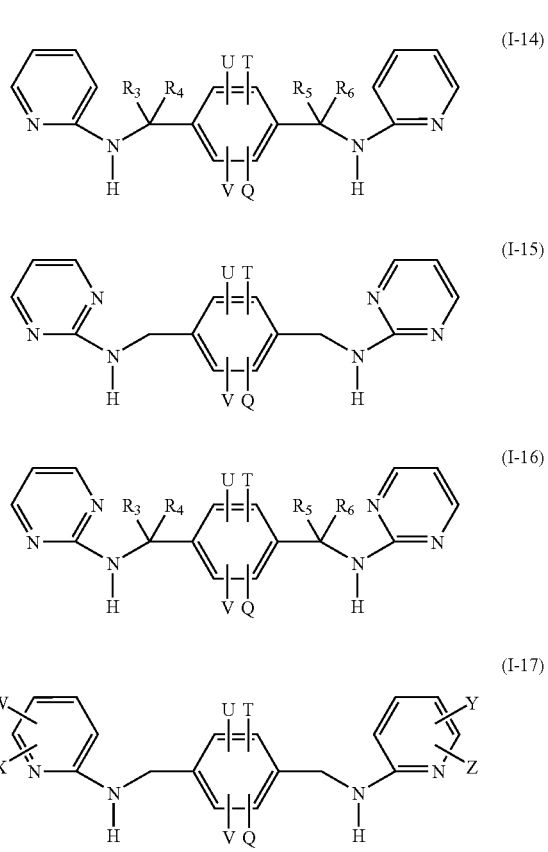

wherein

Q, T, U, V, W, X, Y and Z are as defined above; and $R_1$, $R_2$, $R_3$, $R_4$, $R_5$ and $R_6$ are as defined above.

In another sub-embodiment, a compound of Formula I-11 to I-20, or a pharmaceutically acceptable salt, ester or prodrug, is provided for the treatment or prevention of HIV infection, or for reduction of symptoms associated with AIDS, in a host in need thereof:

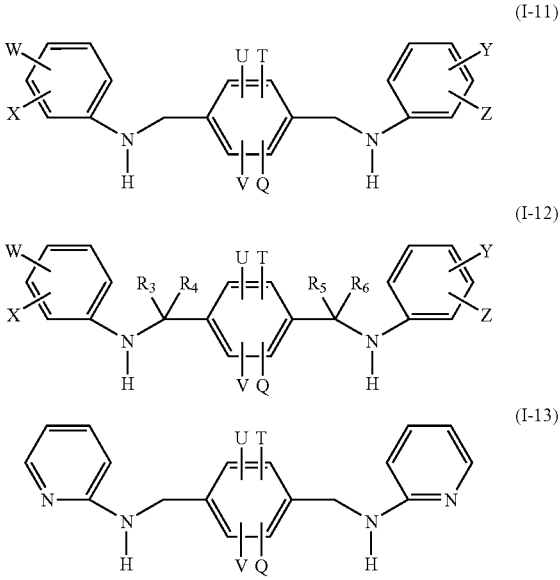

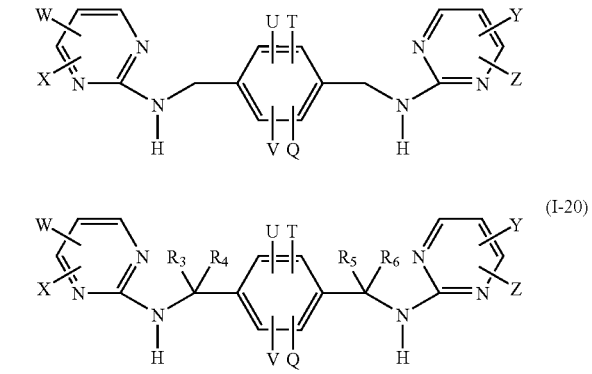

wherein

Q, T, U, V, W, X, Y and Z are as defined above; and $R_1$, $R_2$, $R_3$, $R_4$, $R_5$ and $R_6$ are as defined above.

In another embodiment, the invention provides a compound of Formula IIa or IIb, or a pharmaceutically acceptable salt, ester or prodrug thereof:

Formula IIa

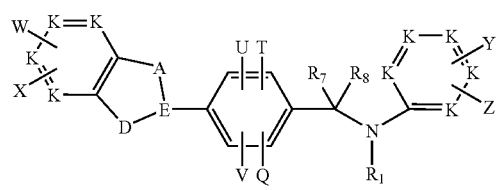

Formula IIb

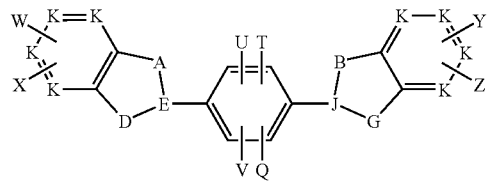

wherein each K is independently N or CH;

Q, T, U, V, W, X, Y and Z are as defined above;

A and B are one and two atom tethers independently selected from —CR=, —CR3R4-, —CR3=, —N=, —O—, —NR$_3$—, —S—, —CR$_3$=CR$_4$—, —CR$_3$R$_4$—CR$_5$R$_6$—, —CR$_3$=N—, —CR$_3$R$_4$—NR$_5$—, —N=CR$_3$—, and —NR$_3$—CR$_4$R$_5$—;

-D-E- and -G-J- are independently either —NR$_3$—CR$_4$— or —N=C—; and $R_1$, $R_2$, $R_3$, $R_4$, $R_5$, $R_6$, $R_7$ and $R_8$ are independently selected from H, straight chain, branched or cyclic alkyl, aralkyl, aryl heteroaryl, acyl (RC—) and imidoyl (RC(NH)— or RC(NR')—) groups.

In one subembodiment of Formula II, Y and Z are each hydrogen. Alternatively, W and X are each hydrogen. In yet another subembodiment, W, X, Y and Z are all hydrogen.

In a subembodiment, the invention provides a compound of Formula II-1 to II-18, or a pharmaceutically acceptable salt, ester or prodrug thereof:

(II-1)

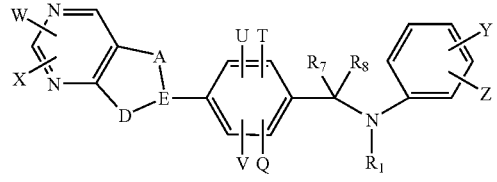

(II-2)

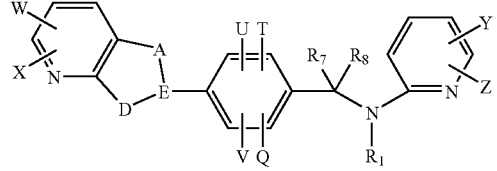

(II-3)

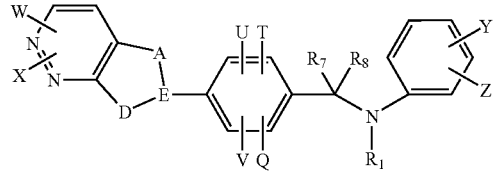

(II-4)

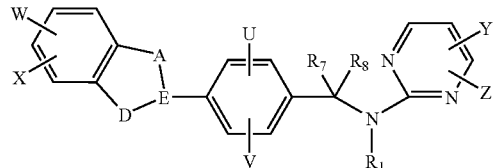

(II-5)

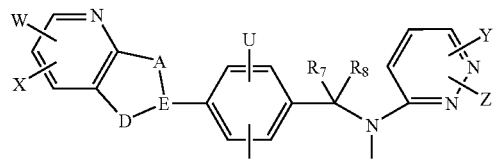

(II-6)

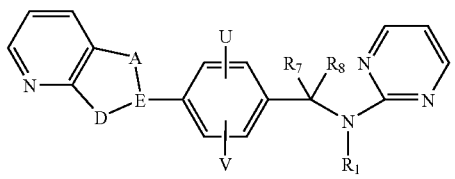

(II-7)

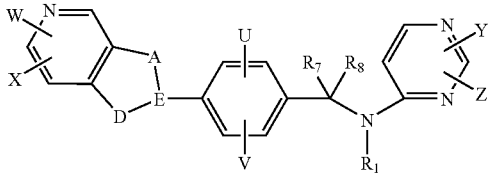

(II-8)

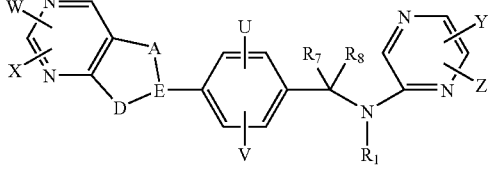

(II-9)

(II-10)

(II-11)

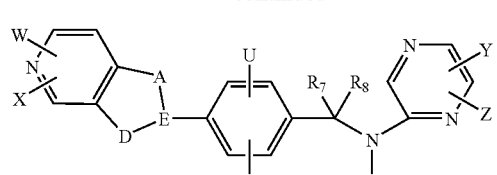
(II-12)
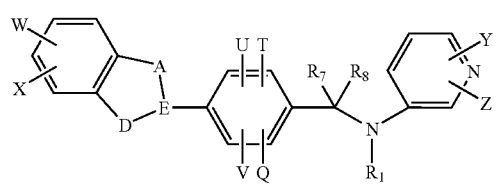
(II-13)
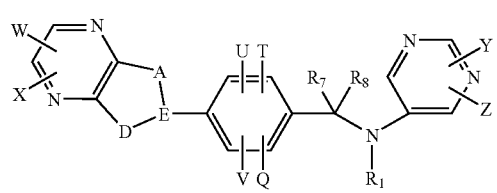
(II-14)
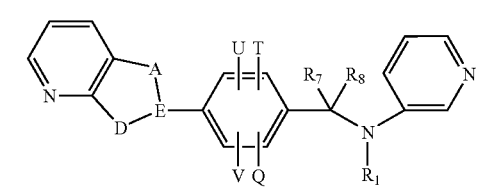
(II-15)
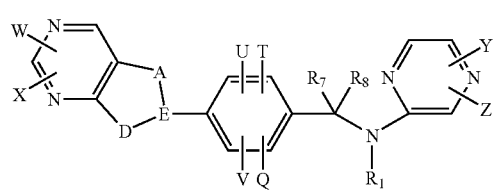
(II-16)
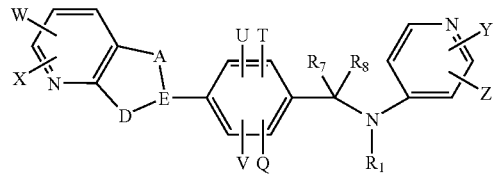
(II-17)
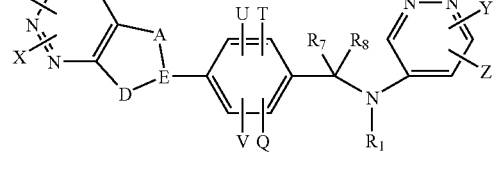
(II-18)
wherein
Q, T, U, V, W, X, Y and Z are as defined above;
A and -D-E- are as defined above; and
$R_1$, $R_2$, $R_3$, $R_4$, $R_5$, $R_6$, $R_7$ and $R_8$ are as defined above.
In another subembodiment, the invention provides a compound of Formula II-19 through II-30, or a pharmaceutically acceptable salt, ester or prodrug thereof:
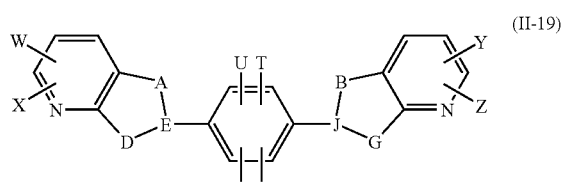
(II-19)
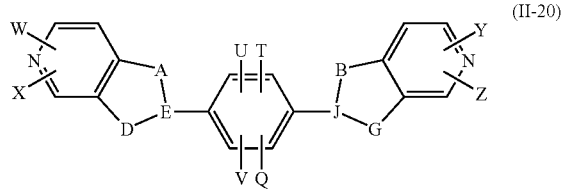
(II-20)
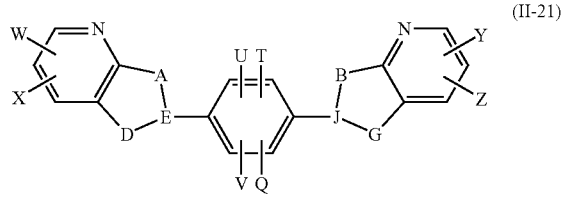
(II-21)
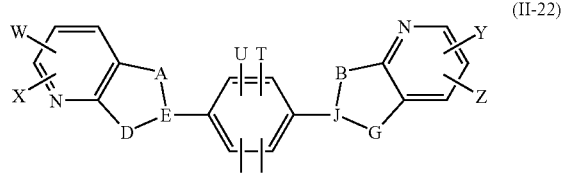
(II-22)
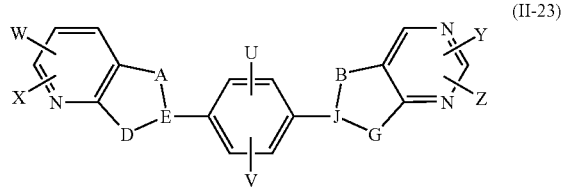
(II-23)
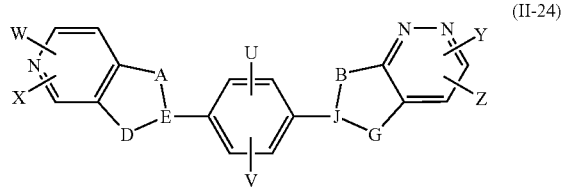
(II-24)
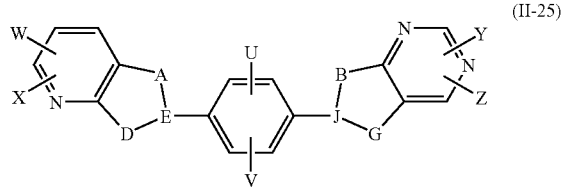
(II-25)
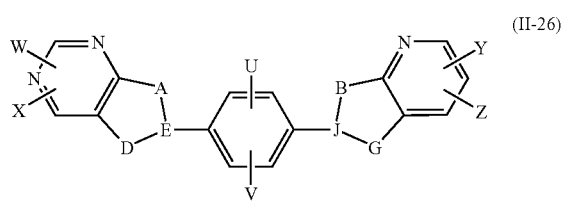
(II-26)

-continued

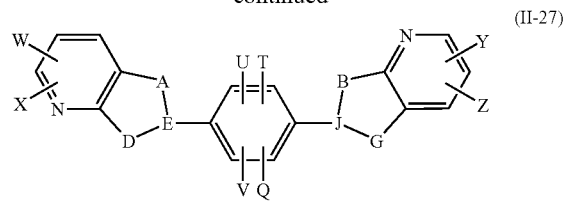
(II-27)

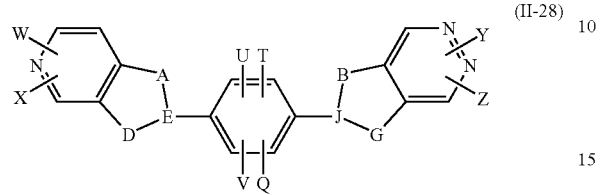
(II-28)

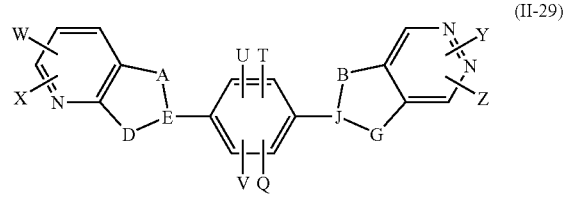
(II-29)

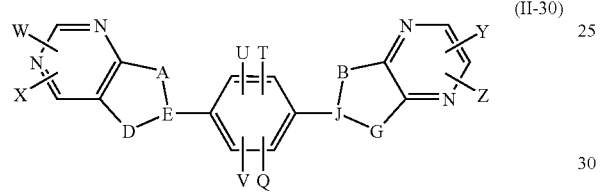
(II-30)

wherein
Q, T, U, V, W, X, Y and Z are as defined above;
A, B, -D-E- and -G-J- are as defined above; and
$R_1$, $R_2$, $R_3$, $R_4$, $R_5$, $R_6$, $R_7$ and $R_8$ are as defined above.

In another embodiment, a compound of Formula III, or a pharmaceutically acceptable salt, ester or prodrug thereof, is provided for the treatment or prevention of HIV infection, or for reduction of symptoms associated with AIDS, in a host in need thereof:

Formula III

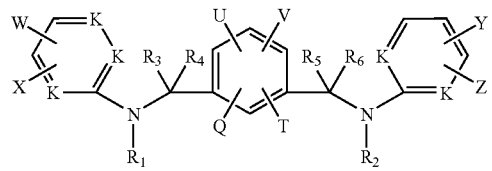

wherein
each K is independently N or CH;
Q, T, U, V, W, X, Y and Z are as defined above; and
$R_1$, $R_2$, $R_3$, $R_4$, $R_5$ and $R_6$ are as defined above.

In one subembodiment of Formula III, Y and Z are each hydrogen. Alternatively, W and X are each hydrogen. In yet another subembodiment, W, X, Y and Z are all hydrogen.

Reyes et al. (Reyes, et al. (2002) *Tetrahedron* 58:8573-8579) described the synthesis of certain polyamines from starting pyridinium N-aminides.

In a subembodiment, a compound of Formula III-1 through III-10, or a pharmaceutically acceptable salt, ester or prodrug thereof, is provided:

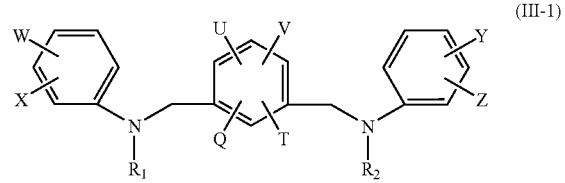
(III-1)

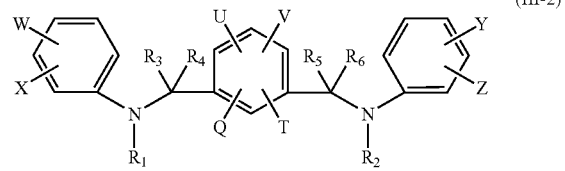
(III-2)

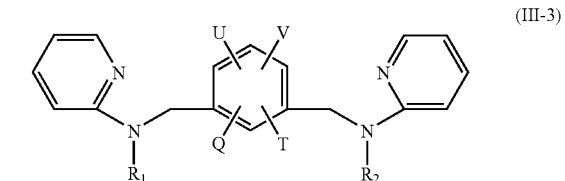
(III-3)

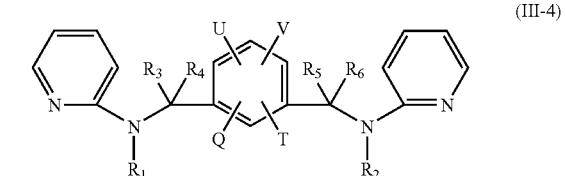
(III-4)

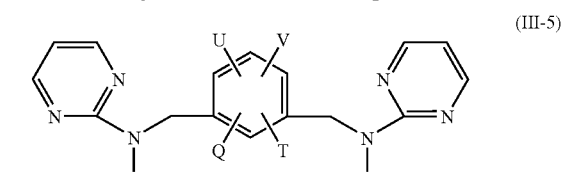
(III-5)

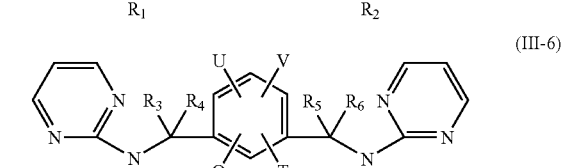
(III-6)

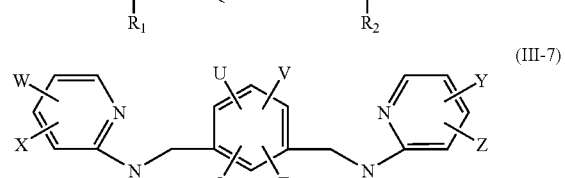
(III-7)

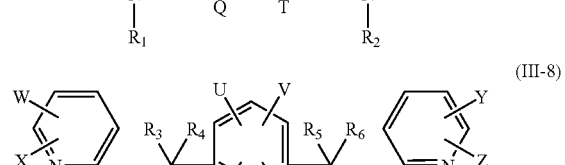
(III-8)

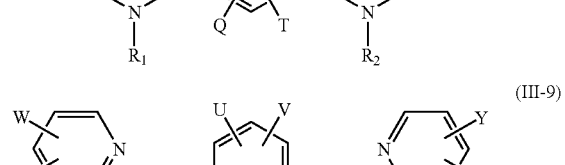
(III-9)

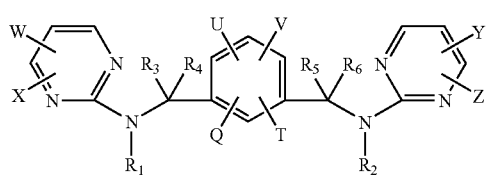
(III-10)

wherein
Q, T, U, V, W, X, Y and Z are as defined above; and
$R_1, R_2, R_3, R_4, R_5$ and $R_6$ are as defined above.

In another subembodiment, a compound of Formula III-11 through III-20, or a pharmaceutically acceptable salt, ester or prodrug thereof, is provided

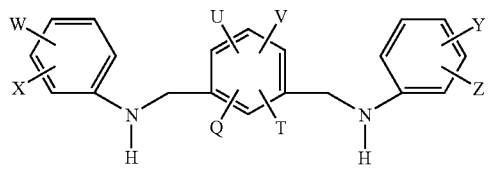
(III-11)

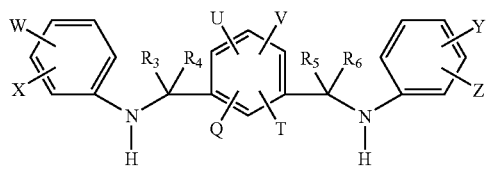
(III-12)

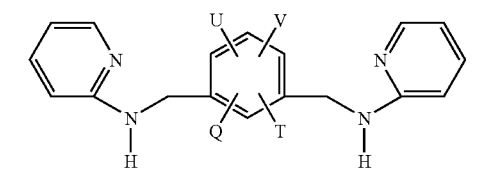
(III-13)

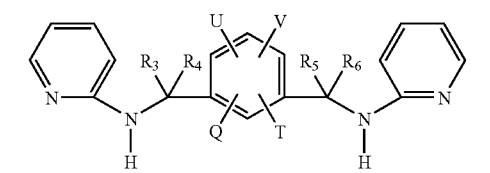
(III-14)

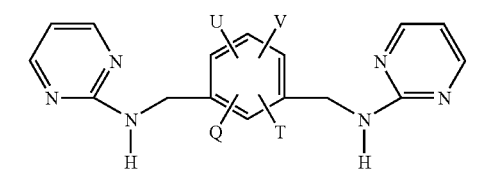
(III-15)

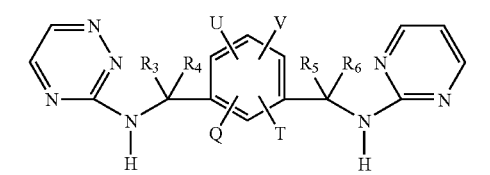
(III-16)

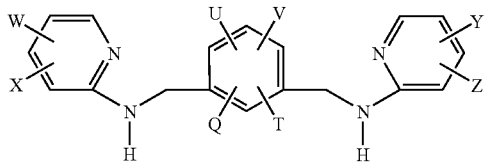
(III-17)

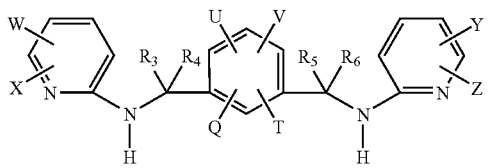
(III-18)

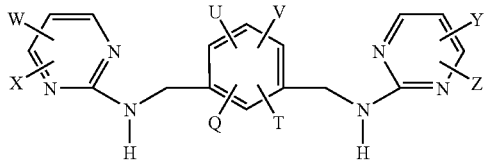
(III-19)

(III-20)

wherein
Q, T, U, V, W, X, Y and Z are as defined above; and
$R_1, R_2, R_3, R_4, R_5$ and $R_6$ are as defined above.

In another embodiment, the invention provides a compound of Formula IVa or IVb, or a pharmaceutically acceptable salt, ester or prodrug thereof:

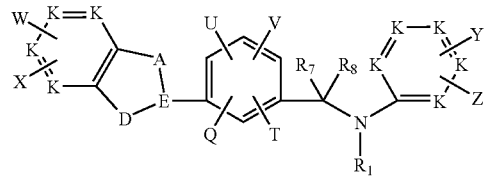
Formula IVa

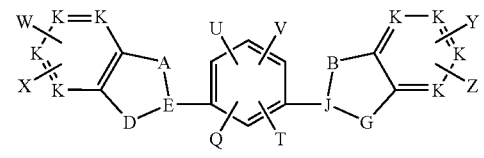
Formula IVb wherein
each K is independently N or CH;
Q, T, U, V, W, X, Y and Z are as defined above;
$R_1, R_2, R_3, R_4, R_5, R_6, R_7$ and $R_8$ are as defined above; and
A and B and -D-E- and -G-J- are as defined above.

In one subembodiment of Formula IVa or IVb, Y and Z are each hydrogen. Alternatively, W and X are each hydrogen. In yet another subembodiment, W, X, Y and Z are all hydrogen.

In one subembodiment, the invention provides a compound of Formula IV-1 to IV-12, or a pharmaceutically acceptable salt, ester or prodrug thereof:

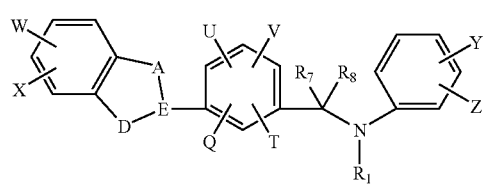
(IV-1)
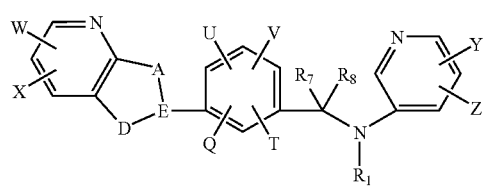
(IV-2)
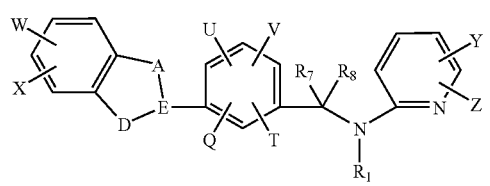
(IV-3)
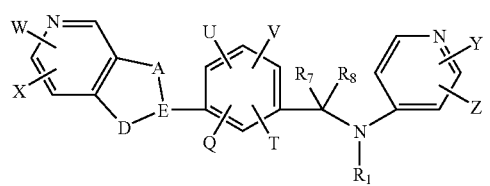
(IV-4)
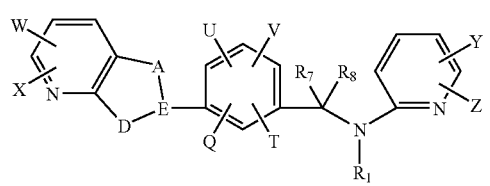
(IV-5)
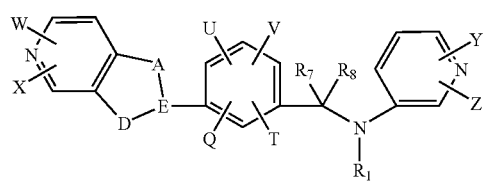
(IV-6)
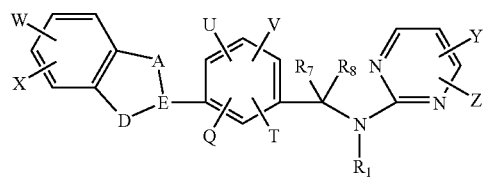
(IV-7)
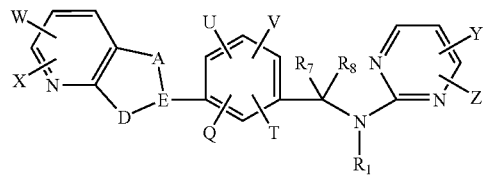
(IV-8)
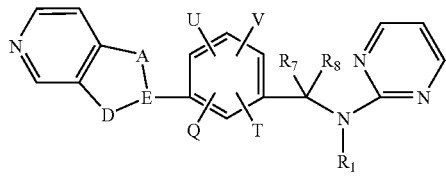
(IV-9)
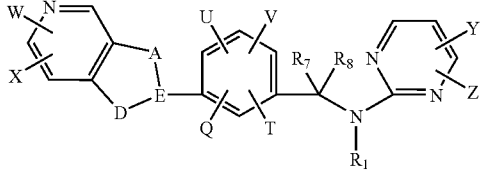
(IV-10)
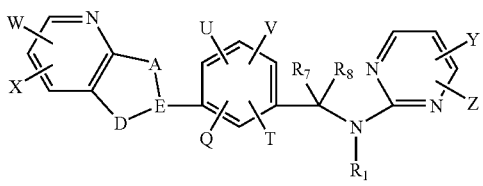
(IV-11)
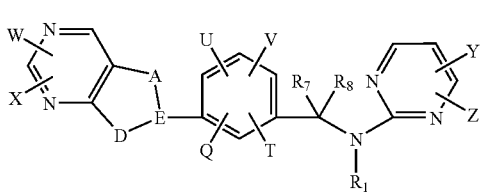
(IV-12)
wherein
Q, T, U, V, W, X, Y and Z are as defined above;
$R_1$, $R_2$, $R_3$, $R_4$, $R_5$, $R_6$, $R_7$ and $R_8$ are as defined above; and
A and -D-E- are as defined above.
In another subembodiment, compounds of the Formula IV-13 to IV-20, or a pharmaceutically acceptable salt, ester or prodrug thereof, are provided:
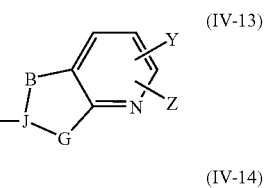
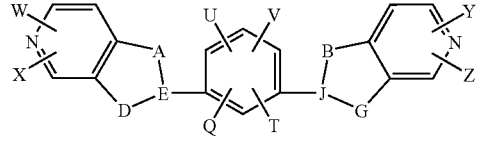
(IV-13)
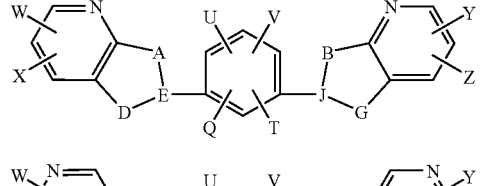
(IV-14)
(IV-15)
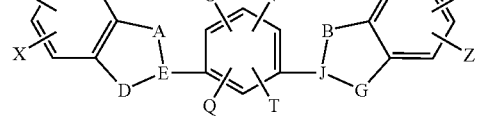
(IV-16)

-continued

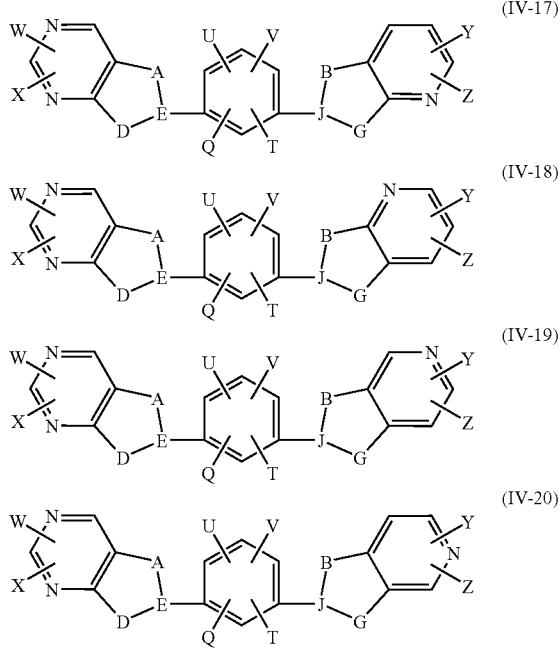

(IV-17)
(IV-18)
(IV-19)
(IV-20)

wherein
Q, T, U, V, W, X, Y and Z are as defined above;
$R_1$, $R_2$, $R_3$, $R_4$, $R_5$, $R_6$, $R_7$ and $R_8$ are as defined above; and
A, B, -D-E- and -G-J- are as defined above.

In another embodiment, a compound of Formula Va, Vb, or Vc or a pharmaceutically acceptable salt, ester or prodrug thereof, is provided for the treatment or prevention of HIV infection, or for reduction of symptoms associated with AIDS, in a host in need thereof:

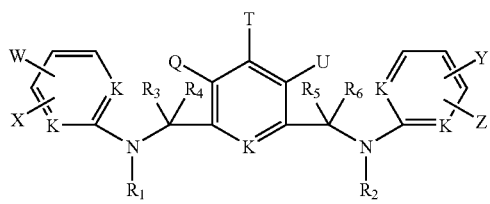

Formula Va

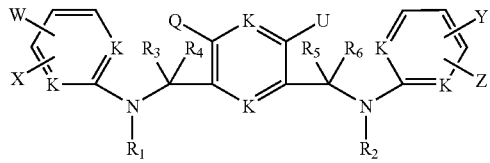

Formula Vb

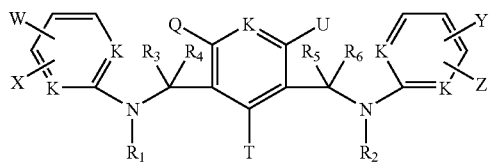

Formula Vc wherein
each K is independently N or CH;
Q, T, U, W, X, Y and Z are as defined above; and
$R_1$, $R_2$, $R_3$, $R_4$, $R_5$ and $R_6$ are as defined above.

In one subembodiment of Formula Va-c, Y and Z are each hydrogen. Alternatively, W and X are each hydrogen. In yet another subembodiment, W, X, Y and Z are all hydrogen.

In one subembodiment, a compound of Formula V-1 through V-3, or a pharmaceutically acceptable salt, ester or prodrug thereof, is provided:

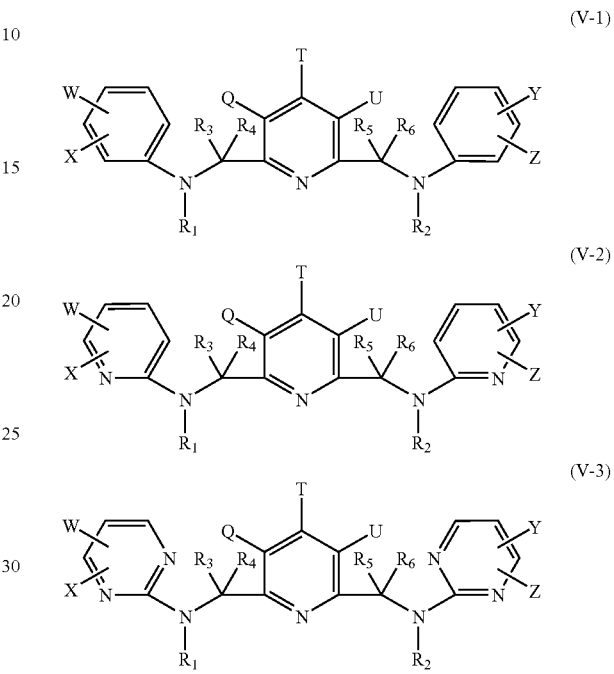

(V-1)
(V-2)
(V-3)

wherein
each K is independently N or CH;
Q, T, U, W, X, Y and Z are as defined above; and
$R_1$, $R_2$, $R_3$, $R_4$, $R_5$ and $R_6$ are as defined above.

In another subembodiment, a compound of Formula V-4 through V-9, or a pharmaceutically acceptable salt, ester or prodrug thereof, is provided:

(V-4)
(V-5)
(V-6)

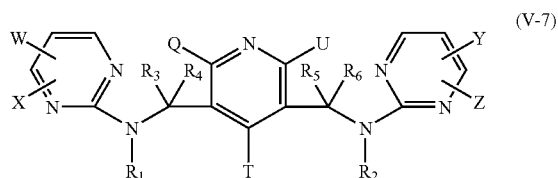
(V-7)

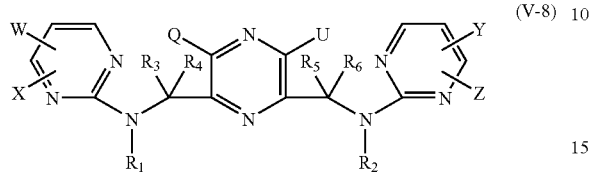
(V-8)

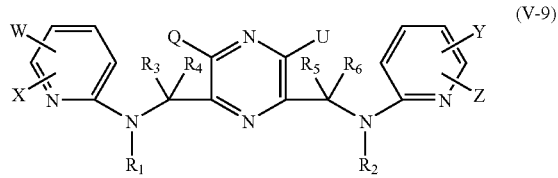
(V-9)

wherein each K is independently N or CH;

Q, T, U, W, X, Y and Z are as defined above; and $R_1$, $R_2$, $R_3$, $R_4$, $R_5$ and $R_6$ are as defined above.

In another embodiment, the invention provides a compound of Formula VIa or VIb, or a pharmaceutically acceptable salt, ester or prodrug thereof:

Formula VIa

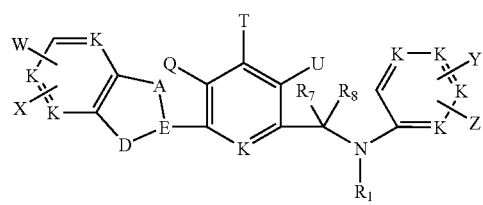

Formula VIb

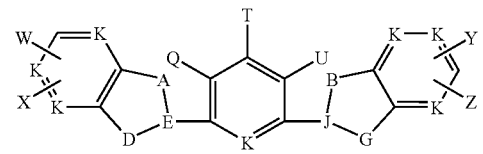

wherein each K is independently N or CH;

Q, T, U, W, X, Y and Z are as defined above;

$R_1$, $R_2$, $R_3$, $R_4$, $R_5$, $R_6$, $R_7$ and $R_8$ are as defined above; and A and B and -D-E- and -G-J- are as defined above.

In one subembodiment of Formula VIa or b, Y and Z are each hydrogen. Alternatively, W and X are each hydrogen. In yet another subembodiment, W, X, Y and Z are all hydrogen.

In one subembodiment, a compound of Formula VI-1 to VI-6, or a pharmaceutically acceptable salt, ester or prodrug thereof, is provided:

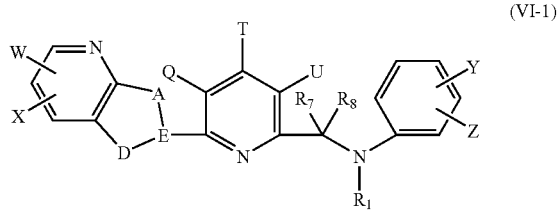
(VI-1)

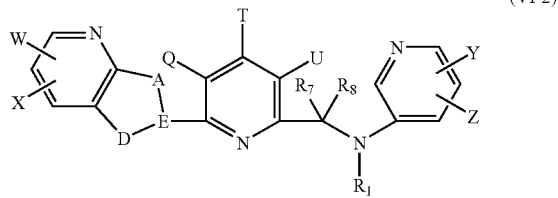
(VI-2)

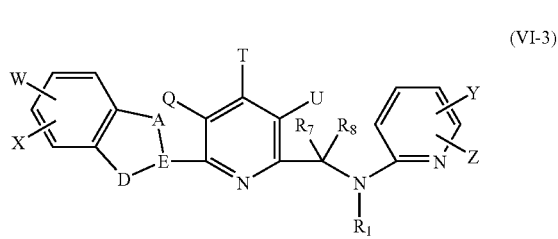
(VI-3)

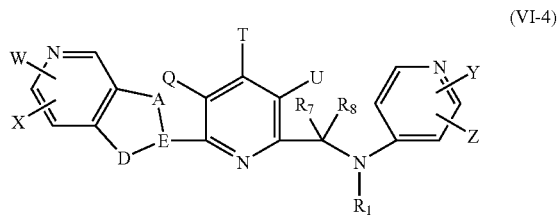
(VI-4)

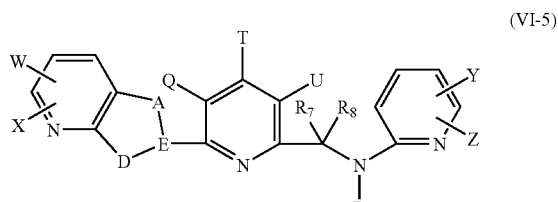
(VI-5)

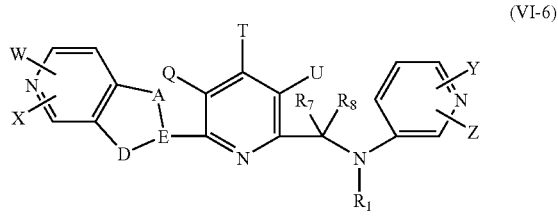
(VI-6)

wherein

Q, T, U, W, X, Y and Z are as defined above;

$R_1$, $R_2$, $R_3$, $R_4$, $R_5$, $R_6$, $R_7$ and $R_8$ are as defined above; and A and -D-E- are as defined above.

In another subembodiment, a compound of Formula VI-7 to VI-10, or a pharmaceutically acceptable salt, ester or prodrug thereof, is provided:

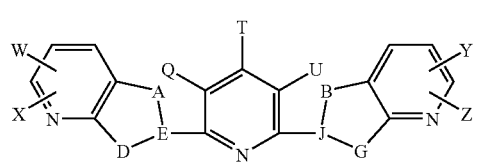
(VI-7)

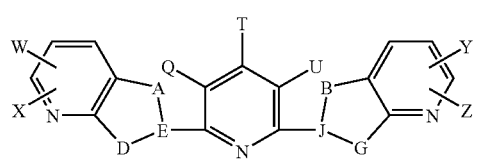
(VI-8)

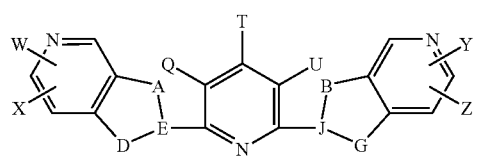
(VI-9)

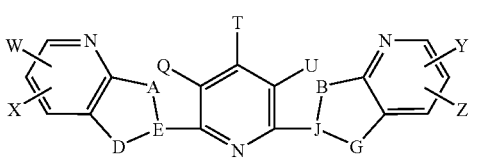
(VI-10)

wherein
Q, T, U, W, X, Y and Z are as defined above;
$R_1$, $R_2$, $R_3$, $R_4$, $R_5$, $R_6$, $R_7$ and $R_8$ are as defined above; and
A and B and -D-E- and -G-J- are as defined above.

In another embodiment, a compound of Formula VII, or a pharmaceutically acceptable salt, ester or prodrug thereof is provided for the treatment or prevention of HIV infection, or for reduction of symptoms associated with AIDS, in a host in need thereof:

Formula VII

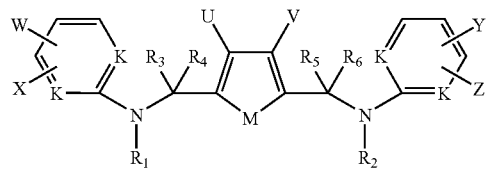

wherein
each K is independently N or CH;
U, V, W, X, Y and Z are as defined above;
$R_1$, $R_2$, $R_3$, $R_4$, $R_5$ and $R_6$ are as defined above; and
M is O, S or $NR_3$.

In one subembodiment of Formula VII, Y and Z are each hydrogen. Alternatively, W and X are each hydrogen. In yet another subembodiment, W, X, Y and Z are all hydrogen.

In one subembodiment, a compound of Formula VII-1 to VII-10, or a pharmaceutically acceptable salt, ester or prodrug thereof, is provided:

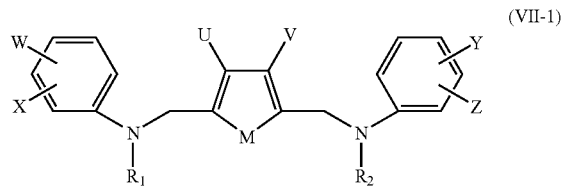
(VII-1)

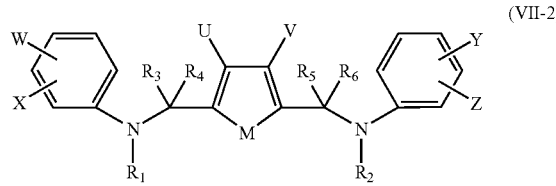
(VII-2)

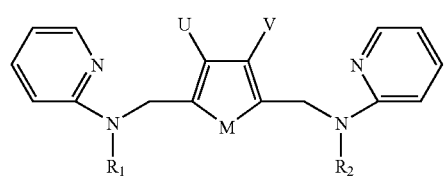
(VII-3)

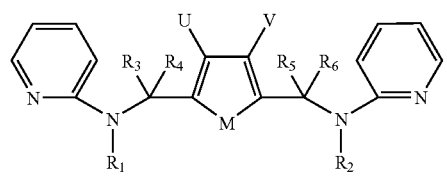
(VII-4)

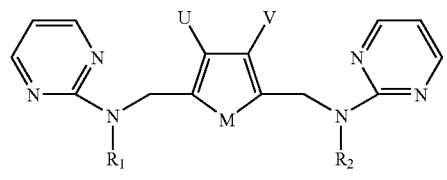
(VII-5)

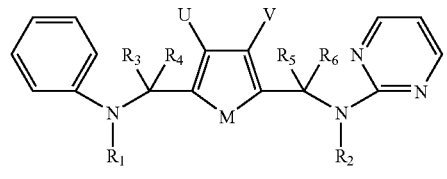
(VII-6)

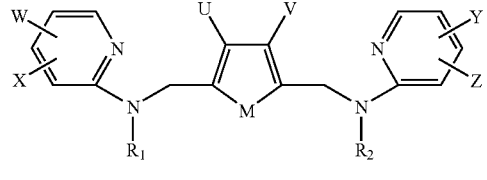
(VII-7)

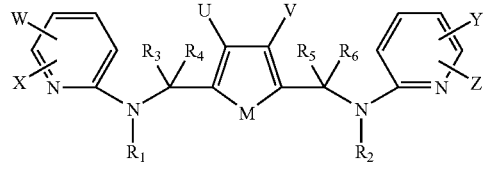
(VII-8)

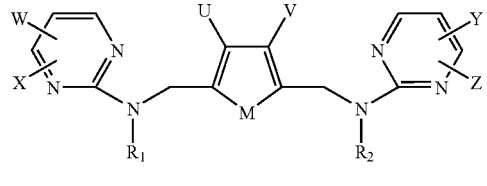
(VII-9)

-continued (VII-10)
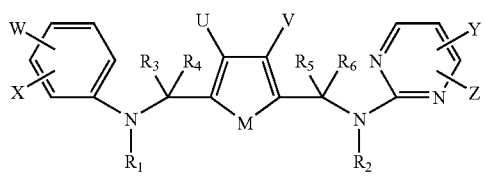

wherein
U, V, W, X, Y and Z are as defined above;
$R_1$, $R_2$, $R_3$, $R_4$, $R_5$ and $R_6$ are as defined above; and
M is O, S or $NR_3$.

In another subembodiment, a compound of Formula VII-11 to VII-20, or a pharmaceutically acceptable salt, ester or prodrug thereof, is provided:

(VII-11)
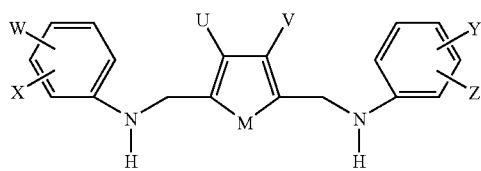

(VII-12)
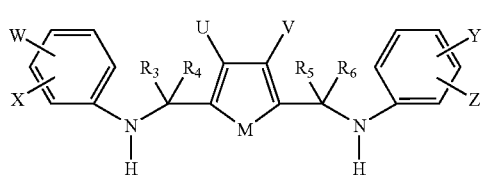

(VII-13)
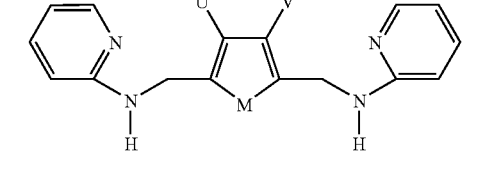

(VII-14)
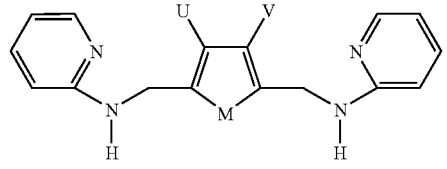

(VII-15)
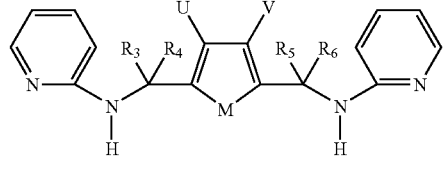

(VII-16)
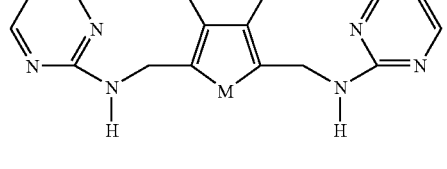

(VII-17)
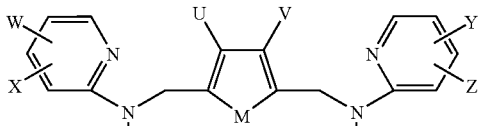

(VII-18)
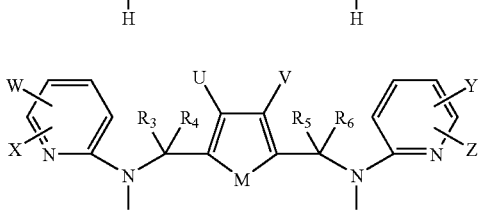

(VII-19)
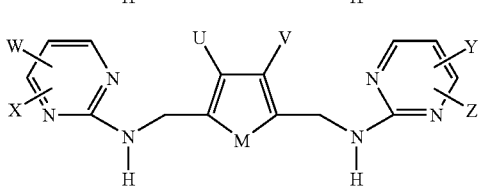

(VII-20)
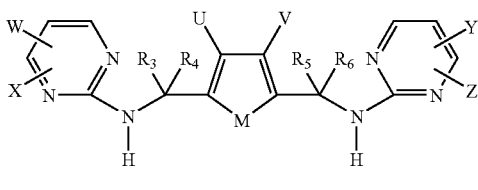

wherein
U, V, W, X, Y and Z are as defined above;
$R_1$, $R_2$, $R_3$, $R_4$, $R_5$ and $R_6$ are as defined above; and
M is O, S or $NR_3$.

In another embodiment, the invention provides a compound of Formula VIIIa or VIIIb, or a pharmaceutically acceptable salt, ester or prodrug thereof:

Formula VIIIa
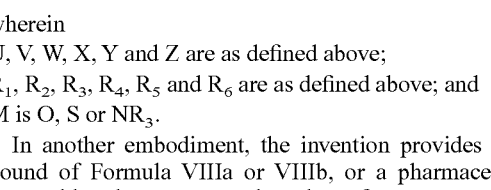

Formula VIIIb
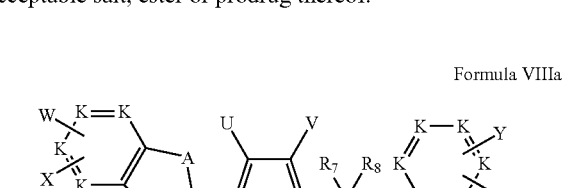

wherein
each K is independently N or CH;
U, V, W, X, Y and Z are as defined above;
$R_1$, $R_2$, $R_3$, $R_4$, $R_5$, $R_6$, $R_7$ and $R_8$ are as defined above; and
A and B and -D-E- and -G-J- are as defined above; and
M is O, S or $NR_3$.

In one subembodiment of Formula VIIIa or b, Y and Z are each hydrogen. Alternatively, W and X are each hydrogen. In yet another subembodiment, W, X, Y and Z are all hydrogen.

In a subembodiment, a compound of Formula VIII-1 to VIII-12, or a pharmaceutically acceptable salt, ester or prodrug thereof, is provided:

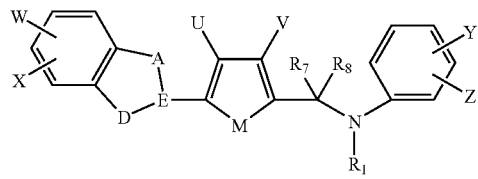
(VIII-1)

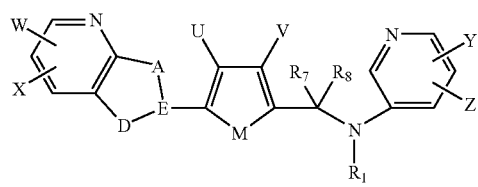
(VIII-2)

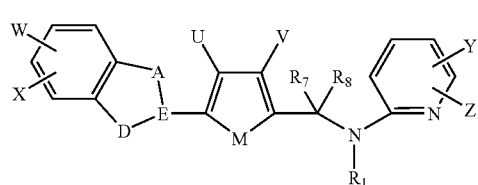
(VIII-3)

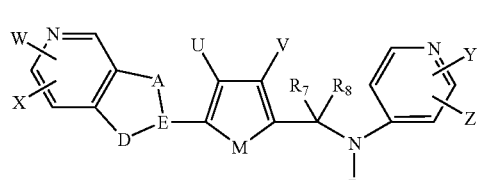
(VIII-4)

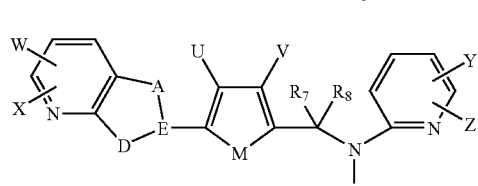
(VIII-5)

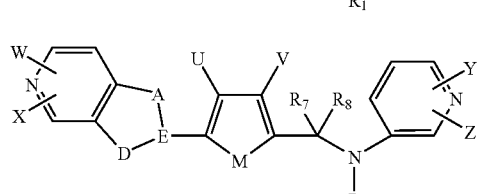
(VIII-6)

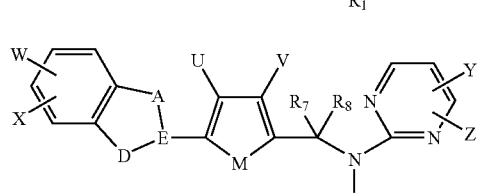
(VIII-7)

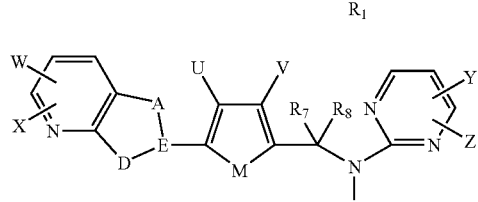
(VIII-8)

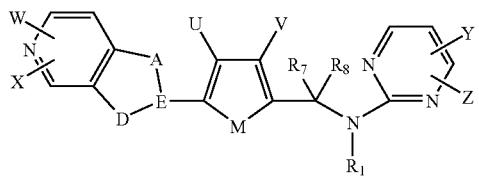
(VIII-9)

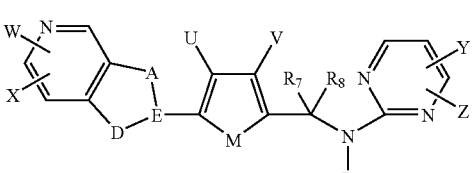
(VIII-10)

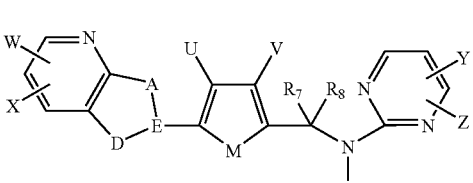
(VIII-11)

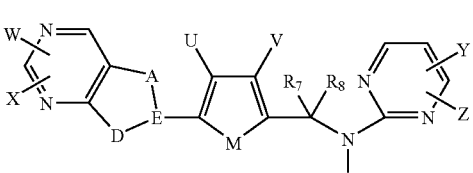
(VIII-12)

wherein

M, U, V, W, X, Y and Z are as defined above;

$R_1$, $R_2$, $R_3$, $R_4$, $R_5$, $R_6$, $R_7$ and $R_8$ are as defined above; and A and -D-E- are as defined above.

In another subembodiment, a compound of Formula VIII-13 to VIII-20, or a pharmaceutically acceptable salt, ester or prodrug thereof, is provided:

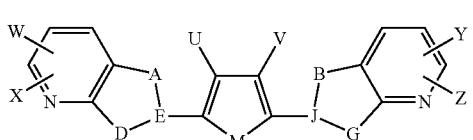
(VIII-13)

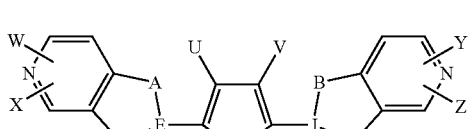
(VIII-14)

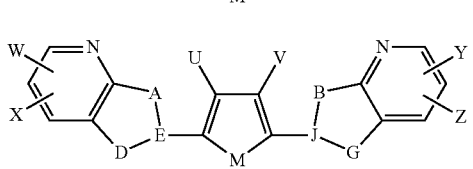
(VIII-15)

-continued

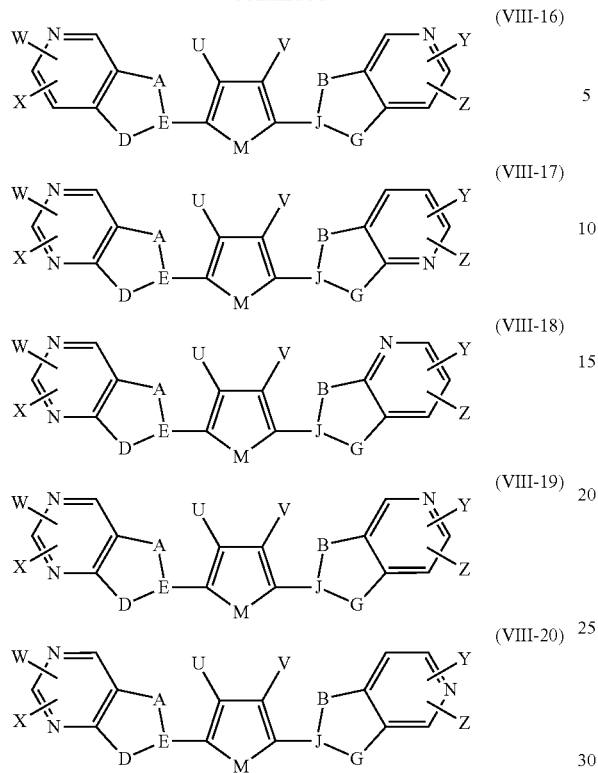

(VIII-16)
(VIII-17)
(VIII-18)
(VIII-19)
(VIII-20)

wherein
M, U, V, W, X, Y and Z are as defined above;
$R_1$, $R_2$, $R_3$, $R_4$, $R_5$, $R_6$, $R_7$ and $R_8$ are as defined above; and
A, B, -D-E- and -G-J- are as defined above.

In another embodiment, the invention provides a compound of Formula IX, or a pharmaceutically acceptable salt, ester or prodrug thereof.

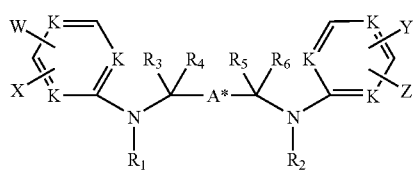

Formula IX wherein
each K is independently N or CH;
W, X, Y and Z are as defined above;
$R_1$, $R_2$, $R_3$, $R_4$, $R_5$ and $R_6$ are as defined above;
A* is independently selected from the group consisting of formulas a-g:

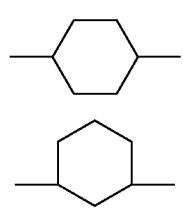

(a)

(b)

-continued

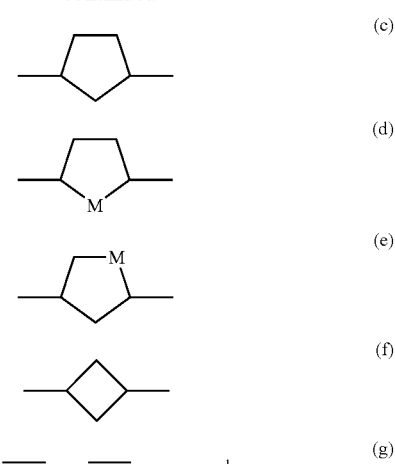

(c)
(d)
(e)
(f)
(g)

and
M is O, S or $NR_3$.

In one subembodiment, a compound of Formula IX-1 to IX-12 is provided, or a pharmaceutically acceptable salt, ester or prodrug thereof:

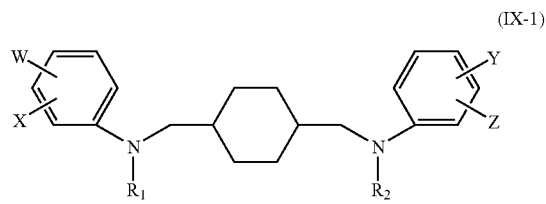

(IX-1)

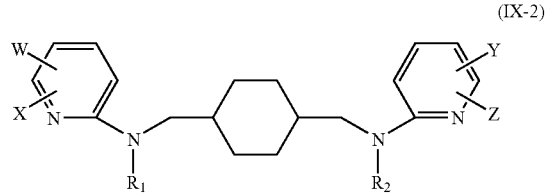

(IX-2)

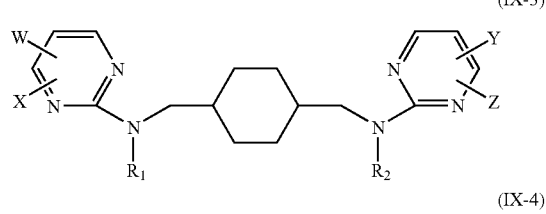

(IX-3)

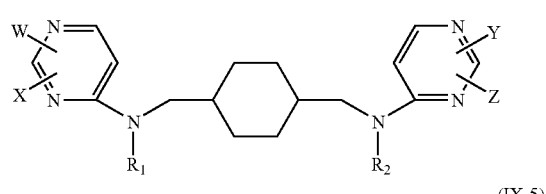

(IX-4)

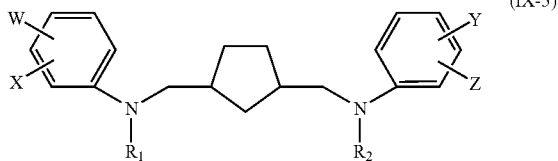

(IX-5)

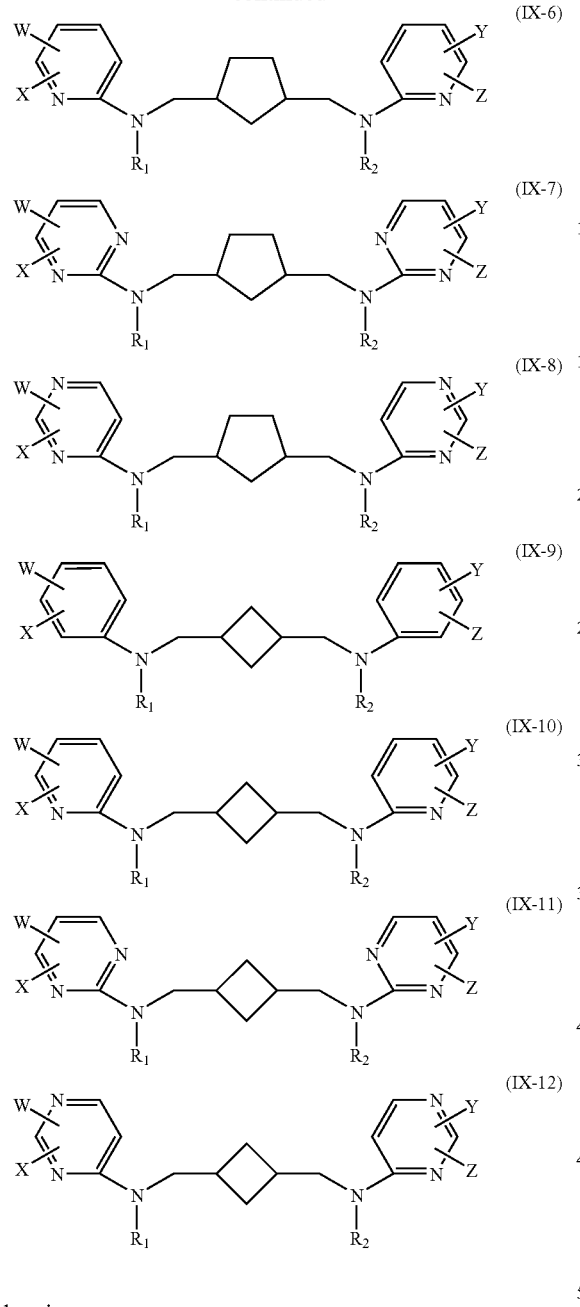
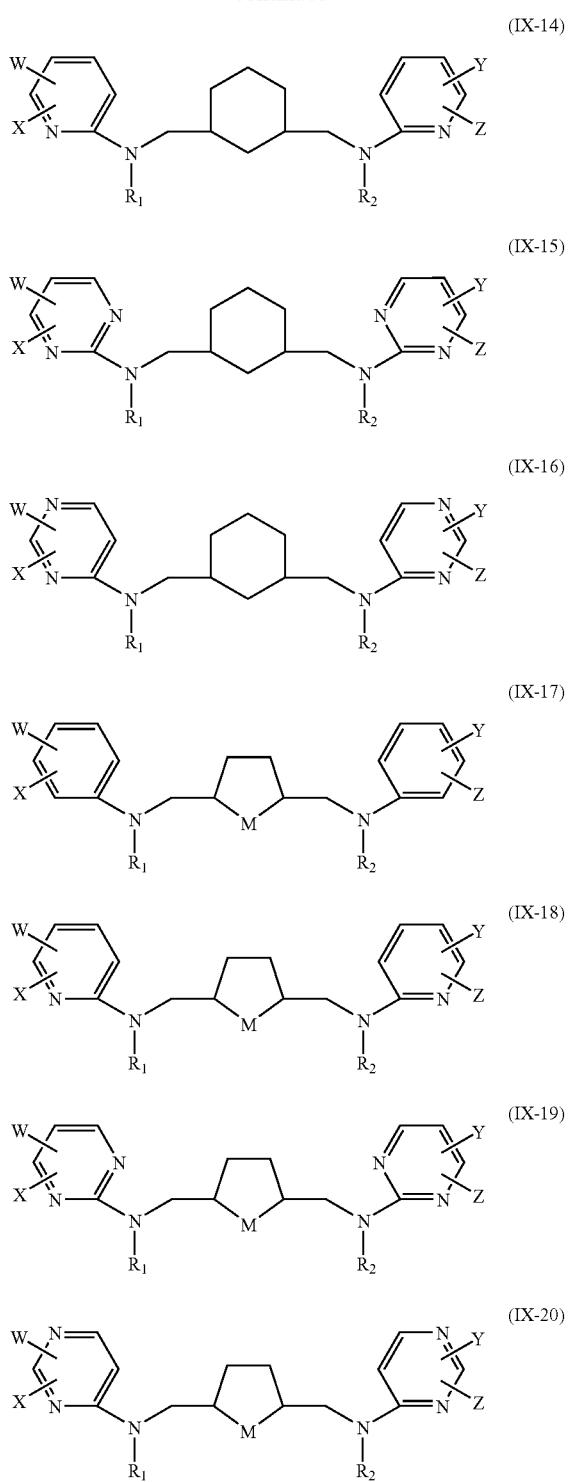
wherein
W, X, Y and Z are as defined above; and
$R_1$, $R_2$, $R_3$, $R_4$, $R_5$ and $R_6$ are as defined above.
In another subembodiment, a compound of Formula IX-13 to IX-24 is provided, or a pharmaceutically acceptable salt, ester or prodrug thereof:
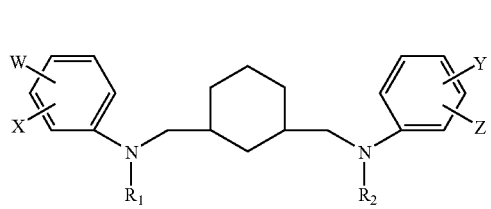
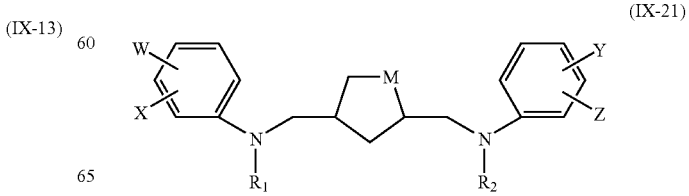

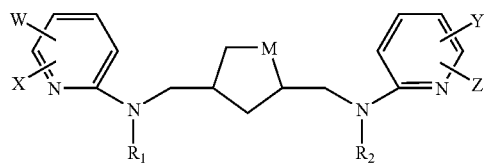 (IX-22)

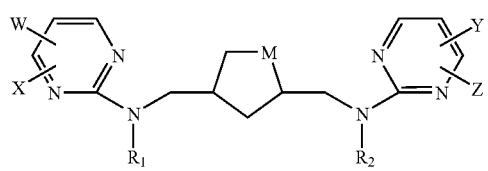 (IX-23)

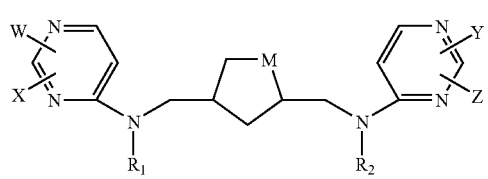 (IX-24)

wherein

M, W, X, Y and Z are as defined above; and $R_1$, $R_2$, $R_3$, $R_4$, $R_5$ and $R_6$ are as defined above.

In yet another subembodiment, a compound of Formula IX-25 to IX-36 is provided, or a pharmaceutically acceptable salt, ester or prodrug thereof:

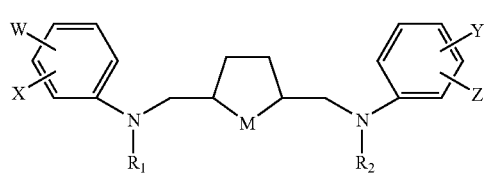 (IX-25)

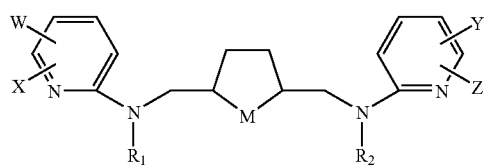 (IX-26)

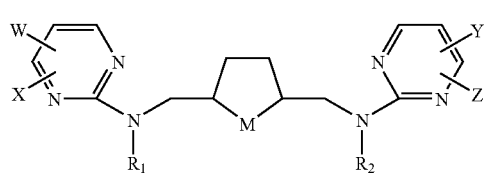 (IX-27)

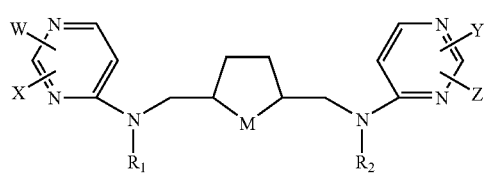 (IX-28)

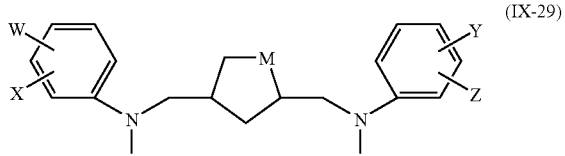 (IX-29)

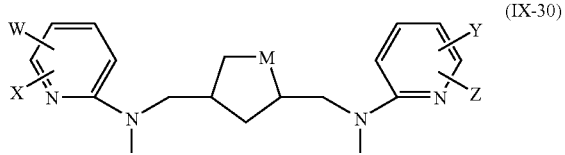 (IX-30)

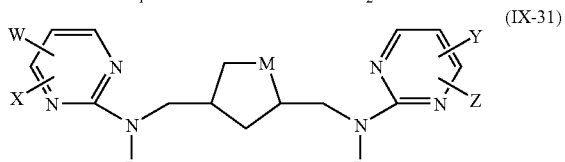 (IX-31)

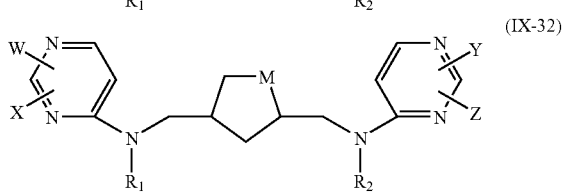 (IX-32)

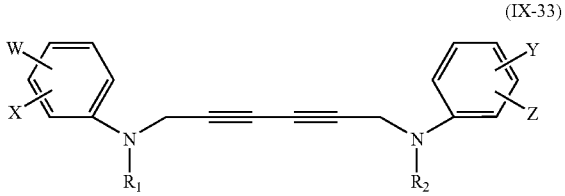 (IX-33)

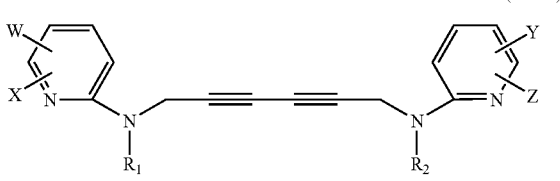 (IX-34)

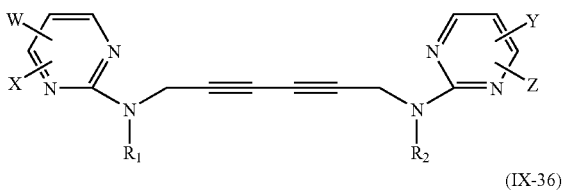 (IX-35)

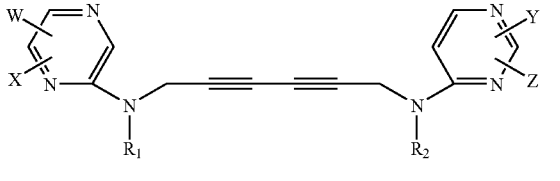 (IX-36)

wherein

M, W, X, Y and Z are as defined above; and $R_1$, $R_2$, $R_3$, $R_4$, $R_5$ and $R_6$ are as defined above.

In another embodiment, the invention provides a compound of Formula X, or a pharmaceutically acceptable salt, ester or prodrug thereof:

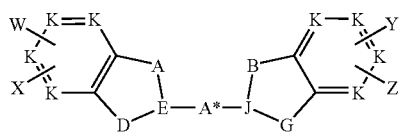

Formula X wherein
each K is independently N or CH;
W, X, Y and Z are as defined above;
R$_1$, R$_2$, R$_3$, R$_4$, R$_5$, R$_6$, R$_7$ and R$_8$ are as defined above; and
A and B and -D-E- and -G-J- are as defined above; and
A* is as defined above; and
M is as defined above.

In one subembodiment, a compound of Formula X-1 to X-14 is provided, or a pharmaceutically acceptable salt, ester or prodrug thereof:

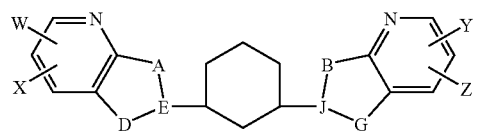
(X-1)

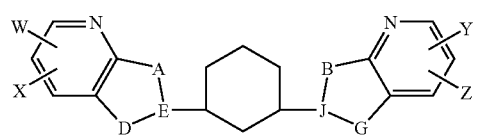
(X-2)

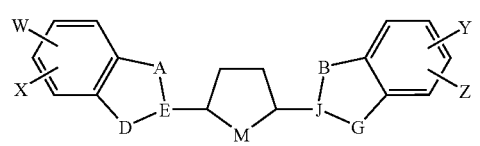
(X-3)

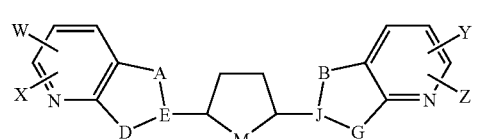
(X-4)

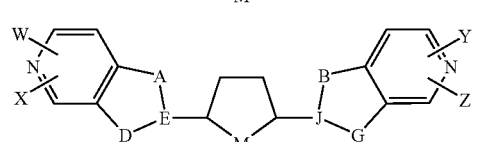
(X-5)

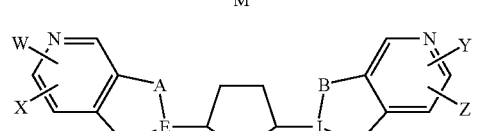
(X-6)

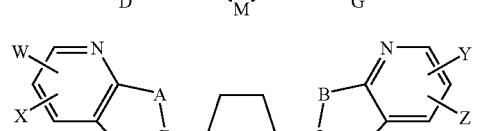
(X-7)

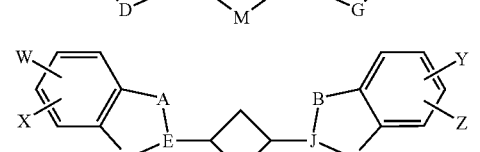
(X-8)

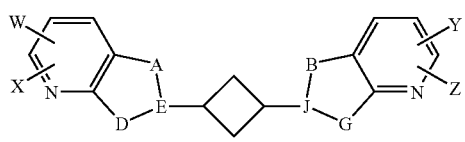
(X-9)

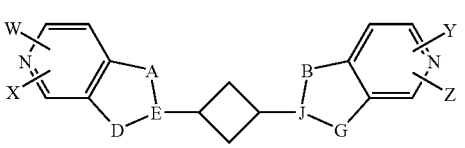
(X-10)

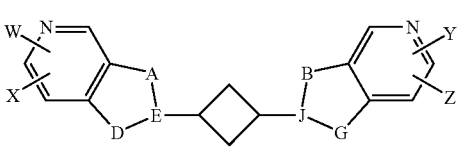
(X-11)

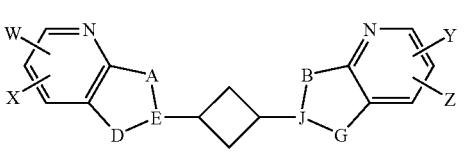
(X-12)

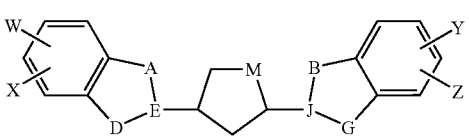
(X-13)

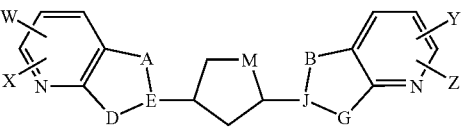
(X-14)

wherein
M, W, X, Y and Z are as defined above;
R$_1$, R$_2$, R$_3$, R$_4$, R$_5$, R$_6$, R$_7$ and R$_8$ are as defined above; and
A and B and -D-E- and -G-J- are as defined above.

In another subembodiment, a compound of Formula X-15 to X-28 is provided, or a pharmaceutically acceptable salt, ester or prodrug thereof:

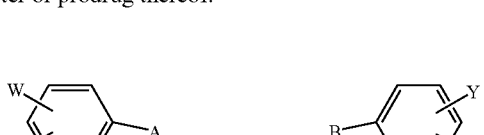
(X-15)

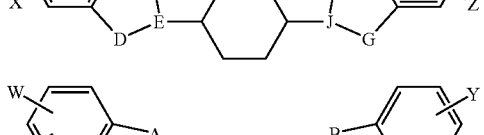
(X-16)

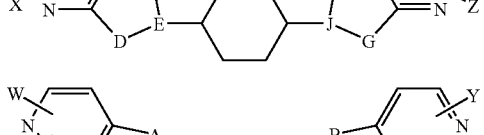
(X-17)

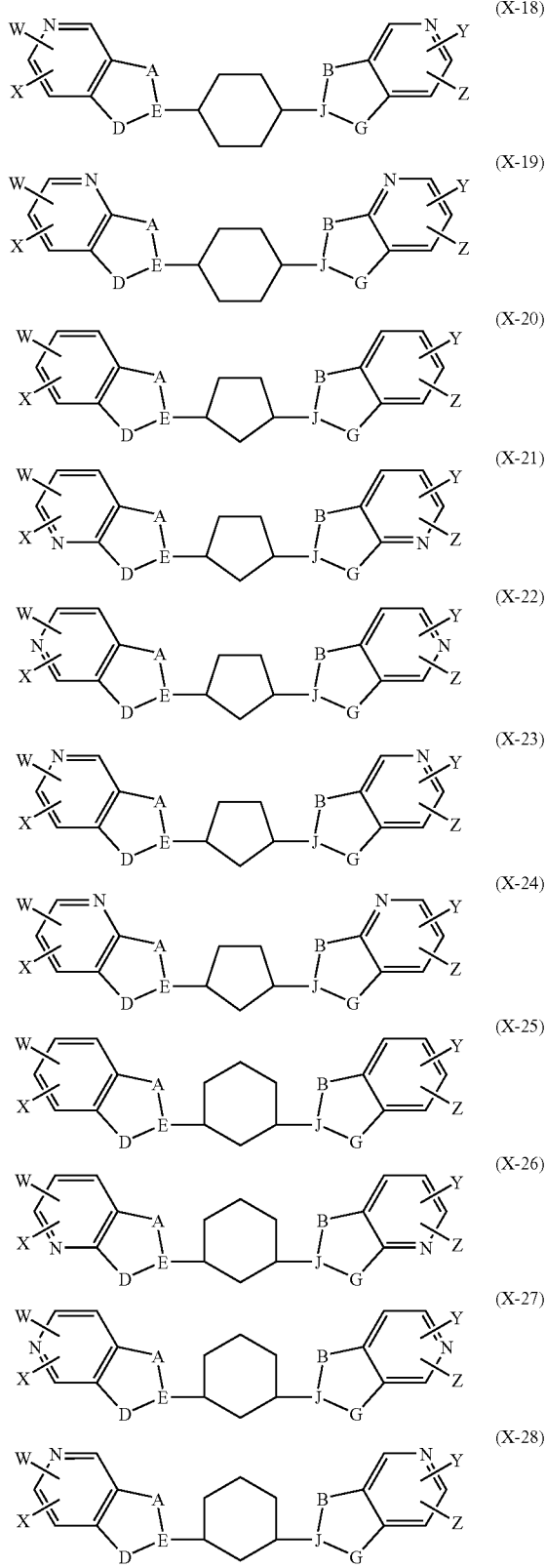

wherein
M, W, X, Y and Z are as defined above;
$R_1$, $R_2$, $R_3$, $R_4$, $R_5$, $R_6$, $R_7$ and $R_8$ are as defined above; and
A and B and -D-E- and -G-J- are as defined above.

In yet another subembodiment, a compound of Formula X-29 to X-38 is provided, or a pharmaceutically acceptable salt, ester or prodrug thereof:

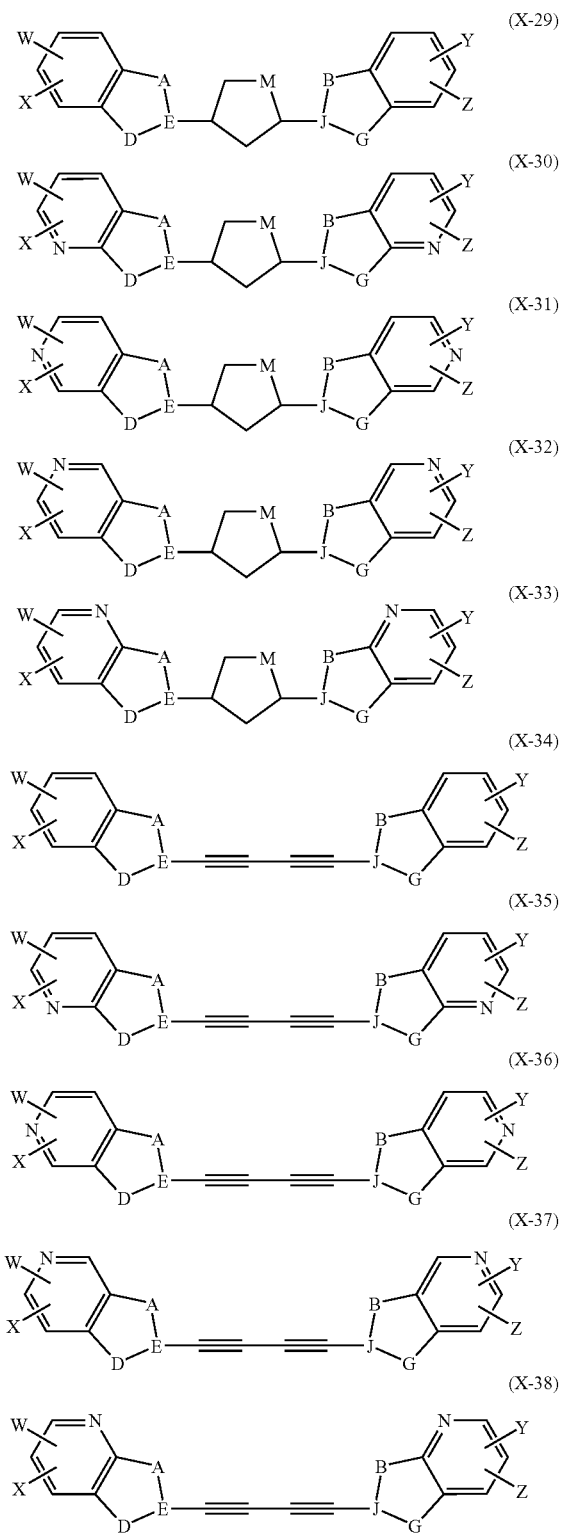

wherein
M, W, X, Y and Z are as defined above;
$R_1$, $R_2$, $R_3$, $R_4$, $R_5$, $R_6$, $R_7$ and $R_8$ are as defined above; and
A and B and -D-E- and -G-J- are as defined above.

In another embodiment, a compound of Formula XI, or a pharmaceutically acceptable salt, ester or prodrug thereof is provided for the treatment or prevention of HIV infection, or for reduction of symptoms associated with AIDS, in a host in need thereof:

Formula XI

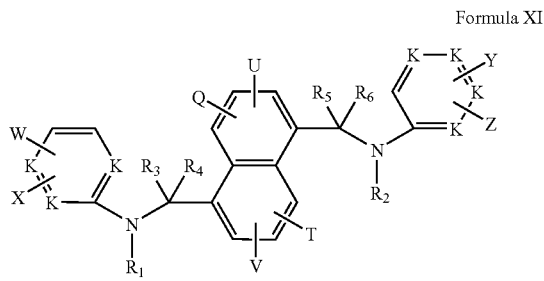

wherein
each K is independently N or CH;
Q, T, U, V, W, X, Y and Z are as defined above; and
$R_1, R_2, R_3, R_4, R_5$ and $R_6$ are as defined above.

In one subembodiment of Formula XI, Y and Z are each hydrogen. Alternatively, W and X are each hydrogen. In yet another subembodiment, W, X, Y and Z are all hydrogen.

In one subembodiment, a compound of Formula XI-1 to XI-6 is provided, or a pharmaceutically acceptable salt, ester or prodrug thereof:

(XI-1)

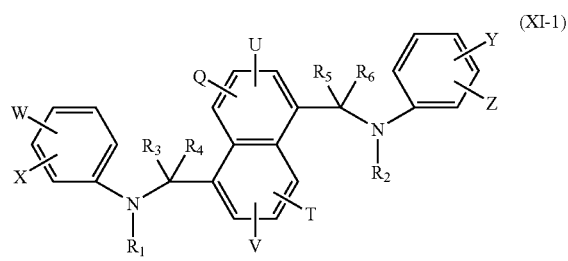

(XI-2)

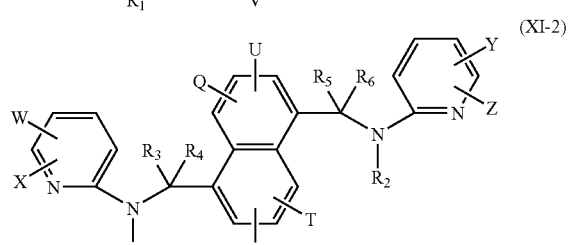

(XI-3)

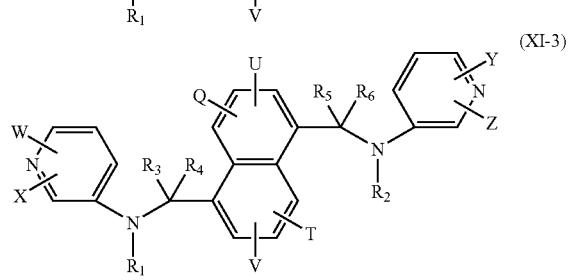

(XI-4)

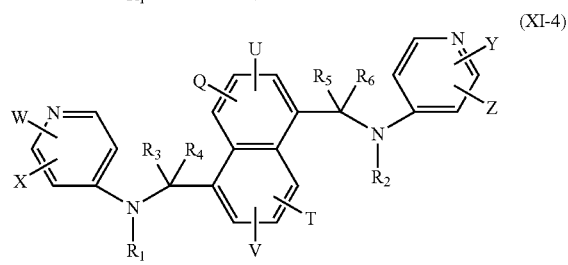

(XI-5)

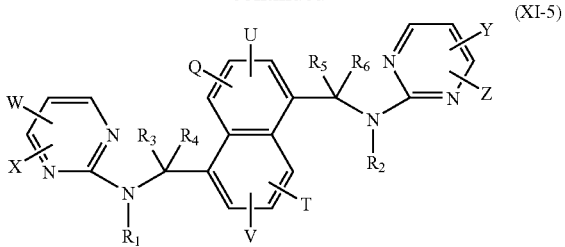

(XI-6)

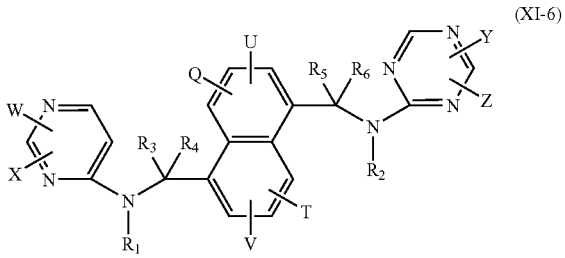

wherein
Q, T, U, V, W, X, Y and Z are as defined above; and
$R_1, R_2, R_3, R_4, R_5$ and $R_6$ are as defined above.

In another embodiment, a compound of Formula XII, or a pharmaceutically acceptable salt, ester or prodrug thereof, is provided for the treatment or prevention of HIV infection, or for reduction of symptoms associated with AIDS, in a host in need thereof:

Formula XII

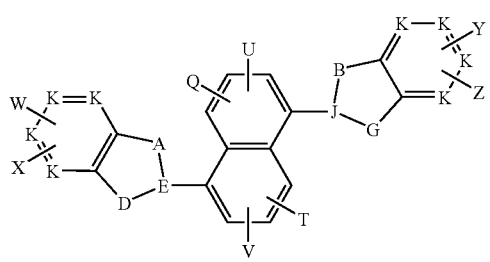

wherein
each K is independently N or CH;
Q, T, U, V, W, X, Y and Z are as defined above;
$R_1, R_2, R_3, R_4, R_5, R_6, R_7$ and $R_8$ are as defined above; and
A and B and -D-E- and -G-J- are as defined above.

In one subembodiment of Formula XII, Y and Z are each hydrogen. Alternatively, W and X are each hydrogen. In yet another subembodiment, W, X, Y and Z are all hydrogen.

In one subembodiment, a compound of Formula XII-1 to XII-5 is provided, or a pharmaceutically acceptable salt, ester or prodrug thereof:

(XII-1)

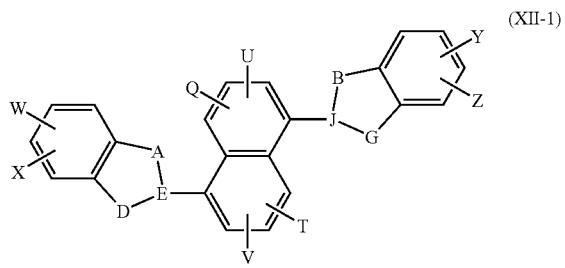

-continued

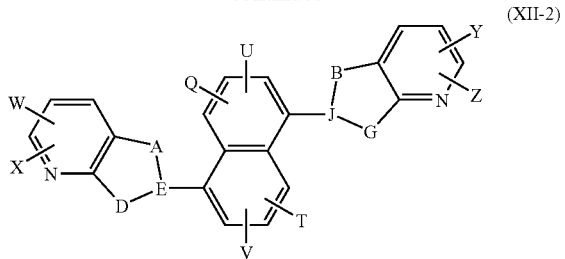
(XII-2)

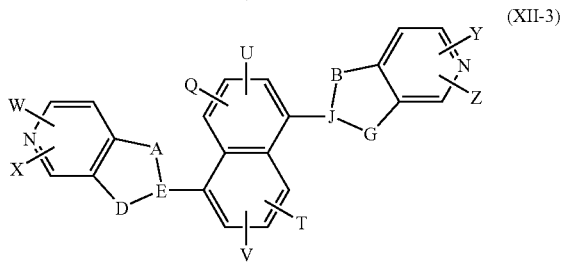
(XII-3)

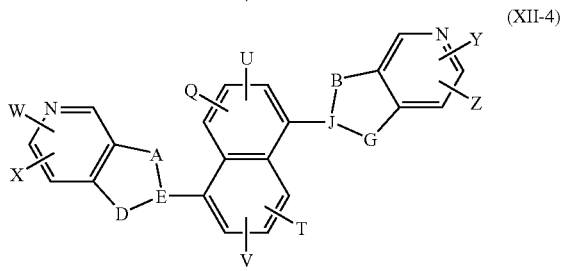
(XII-4)

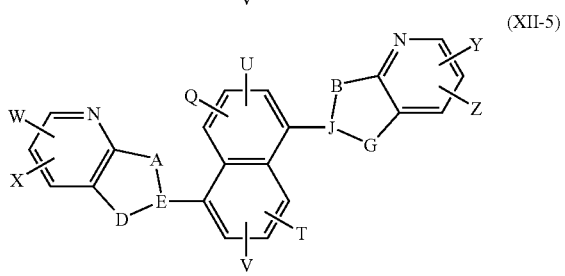
(XII-5)

wherein
Q, T, U, V, W, X, Y and Z are as defined above;
$R_1$, $R_2$, $R_3$, $R_4$, $R_5$, $R_6$, $R_7$ and $R_8$ are as defined above; and
A and B and -D-E- and -G-J- are as defined above.

In another embodiment, a method, compound and pharmaceutical composition for the treatment or prevention of HIV infection, or for reduction of symptoms associated with AIDS, in a host in need thereof is provided including a compound of Formula XIII, or a pharmaceutically acceptable salt, ester or prodrug thereof:

Formula XIII

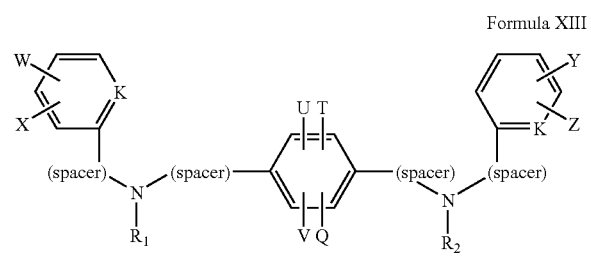

wherein
K, Q, T, U, V, W, X, Y and Z are as defined above;
$R_1$, $R_2$, $R_3$, $R_4$, $R_5$ and $R_6$ are as defined above; and "spacer" is independently a bond, straight chained or branched $C_1$-$C_5$ alkyl, $C_2$-$C_5$ alkenyl, $C_2$-$C_5$ alkynyl, $C_1$-$C_5$ alkoxy, $C_2$-$C_5$ alkenoxy, and $C_2$-$C_5$ alkynoxy wherein the alkyl group can be substituted by a heteroatom (such as N, O or S) for example —$CH_2$—$OCH_2$—, —$CH_2CH_2$—$OCH_2$—, —$CH_2CH_2$—$OCH_2CH_2$—, —$CH_2$—$OCH_2CH_2$-, —$CH_2CH_2$—$OCH_2CH_2CH_2$—, —$CH_2CH_2CH_2$—$OCH_2$—, —$CH_2CH_2CH_2$—$OCH_2CH_2$—, —$CH_2CH_2$—$OCH_2CH_2CH_2$—, —$(CH_2)_n$—$OH(CH_3)$—$(CH_2)_n$—, $CH_2$—$OH(CH_3)$—$O$—$CH_2$, —$(CH_2)n$-, —$(CH_2)n$-CO—, —$(CH_2)n$-N—, —$(CH_2)n$-O—, —$(CH_2)n$-S—, —$(CH_2O)$—, —$(OCH_2)$—, —$(SCH_2)$—, —$(CH_2S$—), -(aryl-O)—, —(O-aryl)-, -(alkyl-O)—, —(O-alkyl)- wherein n is independently 0, 1, 2, 3, 4, 5, 6, 7, 8, 9, or 10.

In another embodiment, a method, compound and pharmaceutical composition for the treatment or prevention of HIV infection, or for reduction of symptoms associated with AIDS, in a host in need thereof is provided including a compound of Formula XIVa or XIVb, or a pharmaceutically acceptable salt, ester or prodrug thereof:

Formula XIVa

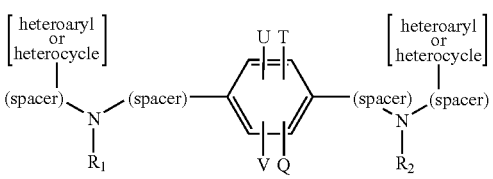

Formula XIVb

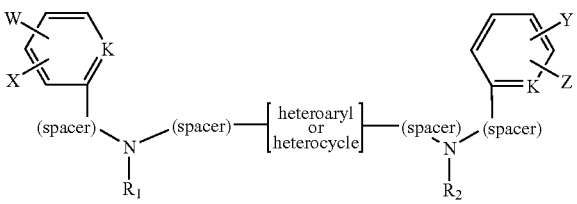

wherein
K, Q, T, U, V, W, X, Y and Z are as defined above;
$R_1$, $R_2$, $R_3$, $R_4$, $R_5$ and $R_6$ are as defined above;
"spacer" is as defined above; and
"heterocycle" and "heteroaromatic" are as defined herein.

In one particular embodiment, a method of treating or preventing HIV infection, or of reducing symptoms associated with AIDS is provided including contacting the cells with a compound of Formula XV, or a pharmaceutically acceptable salt, ester or prodrug thereof, is provided:

Formula XV

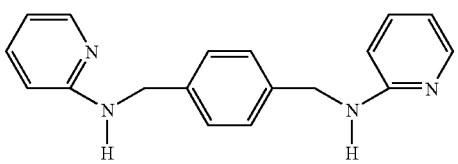

In a particular subembodiment, the compound is a salt of a compound of Formula XV, particularly a chloride salt.

In another particular embodiment, a method of treating or preventing HIV infection, or of reducing symptoms associated with AIDS is provided that includes contacting the cells with a compound of Formula XVI, or a pharmaceutically acceptable salt, ester or prodrug thereof, is provided:

Formula XVI

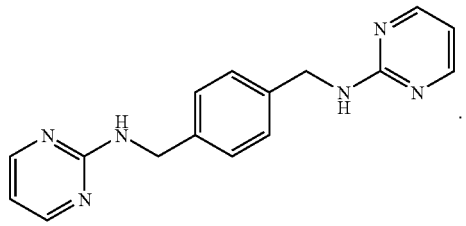

In another particular embodiment, a method of treating or preventing HIV infection, or of reducing symptoms associated with AIDS is provided that includes contacting the cells with a compound of Formula XVII, or a pharmaceutically acceptable salt, ester or prodrug thereof, is provided:

Formula XVII

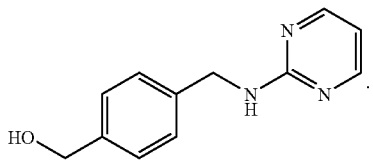

Definitions

The term alkyl, as used herein, unless otherwise specified, includes but is not limited to a saturated straight, branched, or cyclic, primary, secondary, or tertiary hydrocarbon of typically $C_1$ to $C_{10}$, and specifically includes methyl, trifluoromethyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl. The term optionally includes substituted alkyl groups. Moieties with which the alkyl group can be substituted are selected from the group consisting of hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., *Protective Groups in Organic Synthesis*, John Wiley and Sons, Second Edition, 1991, hereby incorporated by reference.

Whenever the terms "$C_1$-$C_5$ alkyl", "$C_2$-$C_5$ alkenyl", "$C_1$-$C_5$ alkoxy", "$C_2$-$C_5$ alkenoxy", "$C_2$-$C_5$ alkynyl", and "$C_2$-$C_5$ alkynoxy" are used, these are considered to include, independently, each member of the group, such that, for example, $C_1$-$C_5$ alkyl includes straight, branched and where appropriate cyclic $C_1$, $C_2$, $C_3$, $C_4$ and $C_5$ alkyl functionalities; $C_2$-$C_5$ alkenyl includes straight, branched, and where appropriate cyclic $C_2$, $C_3$, $C_4$ and $C_5$ alkenyl functionalities; $C_1$-$C_5$ alkoxy includes straight, branched, and where appropriate cyclic $C_1$, $C_2$, $C_3$, $C_4$ and $C_5$ alkoxy functionalities; $C_2$-$C_5$ alkenoxy includes straight, branched, and where appropriate cyclic $C_2$, $C_3$, $C_4$ and $C_5$ alkenoxy functionalities; $C_2$-$C_5$ alkynyl includes straight, branched and where appropriate cyclic $C_1$, $C_2$, $C_3$, $C_4$ and $C_5$ alkynyl functionalities; and $C_2$-$C_5$ alkynoxy includes straight, branched, and where appropriate cyclic $C_2$, $C_3$, $C_4$ and $C_5$ alkynoxy functionalities.

The term lower alkyl, as used herein, and unless otherwise specified, includes a $C_1$ to $C_4$ saturated straight, branched, or if appropriate, a cyclic (for example, cyclopropyl) alkyl group, optionally including substituted forms. Unless otherwise specifically stated in this application, when alkyl is a suitable moiety, lower alkyl is preferred. Similarly, when alkyl or lower alkyl is a suitable moiety, unsubstituted alkyl or lower alkyl is preferred.

The term alkylamino or arylamino refers to an amino group that has one or two alkyl or aryl substituents, respectively.

The term "protected" as used herein and unless otherwise defined refers to a group that is added to an oxygen, nitrogen, or phosphorus atom to prevent its further reaction or for other purposes. A wide variety of oxygen and nitrogen protecting groups are known to those skilled in the art of organic synthesis.

The term aryl, as used herein, and unless otherwise specified, refers to phenyl, biphenyl, or naphthyl, and preferably phenyl. The term includes both substituted and unsubstituted moieties. The aryl group can be substituted with any desired substituent that does not adversely affect the key biological properties, including but not limited to moieties selected from the group consisting of hydroxyl, thiol, amino, alkylamino, arylamino, alkoxy, aryloxy, nitro, cyano, sulfonic acid, halo (F, Cl, I, Br), carboxy, ester, acyl, alkyl, alkenyl, alkynyl, sulfate, phosphoric acid, phosphonic acid, phosphate, or phosphonate, either unprotected, or protected as necessary, as known to those skilled in the art, for example, as taught in Greene, et al., *Protective Groups in Organic Synthesis*, John Wiley and Sons, Second Edition, 1991.

The term alkaryl or alkylaryl refers to an alkyl group with an aryl substituent. The term aralkyl or arylalkyl refers to an aryl group with an alkyl substituent.

The term halo, as used herein, includes chloro, bromo, iodo, and fluoro.

The term acyl refers to a carboxylic acid ester in which the non-carbonyl moiety of the ester group is selected from straight, branched, or cyclic alkyl or lower alkyl, alkoxyalkyl including methoxymethyl, aralkyl including benzyl, aryloxyalkyl such as phenoxymethyl, aryl including phenyl optionally substituted with halogen, $C_1$ to $C_4$ alkyl or $C_1$ to $C_4$ alkoxy, sulfonate esters such as alkyl or aralkyl sulphonyl including methanesulfonyl, the mono, di or triphosphate ester, trityl or monomethoxytrityl, substituted benzyl, trialkylsilyl (e.g. dimethyl-t-butylsilyl) or diphenylmethylsilyl. Aryl groups in the esters optimally comprise a phenyl group. The term "lower acyl" refers to an acyl group in which the non-carbonyl moiety is lower alkyl.

The term "pharmaceutically acceptable salt, ester or prodrug" is used throughout the specification to describe any pharmaceutically acceptable form (such as an ester, phosphate ester, salt of an ester or a related group) of a compound which, upon administration to a patient, provides the compound described in the specification. Pharmaceutically acceptable salts include those derived from pharmaceutically acceptable inorganic or organic bases and acids such as hydrochloric acid, hydrobromic acid, sulfuric acid, nitric acid, phosphoric acid, methanesulfonic acid, ethanesulfonic acid, p-toluensulfonic acid, salicylic acid, malic acid, maleic acid, succinic acid, tartaric acid, citric acid and the like. Suitable salts include those derived from alkali metals such as potassium and sodium, alkaline earth metals such as calcium and magnesium, among numerous other acids well known in the art. Pharmaceutically acceptable "prodrugs" can refer to a compound that is metabolized, for example hydrolyzed or oxidized, in the host to form the compound of the present invention. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, dephosphorylated to produce the active compound.

The term "heterocyclic" refers to a nonaromatic cyclic group that may be partially or fully saturated and wherein there is at least one heteroatom, such as oxygen, sulfur, nitrogen, or phosphorus in the ring. The term heteroaryl or heteroaromatic, as used herein, refers to an aromatic that includes at least one sulfur, oxygen, nitrogen or phosphorus in the aromatic ring. Nonlimiting examples of heterocylics and heteroaromatics are pyrrolidinyl, tetrahydrofuryl, piperazinyl, piperidinyl, morpholino, thiomorpholino, tetrahydropyranyl, imidazolyl, pyrolinyl, pyrazolinyl, indolinyl, dioxolanyl, or 1,4-dioxanyl. aziridinyl, furyl, furanyl, pyridyl, pyrimidinyl, benzoxazolyl, 1,2,4-oxadiazolyl, 1,3,4-oxadiazolyl, 1,3,4-thiadiazole, indazolyl, 1,3,5-triazinyl, thienyl, tetrazolyl, benzofuranyl, quinolyl, isoquinolyl, benzothienyl, isobenzofuryl, indolyl, isoindolyl, benzimidazolyl, purine, carbazolyl, oxazolyl, thiazolyl, benzothiazolyl, isothiazolyl, 1,2,4-thiadiazolyl, isooxazolyl, pyrrolyl, quinazolinyl, cinnolinyl, phthalazinyl, xanthinyl, hypoxanthinyl, pyrazole, 1,2,3-triazole, 1,2,4-triazole, 1,2,3-oxadiazole, thiazine, pyridazine, benzothiophenyl, isopyrrole, thiophene, pyrazine, or pteridinyl wherein said heteroaryl or heterocyclic group can be optionally substituted with one or more substituent selected from the group consisting of halogen, haloalkyl, alkyl, alkoxy, hydroxy, carboxyl derivatives, amido, hydroxyl, acyl, amino, alkylamino, dialkylamino, arylamino, alkoxy, aryloxy, nitro, cyano, sulfonic acid, sulfate, phophonic acid, phosphate, or phosphonate, either unprotected, or protected as necessary, as known to those skilled in the art, for example, as taught in Greene, et al., "Protective Groups in Organic Synthesis," John Wiley and Sons, Second Edition, 1991, hereby incorporated by reference. Heterocycle and heteroaromatic groups include purine and pyrimidines.

Functional oxygen and nitrogen groups on the heteroaryl group can be protected as necessary or desired. Suitable protecting groups are well known to those skilled in the art, and include trimethylsilyl, dimethylhexylsilyl, t-butyldimethylsilyl, and t-butyldiphenylsilyl, trityl or substituted trityl, alkyl groups, acycl groups such as acetyl and propionyl, methanesulfonyl, and p-toluenelsulfonyl.

The term purine or pyrimidine includes, but is not limited to, adenine, $N^6$-alkylpurines, $N^6$-acylpurines (wherein acyl is C(O)(alkyl, aryl, alkylaryl, or arylalkyl), $N^6$-benzylpurine, $N^6$-halopurine, $N^6$-vinylpurine, $N^6$-acetylenic purine, $N^6$-acyl purine, $N^6$-hydroxyalkyl purine, $N^6$-thioalkyl purine, $N^2$-alkylpurines, $N^2$-alkyl-6-thiopurines, thymine, cytosine, 5-fluorocytosine, 5-methylcytosine, 6-azapyrimidine, including 6-azacytosine, 2- and/or 4-mercaptopyrmidine, uracil, 5-halouracil, including 5-fluorouracil, $C^5$-alkylpyrimidines, $C^5$-benzylpyrimidines, $C^5$-halopyrimidines, $C^5$-vinylpyrimidine, $C^5$-acetylenic pyrimidine, $C^5$-acyl pyrimidine, $C^5$-hydroxyalkyl purine, $C^5$-amidopyrimidine, $C^5$-cyanopyrimidine, $C^5$-nitropyrimidine, $C^5$-aminopyrimidine, $N^2$-alkylpurines, $N^2$-alkyl-6-thiopurines, 5-azacytidinyl, 5-azauracilyl, triazolopyridinyl, imidazolopyridinyl, pyrrolopyrimidinyl, and pyrazolopyrimidinyl. Purine bases include, but are not limited to, guanine, adenine, hypoxanthine, 2,6-diaminopurine, and 6-chloropurine.

Processes for the Preparation of Active Compounds

General Methods. $^1$H NMR or $^{13}$C NMR spectra were recorded either on 400 MHz or 100 MHz INOVA Spectrometer or 600 MHz or 150 MHz INOVA Spectrometer. The spectra obtained were referenced to the residual solvent peak. They were recorded in deuterated chloroform, dimethyl sulfoxide-d6, deuterium oxide or acetone-d6. Melting points were taken on a Thomas Hoover capillary melting point apparatus and are uncorrected. Low-resolution EI mass spectra were recorded on a JEOL spectrometer. Element analyses were performed by Atlantic Mircolab (Norcross, Ga.). Flash column chromatography was performed using Scientific Absorbent Incorporated Silica Gel 60. Analytical thin layer chromatography (TLC) was performed on precoated glass backed plates from Scientific Adsorbents Incorporated (Silica Gel 60 $F_{254}$). Plates were visualized using ultraviolet or iodine vapors or phosphomolybdic acid (PMA).

Six different methods were used to prepare the compounds of the invention and the characterization data were listed in Table 1.

Method A: Nucleophilic addition between amines and cyanamides. This method is performed according to a modified literature procedure (Braun, et al. (1938) *J. Am. Chem. Soc.* 3: 146-149). 1.0 eq. of diamine dihydrohalide and 3.0 eq. of cyanamide in absolute ethanol were stirred together under refluxing for hours. The solvent was removed under reducing pressure to get the crude salt which was purified by recrystallization in methanol.

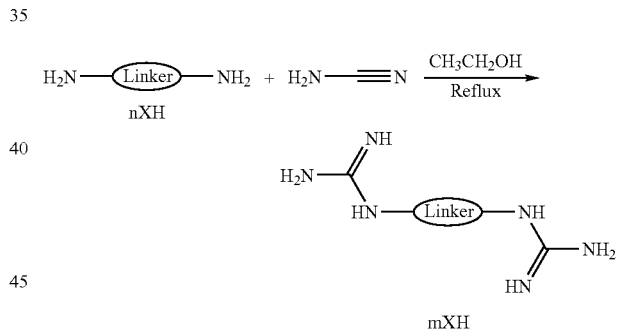

Method B: Addition-elimination between amines and methyl mercapto derivatives. This method is almost similar to a literature procedure (Linton, et al. (2001) *J. Org. Chem.* 66(22): 7313-7319). 1.0 eq. of diamine and 2.0 eq. methyl mercapto hydrohalide derivatives were dissolved in methanol. A condenser equipped with a NaOH trap at the top was attached. After refluxing for hours, the solution was reduced to minimal volume under reduced pressure. Ethyl either was added to produce white precipitate. This was recrystallized in hot methanol to give pure product.

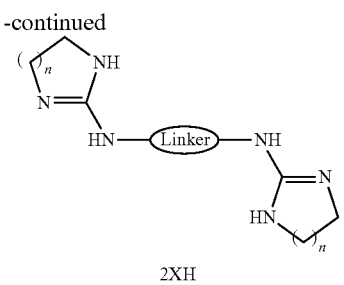

Method C: Condensation between aldehydes/ketones and amino guanidines to give guanylhydrozone derivatives. This method is modified from the literature procedure (Murdock, et al. (1982) *J. Med. Chem.* 25:505-518). A mixture of 1.0 eq. dialdehyde/ketone and 2.0 eq. amino guanidine hydrohalides in ethanol was heated under reflux for hours. The mixture was cooled to room temperature and filtered to give the guanylhydrozone hydrohalides.

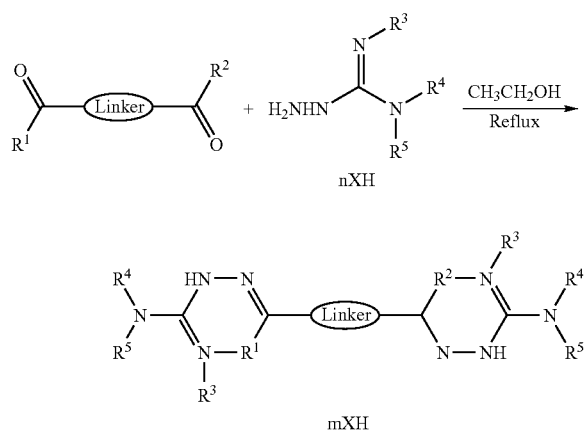

Method D: Reductive amination between aldehydes/ketones and amines (Abdel-Magid, et al. (1996) *J. Org. Chem.* 61:3849-3862). 1.0 eq. dialdehydes or ketones and 2.0 eq. amines were mixed in 1,2-dichloroethane and then treated with 3.0 eq. sodium triacetoxyborohydride (1.0-2.0 mol eq. acetic acid may also be added in reactions of ketones). The mixture was stirred at room temperature under an argon or nitrogen atmosphere for hours until the disappearance of the reactants in TLC plates. The reaction mixture was quenched by adding 1 N NaOH, and the product was extracted by ethyl ether, washed by Brine and dried by anhydrous $MgSO_4$. The solvent was evaporated to give the crude free base which could be purified by chromatography. The free base dissolved in ethanolic hydrochloride or tartaric acid to give the salts which usually can recrystallize from $MeOH/Et_2O$.

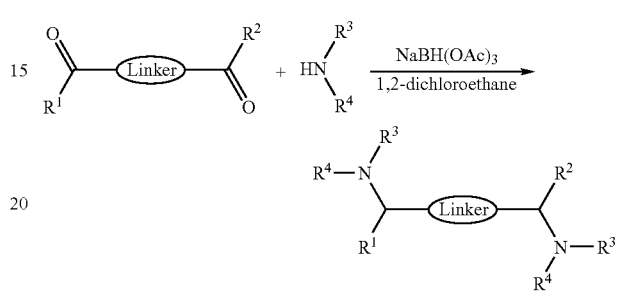

Method E: Reduction of amides (Micovic and Mihailovic (1953) *J. Org. Chem.* 18:1190). The amides could be prepared from the corresponding carboxylic acid or carboxylic chlorides. A mixture of carboxylic acid and thionyl chloride was refluxed for hours in an anhydrous system with a condenser equipped with a NaOH trap at the top. The excess thionyl chloride was removed under reduced pressure to get the carboxylic chloride. The carboxylic chloride was dissolved in dichloromethane following the addition of 2.0 eq. amine and 3 eq. pyridine. The mixture was stirred at room temperature until the disappearance of the reactants in the TLC plates. The solvent was removed under reduced pressure to get the crude amides which can be purified by chromatography.

The mixture of 1 eq. amide and 1.9 eq. $LiAlH_4$ in THF was refluxed until the disappearance of the amide from TLC plates. Then the solution was quenched with the addition of water and 15% NaOH aqueous as described in lit.5 and extracted with ethyl ether, dried over $MgSO_4$. Removal of the solvent gave the free amine product which can be purified by the chromatography. The free base dissolved in ethanolic hydrochloride or tartaric acid to give the salts which usually can recrystallize from $MeOH/Et_2O$.

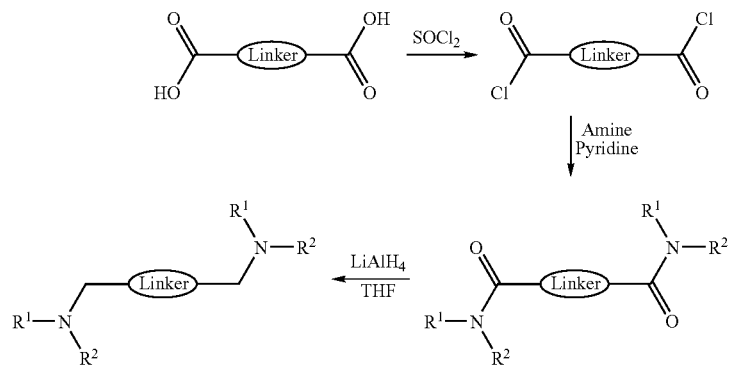

Method F: Nucleophilic substitution of halides with amines. A mixture of 1.0 eq. halides, 2.0 eq. amines and 3 eq. pyridine in ethanol was refluxed for hours until the disappearance of the reactants. The solution was condensed and extracted with ethyl ether, washed with brine, dried with MgSO$_4$. Removal of the solvent gave the free amine product which can be purified by the chromatography. The free base dissolved in ethanolic hydrochloride or tartaric acid to give the salts which usually can recrystallize from MeOH/Et$_2$O.

TABLE 1

CHARACTERIZATION DATA FOR THE PREPARED COMPOUNDS

| Entry | Structure | $^1$HNMR/$^{13}$CNMR | M.p. (° C.) | Element Analysis Found(Calcd.) | MS (EI+): m/z (M$^+$) Found (Calcd.) |
|---|---|---|---|---|---|
| WZ1S | 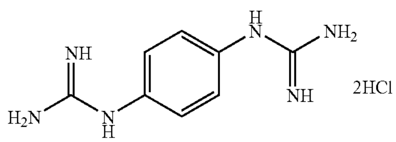 | D$_2$O: 600 Mz 1H: 7.40(4H, s); 13C: 159.019, 136.364, 129.981 | 302-304 (dec) | C$_8$H$_{14}$Cl$_2$N$_6$ C: 36.34 (36.24); H: 5.34(5.32); N: 31.76(31.70) Cl: 26.70 (26.74) | |
| XZ3S | 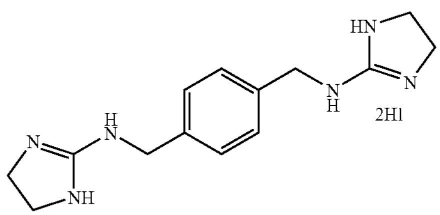 | DMSO: 400 Mz 1H: 8.66(2H, s); 7.6-8.6(4H, br); 7.31(4H, s); 4.36(4H, s); 3.60(8H, s) 13C: 159.31, 136.50, 127.53, 45.06, 42.54 | 294-296 (dec) | C$_{14}$H$_{22}$I$_2$N$_6$ C: 32.06(31.84) H: 4.35(4.20) N: 15.77(15.91) | |
| WZ4S | 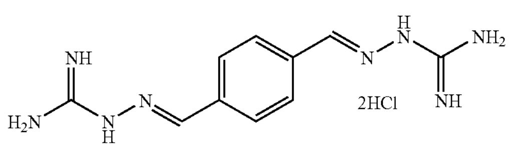 | DMSO: 400 Mz 1H: 12.28(2H, s); 8.21(2H, s); 7.94(4H, s); 7.60-8.20(8H, br) 13C: 155.52, 145.98, 135.18, 127.84 | 316-318 (dec) | C$_{10}$H$_{16}$Cl$_2$N$_8$·0.7 H$_2$O C: 36.07 (36.20); H: 5.23(5.29); N: 33.42 (33.77); Cl: 21.11 (21.37) | |
| WZ5S | 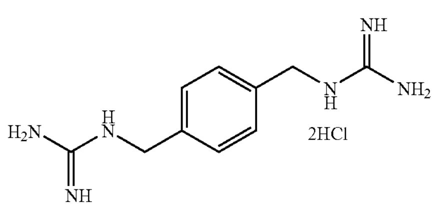 | DMSO: 400 Mz 1H: 8.08(2H, s); 7.32(4H, s); 6.85-7.71(8H, br); 4.37(4H, s) 13C: 157.12, 136.61, 127.53, 43.65 | 278-281 (dec) | | |
| WZ6S | 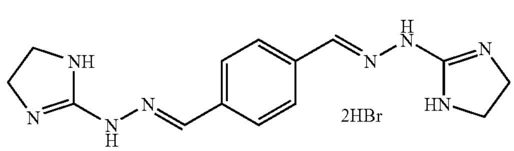 | DMSO: 400 Mz 1H: 12.39(2H, s); 8.3-9.2(4H, br); 8.22(2H, s); 7.92(4H, s); 3.75(8H, s) 13C: 195.31, 136.50, 127.53, 45.06, 42.54 | 349-352 (dec.) | C$_{14}$H$_{20}$Br$_2$N$_8$ C: 41.19(40.96) H: 6.35(6.19) N: 28.32(28.66) | |
| WZ7S | 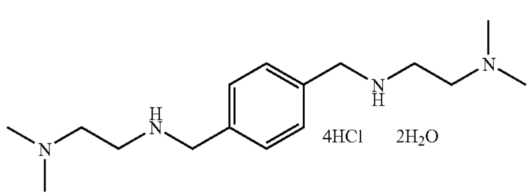 | D$_2$O: 1H(600 MHz): 7.58(4H, s); 4.37(4H, s), 3.58(8H, s); 2.98(12H, s) 13C(400 Mz): 131.95, 130.81, 52.45, 51.30, 43.45, 41.45 | 250-252 (dec.) | C$_{16}$H$_{38}$Cl$_4$N$_4$O$_2$ C: 41.75(41.83) H: 8.32(8.26) N: 12.17(11.92) | |

TABLE 1-continued

CHARACTERIZATION DATA FOR THE PREPARED COMPOUNDS

| Entry | Structure | $^1$HNMR/$^{13}$CNMR | M.p. (° C.) | Element Analysis Found(Calcd.) | MS (EI+): m/z (M$^+$) Found (Calcd.) |
|---|---|---|---|---|---|
| WZ8S | (structure: PhNH-CH$_2$CH$_2$-NH-CH$_2$-C$_6$H$_4$-CH$_2$-NH-CH$_2$CH$_2$-NHPh · 2HCl) | D$_2$O: 400 Mz 1H: 7.45(4H, s); 7.24(4H, t, J=7.2 Hz); 6.82(2H, t, J=7.2 Hz); 6.73(4H, d, J=7.2 Hz); 4.27(4H, s); 3.47(4H, t, J=6.2 Hz); 3.24(4H, t, J=6.2 Hz) | 320-322 (dec.) | C$_{24}$H$_{32}$Cl$_2$N$_4$ C: 64.42(64.32) H: 7.21(7.21) N: 12.52(12.30) | |
| WZ8 | (structure: PhNH-CH$_2$CH$_2$-NH-CH$_2$-C$_6$H$_4$-CH$_2$-NH-CH$_2$CH$_2$-NHPh) | CDCl3: 1H(600 MHz): 7.29(4H, s); 7.18(4H, t, J=5.2 Hz); 6.71(2H, t, J=4.8 Hz); 6.64(4H, d, J=6 Hz), 3.81(4H, s); 3.23(4H, t, J=3.6 Hz); 2.91(4H, t, J=3.6 Hz); 4.12(2H, br) 13C(400 Mz): 148.64; 139.18; 129.38; 128.36; 117.53; 113.13; 53.49; 48.17; 43.65 | 42-43 | | |
| WX9S | (structure: 4-Py-CH$_2$-NH-CH$_2$-C$_6$H$_4$-CH$_2$-NH-CH$_2$-4-Py · 4HCl) | D$_2$O: 400 Mz 1H: 8.87(4H, d, J=7.2 Hz); 8.12(4H, d, J=7.2 Hz); 7.63(4H, ); 4.66(4H, ): 4.48(4H, s) 13C: 151.21; 142.45; 131.84; 131.18; 127.47; 51.35; 49.03 | 244-246 (dec.) | C$_{20}$H$_{26}$Cl$_4$N$_4$0.7 H$_2$O C: 50.60(50.37) H: 5.74(5.79) N: 11.49(11.75) | |
| WZ9 | (structure: 4-Py-CH$_2$-NH-CH$_2$-C$_6$H$_4$-CH$_2$-NH-CH$_2$-4-Py) | CDCl3: 1H(600 MHz): 8.55(4H, d, J=5.4 Hz); 7.32(4H, s); 7.30(4H, d, J=5.4 Hz); 3.83(4H, ); 3.81(4H, s); 1.73(2H, s) 13C(400 MHz): 149.73; 149.38; 138.72; 128.21; 122.93; 52.84; 51.72 | | | |

TABLE 1-continued

CHARACTERIZATION DATA FOR THE PREPARED COMPOUNDS

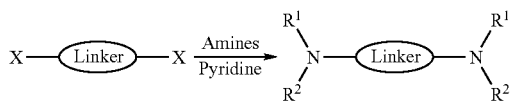

| Entry | Structure | $^1$HNMR/$^{13}$CNMR | M.p. (° C.) | Element Analysis Found(Calcd.) | MS (EI+): m/z (M$^+$) Found (Calcd.) |
|---|---|---|---|---|---|
| WZ29S | (structure: pyridin-4-ylmethyl-NH-CH2-C6H4-CH2-NH-CH2-pyridin-4-yl, 4HCl) | D2O: 600 Mz 1H: 8.87(4H, d, J=7.2 Hz); 8.12(4H, d, J=7.2 Hz); 7.63(4H, s); 4.66(4H, s); 4.48(4H, s) | | C20H26Cl4N4.0.7H2O C: 50.57(50.37) H: 5.70(5.79) N: 11.55(11.75) | |
| XZ10S | (structure: pyridin-3-ylmethyl-NH-CH2-C6H4-CH2-NH-CH2-pyridin-3-yl, 2HCl) | D$_2$O: 1H: 600 mHz 8.61(2H, dd, J=6 Hz, 1.2 Hz); 8.60(2H, d, J=2.4 Hz); 7.99(2H, dt, J=7.8 Hz, 1.8 Hz); 7.56(6H, m); 4.39(4H, s); 4.37(4H, s) 13C: 400 MHz 148.85; 149.82; 139.26; 132.13; 130.81; 127.48; 124.83; 50.48; 48.15 | 318-320 (dec.) | C$_{20}$H$_{24}$Cl$_2$N$_4$ C: 60.45(61.38) H: 6.17(6.18) N: 13.89(14.32) | |
| WZ11S | (structure: pyridin-2-ylmethyl-NH-CH2-C6H4-CH2-NH-CH2-pyridin-2-yl, 4HCl) | D$_2$O: 1H: 8.76(2H, d, J=4.8 Hz); 8.35(2H, dt, J=8 Hz, J=1.2 Hz); 7.91(2H, d, J=8 Hz); 7.86(2H, t, J=6.4 Hz); 4.62(4H, s); 4.47(4H, s) 13C: 146.12; 145.53; 144.95; 131.84; 131.07; 127.47; 127.26; 51.18; 47.91 | 236-238 (dec.) | C$_{20}$H$_{26}$Cl$_4$N$_4$0.5 H$_2$O 0.2CH$_3$COOCH$_2$CH$_3$ C: 50.59(50.89) H: 6.08(5.87) N: 11.46(11.41) | |
| WZ13S | (structure: phenyl-NH-CH2-C6H4-CH2-NH-phenyl, 2HCl) | DMSO-D2O: 400 Mz 1H: 7.35(4H, s), 7.30(4H, m), 7.10(6H, m), 4.41(4H, s) 13C: 137.85, 133.27, 129.88, 129.46, 126.58, 121.70, 51.82 | | | |

TABLE 1-continued

CHARACTERIZATION DATA FOR THE PREPARED COMPOUNDS $$X-\text{Linker}-X \xrightarrow[\text{Pyridine}]{\text{Amines}} \underset{R^2}{\overset{R^1}{N}}-\text{Linker}-\underset{R^2}{\overset{R^1}{N}}$$

| Entry | Structure | $^1$HNMR/$^{13}$CNMR | M.p. (° C.) | Element Analysis Found(Calcd.) | MS (EI+): m/z (M$^+$) Found (Calcd.) |
|---|---|---|---|---|---|
| WZ13 | 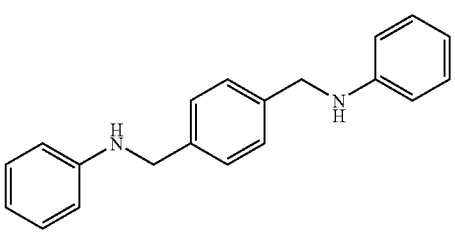 | CDCl3: 400 Mz 1H; 7.38(4H, s); 7.22(4H, t, J=7.6 Hz); 6.76(2H, t, J=7.6 Hz); 7.67(4H, d, J=7.6 Hz); 4.35(4H, s); 4.06(2H, br) 13C: 148.28, 138.65, 129.46, 127.98, 117.78, 113.03, 48.20 | 126-127 | | |
| WZ14 | 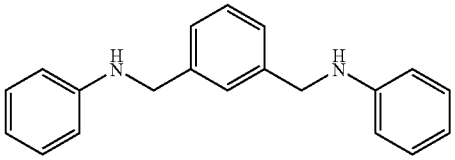 | CDCl3: 400 Mz 1H: 7.43(1H, s); 7.36(3H, m); 7.23(4H, m); 6.78(2H, t, J=7.7 Hz); 6.68(4H, d, J=7.7 Hz); 4.07(2H, s) 13C: 148.26, 140.09, 129.44, 129.03, 126.74, 126.54, 117.77, 113.05, 48.42 | | | 288.5 (288.4) |
| WZ14S | 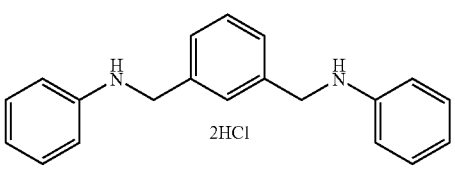 | D2O: 400 Mz 1H: 7.49(6H, m); 7.37(3H, m); 7.21(4H, m); 7.15(1H, s); 4.59(4H, s) 13C: 133.95, 132.22, 131.68, 131.06, 130.32, 129.86, 122.93 54.6 | | | |
| WZZL811 | 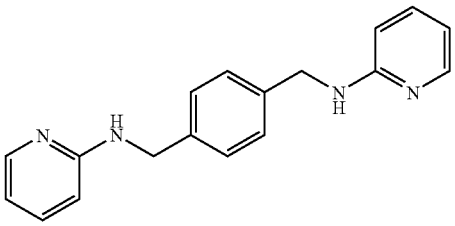 | DMSO: 400 Mz 1H: 7.93(2H, dd, J=4.8 Hz, 1.2 Hz); 7.34(2H, td, J=12.8 Hz, 2 Hz); 7.25(4H, s); 6.96(2H, t, J=6 Hz), 6.45(4H, m); 4.41(4H, d, J=6 Hz) 13C: 158.66, 147.53, 138.84, 136.60, 127.11, 111.67, 108.11, 43.93 | 192-194 | | 290.5 (290.4) |

TABLE 1-continued

CHARACTERIZATION DATA FOR THE PREPARED COMPOUNDS

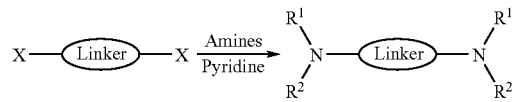

| Entry | Structure | $^1$HNMR/$^{13}$CNMR | M.p. (° C.) | Element Analysis Found(Calcd.) | MS (EI+): m/z (M$^+$) Found (Calcd.) |
|---|---|---|---|---|---|
| WZZL811S | (structure: 2HCl salt) | D2O: 400 Mz 1H: 7.89(2H, td, J=8.4 Hz, 1.6 Hz); 7.79(2H, d, J=6.4 Hz); 7.43(4H, s); 7.02(2H, d, J=8.4 Hz); 6.90(2H, t, J=6.4 Hz); | | $C_{18}H_{18}N_4 \cdot 2HCl$ C: 59.28(59.51) H: 5.44(5.55) N: 15.19(15.4) Cl: 19.73 (19.52) | |
| WZZL811TS | (structure: 2TsOH salt) | DMSO: 1H(600 MHz): 9.07(2H, br), 7.95(4H, m); 7.49(4H, d, J=8.4 Hz); 7.40(4H, s); 7.11(6H, m); 6.90(2H, t, J=6 Hz); 4.58(4H, d, J=5.4 Hz); 3.68(2H, br) 2.84(4H, S) 13C(400 Mz): 152.56, 145.40, 143.49, 137.82, 136.26, 135.88, 128.12, 127.93, 125.48, 112.42, 44.56, 20.78 | | | |
| WZZL811LTR | (structure: 1.75 tartrate) | D2O: 400 Mz 1H: 7.88(2H, t, J=9.2 Hz); 7.78(2H, d, J=6.4 Hz); 7.42(4H, s); 7.02(2H, d, J=9.2 Hz); 6.89(2H, t, J=6.4 Hz); 4.62(4H, s); 4.45(3H, s) 13C: 173.18, 158.52, 147.25, 138.78, 136.79, 127.14, 111.69, 108.23, 72.16, 43.94 | | $C_{18}H_{18}N_4 \cdot$ $1.75 C_4H_6O_6$ C: 53.51(54.3) H: 5.35(5.19) N: 10.11(10.13) | |

TABLE 1-continued
CHARACTERIZATION DATA FOR THE PREPARED COMPOUNDS
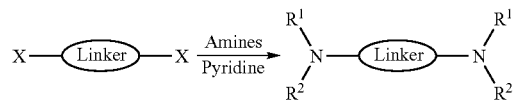
| Entry | Structure | ¹HNMR/¹³CNMR | M.p. (° C.) | Element Analysis Found(Calcd.) | MS (EI+): m/z (M⁺) Found (Calcd.) |
|---|---|---|---|---|---|
| WZ17 | 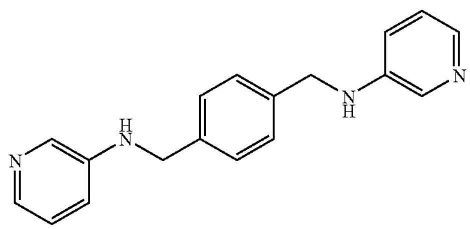 | DMSO 1H(600 Mz): 7.96(2H, D, J=3 Hz); 7.73(2H, dd, J=3 Hz, 1.2 Hz); 7.32(4H, s); 7.02(2H, dd, J=6 Hz, 4.2 Hz); 6.86(2 Hz, dq, J=6 Hz, 4.2 Hz, 1.8 Hz); 6.46(2H, t, 6 Hz); 6.25(4H, d, J=6 Hz); 13C(400 Mz): 145.30, 138.79, 137.57, 136.17, 128.00, 124.21, 118.39, 46.42, | | | 290.4 (290.4) |
| WZ17S | 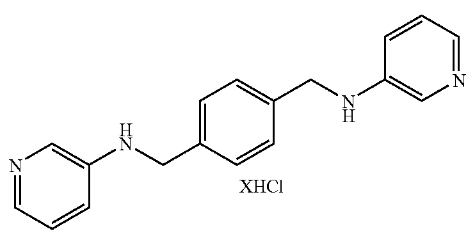 | D2O: 600 Mz 1H: 7.92(4H, m); 7.67(4H, m); 7.42(4H, s); 4.49(4H, s) 13C: 147.21, 136.80, 128.30, 128.25, 127.85, 127.16, 124.26, 45.73 | | | |
| WZ18 | 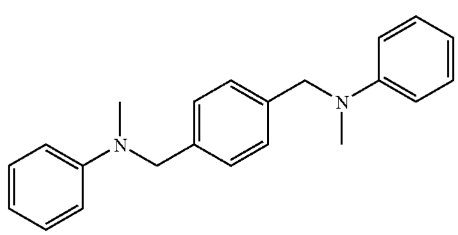 | CDCl3: 400 Mz 1H: 7.24(4H, m): 7.19(4H, s); 6.75(4H, m); 4.53(4H, s); 3.02(6H, s) 13C: 149.90, 137.83, 129.35, 127.16, 116.69, 112.52, 56.53, 38.69 | | | |
| WZ19 | 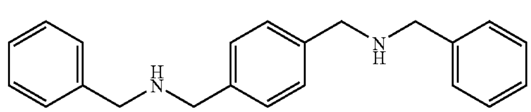 | DMSO 1H(600 Mz): 7.32(8H, m); 7.28(4H, s); 7.22(2H, tt, J=7.2 Hz, 1.2 Hz); 3.66(4H, s); 3.65(4H, s); 2.53(2H, s) 13C(400 Mz): 140.44, 139.12, 128.49, 128.33, 128.26, 127.04, 53.24, 53.00 | | | |

TABLE 1-continued
CHARACTERIZATION DATA FOR THE PREPARED COMPOUNDS
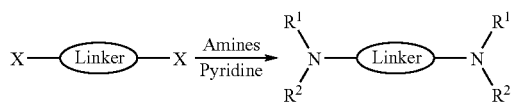
| Entry | Structure | $^1$HNMR/$^{13}$CNMR | M.p. (° C.) | Element Analysis Found(Calcd.) | MS (EI+): m/z (M$^+$) Found (Calcd.) |
|---|---|---|---|---|---|
| WZ19S | 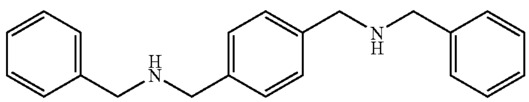 | DMSO: 400 Mz 1H: 9.66(4H, s); 7.59(4H, s); 7.54(4H, m); 7.43(6H, m); 4.17(4H, s); 4.13(4H, s) | | | |
| WZ20 | 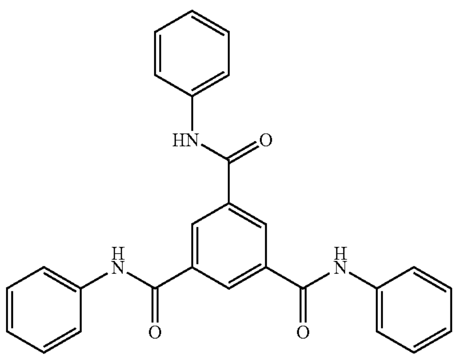 | DMSO 1H(600 Mz): 10.60(3H, s); 8.71(3H, s); 7.83(6H, d, J=7.8 Hz); 7.40(6H, t, J=7.8 Hz); 7.15(3H, t, J=7.2 Hz); 13C(400 Mz): 164.54, 138.94, 135.50, 129.79, 128.75, 124.00, 120.41 | 318-320 | | |
| WZ21 | 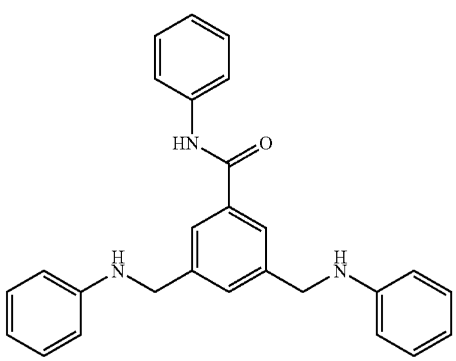 | CDCl3: 400 Mz 1H: 7.79(3H, s); 7.62(2H, d, J=7.8 Hz), 7.58(1H, s); 7.38(2H, t, J=7.8 Hz); 7.18(5H, m); 6.75(2H, td, J=7.8 Hz, 1.2 Hz); 6.64(4H, d, J=6.6 Hz); 4.41(4H, s) 13C: 165.97, 147.92, 141.07, 138.00, 135.79, 129.80, 129.46, 129.18, 125.03, 124.78, 120.52, 118.02, 113.15, 48.04 | | | 407.6 (407.5) |
| WZ22 | 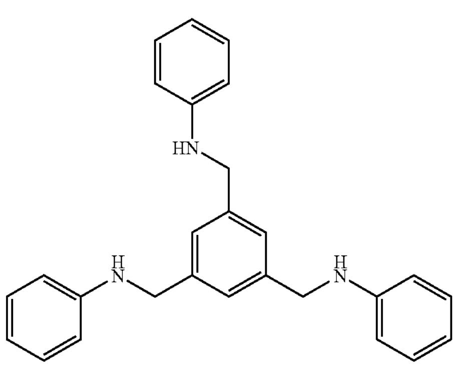 | CDCl3: 400 Mz 1H: 7.31(3H, s); 7.18(6H, m); 6.74(3H, tt, J=7.2 Hz, 0.8 Hz); 6.63(6H, dm, J=7.2 Hz); 4.32(6H, s); 4.03(3H, br) 13C: 148.24, 140.60, 129.44, 125.66, 117.84, 113.10, 48.42 | | | 393.5 (393.5) |

TABLE 1-continued

CHARACTERIZATION DATA FOR THE PREPARED COMPOUNDS

X—Linker—X $\xrightarrow{\text{Amines}}$ R$^1$R$^2$N—Linker—NR$^1$R$^2$
        Pyridine

| Entry | Structure | $^1$HNMR/$^{13}$CNMR | M.p. (° C.) | Element Analysis Found(Calcd.) | MS (EI+): m/z (M$^+$) Found (Calcd.) |
|---|---|---|---|---|---|
| WZ22S | 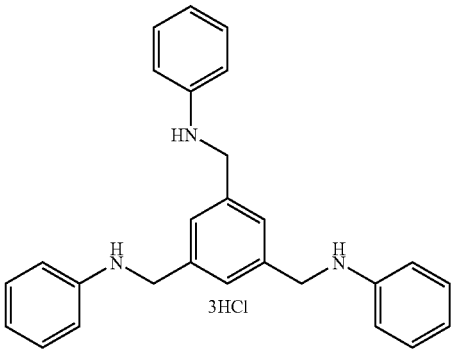 | D2O: 400 Mz 1H: 7.41(9H, m); 7.16(3H, s); 6.98(6H, m), 4.51(6H, S) | | | |
| WZ23 | 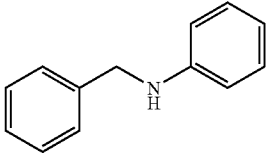 | CDCl3: 1H(600 Mz): 7.41(4H, m); 7.32(1H, t, J=7.2 Hz); 7.22(2H, t, J=7.2 Hz); 6.76(1H, td, J=7.2 Hz, 1.2 Hz); 6.68(2H, d, J=7.2 Hz); 4.37(2H, s); 4.06(1H, br) 13C(400 Mz): 148.33, 139.62, 129.44, 128.81, 127.68, 127.39, 117.72, 113.01, 48.46 | 34-35 | | |
| WZ23S | 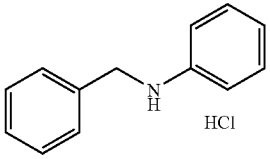 | CDCl3: 600 Mz 1H: 11.85(2H, br); 7.30(10H, m); 4.36(2H, s) 13C: 134.37, 131.26, 129.86, 129.60, 129.58, 129.44, 128.87, 124.17, 56.18 | 211-212 | | |
| WZ24 | 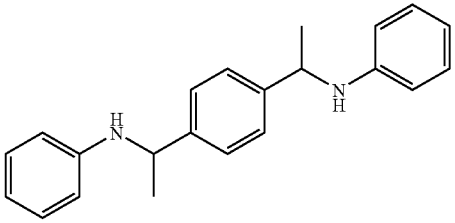 | CDCl3: 400 Mz 1H: 7.32(4H, s); 7.11(4H, t, J=7.8 Hz); 6.66(2H, tm, J=7.2 Hz); 6.52(4H, dm, J=7.6 HZ); 4.48(2H, m); 1.52(3H, s); 1.50(3H, s) 13C: 147.51, 143.93, 143.96, 129.30, 126.35, 117.35, 117.36, 113.43, 53.31, 53.29, 25.01, 24.91 | | | |

TABLE 1-continued

CHARACTERIZATION DATA FOR THE PREPARED COMPOUNDS

| Entry | Structure | $^1$HNMR/$^{13}$CNMR | M.p. (° C.) | Element Analysis Found(Calcd.) | MS (EI+): m/z (M$^+$) Found (Calcd.) |
|---|---|---|---|---|---|
| WZ25 | 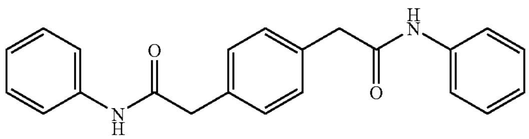 | DMSO 1H(600 Mz): 10.13(2H, s); 7.58(4H, d, J=7.2 Hz); 7.28(8H, t, J=8.1 Hz); 7.02(2H, t, J=7.2 Hz); 3.61(4H, s) 13C(400 Mz): 169.13, 139.23, 134.24, 129.05, 128.69, 123.18, 119.10, 42.95 | | | |
| WZ26 | 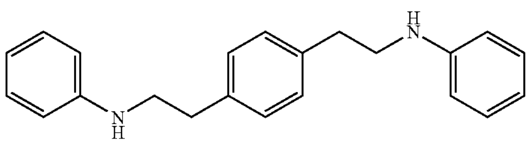 | CDCl3 1H(600 Mz): 7.20(8H, m); 6.73(2H, t, J=7.2 Hz); 6.64(4H, d, J=7.2 Hz); 3.69(2H, br); 3.42(4H, t, J=7.2 Hz); 2.92(4H, t, J=7.2 Hz) 13C(400 Mz): 148.21, 137.60, 129.49, 129.22, 117.87, 113.18, 45.24, 35.32 | | | 316.5 (316.4) |
| WZ27 | 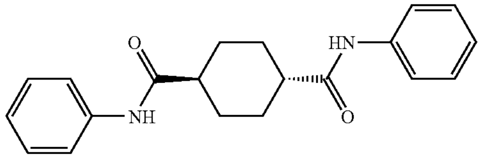 | DMSO 1H(600 Mz): 9.86(2H, s); 7.60(4H, d, J=1.8 Hz); 7.28(4H, t, J=7.8 Hz); 7.02(2H, t, J=7.2 Hz); 2.35(2H, br); 1.92(4H, d, J=6.6 Hz); 1.49(4H, m) 13C(400 Mz): 173.95, 139.43, 128.64, 122.93, 119.04, 44.10, 28.29 | | | |

TABLE 1-continued

CHARACTERIZATION DATA FOR THE PREPARED COMPOUNDS

| Entry | Structure | $^1$HNMR/$^{13}$CNMR | M.p. (° C.) | Element Analysis Found(Calcd.) | MS (EI+): m/z (M$^+$) Found (Calcd.) |
|---|---|---|---|---|---|
| WZ28 | 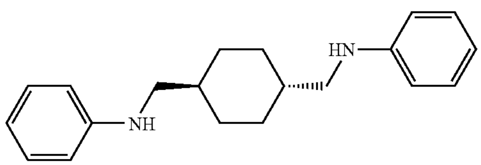 | CDCl3 1H(600 Mz): 7.18(4H, m); 6.69(2H, tt, 7.8 Hz, 0.6 Hz); 6.60(4H, dd, J=9.0 Hz, 0.6 Hz); 3.72(2H, s); 2.99(4H, d, J=6.6 Hz); 1.92(4H, d, J=6.6 Hz); 1.59(2H, m); 1.03(4H, m) 13C(400 Mz): 148.71, 129.45, 117.19, 112.82, 50.65, 37.94, 30.96 | | | 294.5 (294.4) |
| WZ30 | 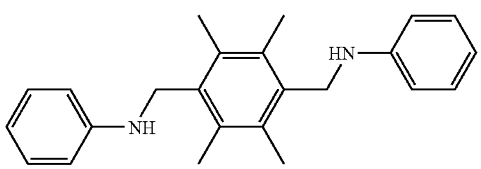 | CDCl3 1H(600 Mz): 7.26(4H, m); 6.78(2H, t, J=7.8 Hz); 7.71(4H, d, J=7.8 Hz); 4.28(4H, s); 3.48(2H, br); 2.32(12H, s) 13C(400 Mz): 148.44, 134.94; 134.31; 129.53; 117.67; 112.73; 43.70, 16.52 | | | 344.7 (344.5) |
| WZ31 | 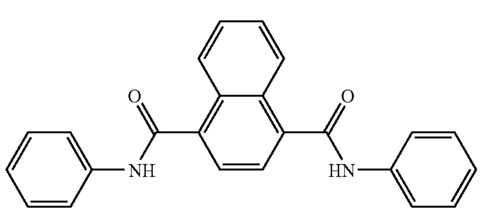 | DMSO: 400 Mz 1H: 10.66(2H, q, J=3.2 Hz); 8.24(2H, m); 7.83(6H, m); 6.67(2H, q, J=3.2 Hz); 7.40(4H, t, J=7.2 Hz); 7.15(2H, t, J=7.2 Hz) 13C: 166.84, 139.15, 136.65, 129.79, 128.78, 127.30, 125.57, 124.36, 123.88, 119.91, | | | |

TABLE 1-continued

CHARACTERIZATION DATA FOR THE PREPARED COMPOUNDS

| Entry | Structure | $^1$HNMR/$^{13}$CNMR | M.p. (°C.) | Element Analysis Found(Calcd.) | MS (EI+): m/z (M$^+$) Found (Calcd.) |
|---|---|---|---|---|---|
| WZ32 | 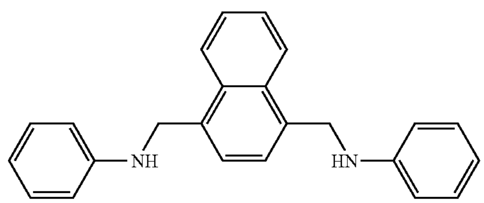 | CDCl3 1H(600 MHz): 8.15(2H, q, J=3.6 Hz); 7.58(2H, q, J=3.6 Hz); 7.51(2H, s); 7.23(4H, t, J=7.2 Hz); 6.77(2H, t, J=7.2 Hz); 6.71(4H, d, J=7.2 Hz); 4.76(4H, s); 4.11(2H, br); 13C(400 Mz): 148.24, 134.54, 132.15, 129.56, 126.51, 126.02, 124.58, 117.97, 113.06, 46.75 | | | 338.5 (338.4) |
| WZ33 | 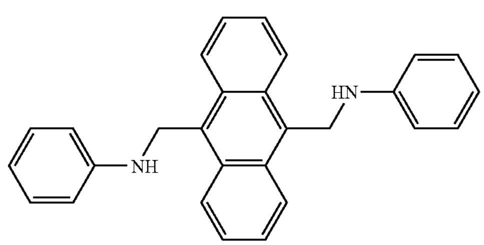 | CDCl3: 400 Mz 1H: 8.36(4H, dd, J=7.2 Hz, 3.2 Hz); 7.55(4H, dd, J=7.2 Hz, 3.2 Hz); 7.32(4H, t, J=8.0 Hz); 6.85(6H, m); 5.20(4H, s); 3.98(2H, br) 13C: 148.51, 130.86, 130.53, 129.68, 126.50, 125.13, 118.15, 112.94, 41.34 | | | |
| WZ34 | 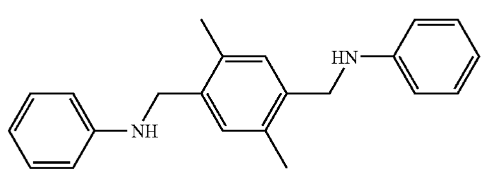 | CDCl3: 400 Mz 1H: 7.21(6H, m); 6.76(2H, t, J=7.2 Hz); 6.67(4H, d, J=8.0 Hz); 4.24(4H, s); 3.90(2H, br); 2.32(6H, s) 13C: 148.42, 136.25, 134.21, 130.85, 129.50, 117.82, 113.04, 46.44, 18.68 | | | 316.5 (316.4) |

TABLE 1-continued

CHARACTERIZATION DATA FOR THE PREPARED COMPOUNDS

| Entry | Structure | ¹HNMR/ ¹³CNMR | M.p. (° C.) | Element Analysis Found(Calcd.) | MS (EI+): m/z (M⁺) Found (Calcd.) |
|---|---|---|---|---|---|
| WZ35 | (phenyl-HN-CH₂-(1,2-phenylene)-CH₂-NH-phenyl) | CDCl3 1H(600 Mz): 7.44(2H, m); 7.30(2H, m); 7.19(4H, tt, J=6.6 Hz, 1.8 Hz); 6.77(2H, t, J=7.8 Hz); 6.68(4H, d, J=7.8 Hz); 4.60(2H, br); 4.40(4H, s) 13C(400 Mz): 148.13, 137.44, 129.56, 129.51, 128.17, 118.21, 113.41, 46.55 | | | |
| WZ35S | (phenyl-HN-CH₂-(1,2-phenylene)-CH₂-NH-phenyl) · 2HCl | DMSO: 400 Mz 1H: 8.25(4H, br): 7.43(2H, m); 7.27(2H, m); 7.16(4H, t, J=7.8 Hz); 6.79(6H, m); 4.39(4H, s) | | | |
| WZ36 | (HO-C₆H₄-NH-CH₂-C₆H₄-CH₂-NH-C₆H₄-OH) | Acetone-d6: 400 Mz 1H: 7.39(2H, s); 7.33(4H, s); 6.61(4H, m); 6.54(4H, m); 4.86(2H, s); 4.23(4H, s) 13C: 149.83, 143.17, 140.13, 128.30, 116.61, 114.88, 49.11 | | | |
| WZ37 | (NC-C₆H₄-NH-CH₂-C₆H₄-CH₂-NH-C₆H₄-CN) | DMSO: 400 Mz 1H: 7.42(4H, d, J=9.2 Hz); 7.29(4H, s); 7.26(2H, t, J=6.0 Hz); 6.63(4H, d, J=9.2 Hz); 4.30(4H, d, J=6.0 Hz) 13C: 152.04, 137.68, 133.31, 127.31, 120.54, 112.22, 95.88, 45.41 | | | 338.5 (338.4) |

TABLE 1-continued

CHARACTERIZATION DATA FOR THE PREPARED COMPOUNDS

| Entry | Structure | $^1$HNMR/$^{13}$CNMR | M.p. (° C.) | Element Analysis Found(Calcd.) | MS (EI+): m/z (M$^+$) Found (Calcd.) |
|---|---|---|---|---|---|
| WZ38 | O$_2$N–C$_6$H$_4$–NH–CH$_2$–C$_6$H$_4$–CH$_2$–HN–C$_6$H$_4$–NO$_2$ | DMSO: 400 Mz 1H: 7.97(4H, d, J=9.2 Hz); 7.88(2H, t, J=5.6 Hz); 6.66(4H, d, J=9.2 Hz); 4.39(4H, d, J=5.6 Hz) 13C: 154.40, 137.42, 135.86, 127.42, 126.14, 45.50 | | | |
| WZ40 | pyrimidine-NH-CH$_2$-C$_6$H$_4$-CH$_2$-NH-pyrimidine | DMSO 1H(600 Mz): 8.24(4H, d, J=3.2 Hz); 7.63(2H, t, J=4.0 Hz); 7.21(4H, s); 6.54(2H, t, J=3.2 Hz); 4.43(4H, d, J=4.0 Hz) 13C(400 Mz): 162.26, 157.95, 138.59, 126.86, 110.15, 43.62 | | | 292.4 (292.3) |
| WZ41 | HO-CH$_2$-C$_6$H$_4$-CH$_2$-NH-pyrimidine | CDCl3: 400 Mz 1H: 8.28(2H, d, J=4.8 Hz); 7.34(4H, s); 6.56(1H, t, J=4.8 Hz); 5.46(1H, br); 4.69(2H, s); 4.62(2H, d, J=6.0 Hz); 2.08(1H, s) 13C: 162.27, 157.93, 140.71, 138.74, 126.74, 126.36, 110.14, 62.73, 43.65 | | | 215.2 (215.3) |

TABLE 1-continued

CHARACTERIZATION DATA FOR THE PREPARED COMPOUNDS

| Entry | Structure | $^1$HNMR/$^{13}$CNMR | M.p. (° C.) | Element Analysis Found(Calcd.) | MS (EI+): m/z (M$^+$) Found (Calcd.) |
|---|---|---|---|---|---|
| WZ42 | 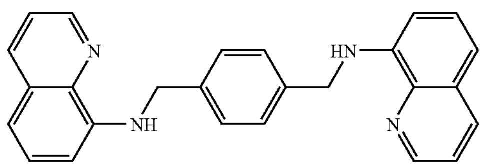 | CDCl3 1H(600 Mz): 8.73(2H, dd, J=3.6 Hz, 1.2 Hz); 8.08(2H, dd, J=7.8 Hz, 1.2 Hz), 7.43(4H, s); 7.37(4H, m); 7.07(2H, d, J=7.8 Hz); 6.67(2H, d, J=7.8 Hz); 6.6(2H, t, J=5.4 Hz); 4.57(4H, d, J=5.4 Hz) 13C(400 Mz): 147.14, 144.77, 138.43, 138.36, 136.23, 128.84, 127.98, 127.94, 121.63, 114.36, 105.32, 47.67 | | | |
| WZ43 | 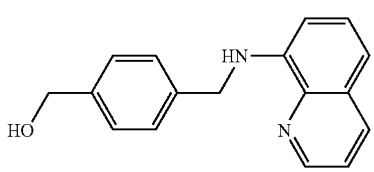 | CDCl3: 400 Mz 1H: 8.73(1H, dd, J=4.0 Hz, 1.6 Hz); 8.08(1H, dd, J=8.4 Hz, 2.0 Hz); 7.45(2H, d, J=7.6 Hz); 7.37(4H, m); 7.07(1H, dd, J=8.4 Hz, 1.6 Hz); 6.63(2H, d, J=8.4 Hz); 4.70(2H, d, J=6.0 Hz); 4.58(2H, d, J=6.0 Hz); 1.66(1H, 6.0 HZ) 13C: 147.14, 144.65, 139.97, 138.90, 138.37, 136.26, 128.82 127.93, 127.76, 127.55, 121.61, 114.41, 105.39, 65.32, 47.60 | | | |

TABLE 1-continued

CHARACTERIZATION DATA FOR THE PREPARED COMPOUNDS

| Entry | Structure | ¹HNMR/ ¹³CNMR | M.p. (° C.) | Element Analysis Found(Calcd.) | MS (EI+): m/z (M⁺) Found (Calcd.) |
|---|---|---|---|---|---|
| WZ48 | 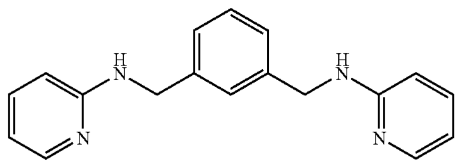 | CDCl3 1H(600 MHz): 8.10(2H, d, J=4.8 Hz); 7.40(2H, tt, J=6.0 Hz, 1.8 Hz); 7.37(1H, s); 7.31(2H, m); 7.28(1H, s); 6.60(2H, t, J=6.0 Hz); 6.36(2H, d, J=8.4 Hz); 4.89(2H, t, J=6.0 Hz); 4.50(4H, d, J=6.0 Hz) 13C(400 Mz): 158.77, 148.44, 139.91, 137.67, 129.16, 126.64, 126.52, 113.42, 107.08, 46.42 | | | |
| WZ48S | 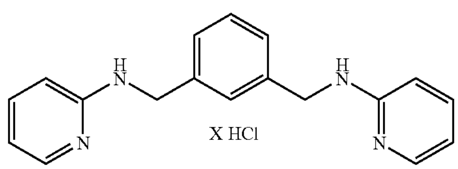 | D2O: 600 Mz 1H: 7.83(2H, td, J=9 HzHz, 1.2 Hz); 7.72(2H, d, J=6.6 Hz); 7.45(1H, t, J=7.8 Hz); 7.36(2H, d, J=7.8 Hz); 7.27(1H, s), 6.94(2H, d, J=9.0 Hz); 6.87(2H, t, J=6.6 Hz); 4.63(4H, s) | | | |
| WZ49 | 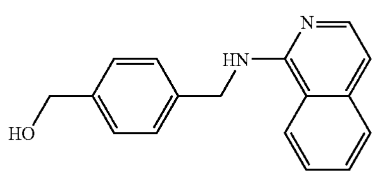 | CDCl3: 400 Mz 1H: 8.03(1H, d, J=6.0 Hz); 7.30(2H, m), 7.61(1H, td, J=7.6 Hz, 1.2 Hz); 7.46(3H, m); 7.37(2H, m); 6.99(1H, d, J=5.6 Hz); 5.44(1H, t, J=6.0 Hz); 4.82(2H, d, J=6.0 Hz), 4.72(2H, 2), 1.79(1H, s) 13C: 155.01, 141.51, 140.31, 139.06, 137.28, 129.96, 128.49, 127.60, 127.43, 126.17, 121.54, 118.25, 111.52, 65.30, 45.94 | | | |

TABLE 1-continued
CHARACTERIZATION DATA FOR THE PREPARED COMPOUNDS
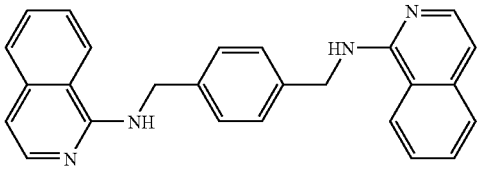
| Entry | Structure | ¹HNMR/¹³CNMR | M.p. (° C.) | Element Analysis Found(Calcd.) | MS (EI+): m/z (M⁺) Found (Calcd.) |
|---|---|---|---|---|---|
| WZ50 | 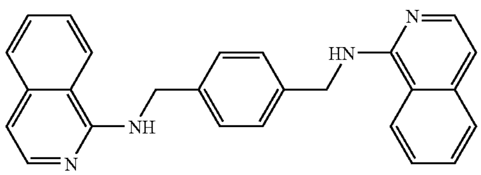 | CDCl3: 400 Mz 1H: 8.03(2H, d, J=6.0 Hz); 7.78(2H, d, J=8.0 Hz); 7.70(2H, d, J=8.0 Hz); 7.60(2H, td, J=7.6 Hz, 1.6 Hz); 7.45(2H, td, J=7.6 Hz, 1.6 Hz); 7.424(4H, s); 6.98(2H, d, J=5.2 Hz); 5.57(2H, br); 4.81(4H, d, J=5.2 Hz) 13C: 154.96, 141.33, 138.71, 137.26, 130.03, 128.59, 127.42, 126.22, 121.69, 118.28, 111.49, 45.90 | | | |
Additional compounds prepared and tested in cell assays to determine viral inhibition:

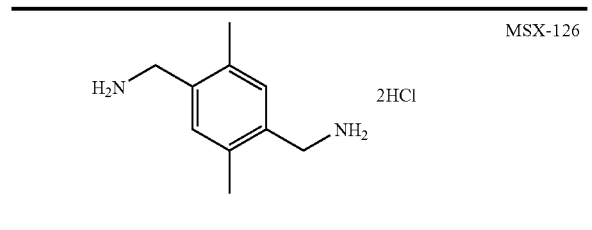

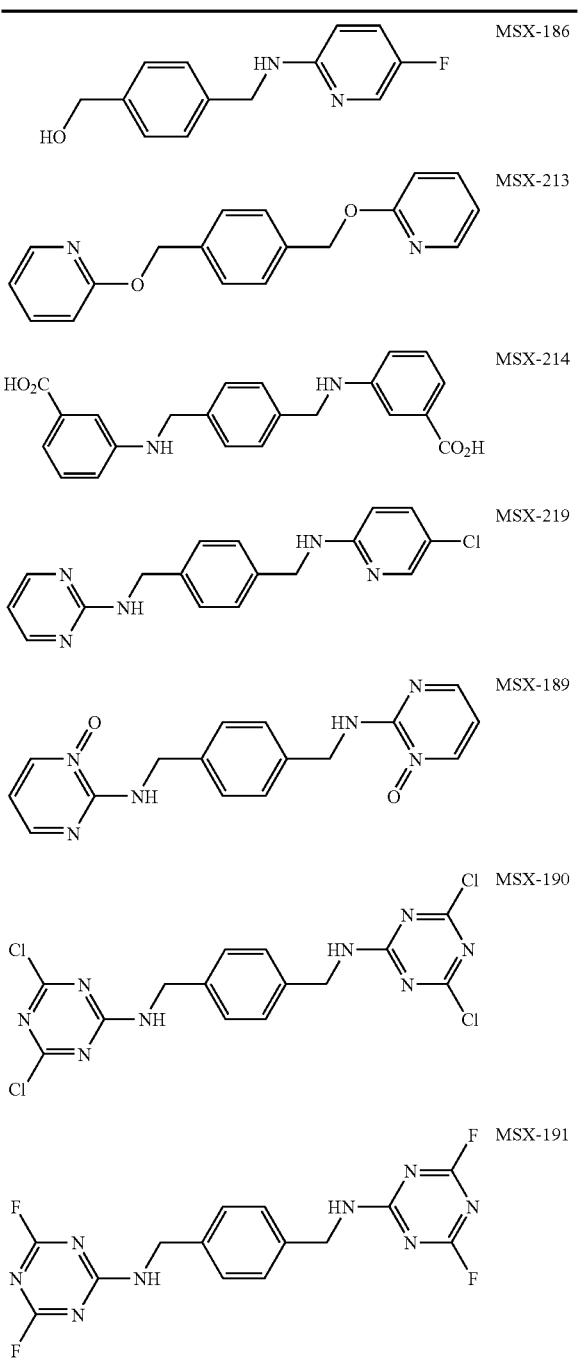
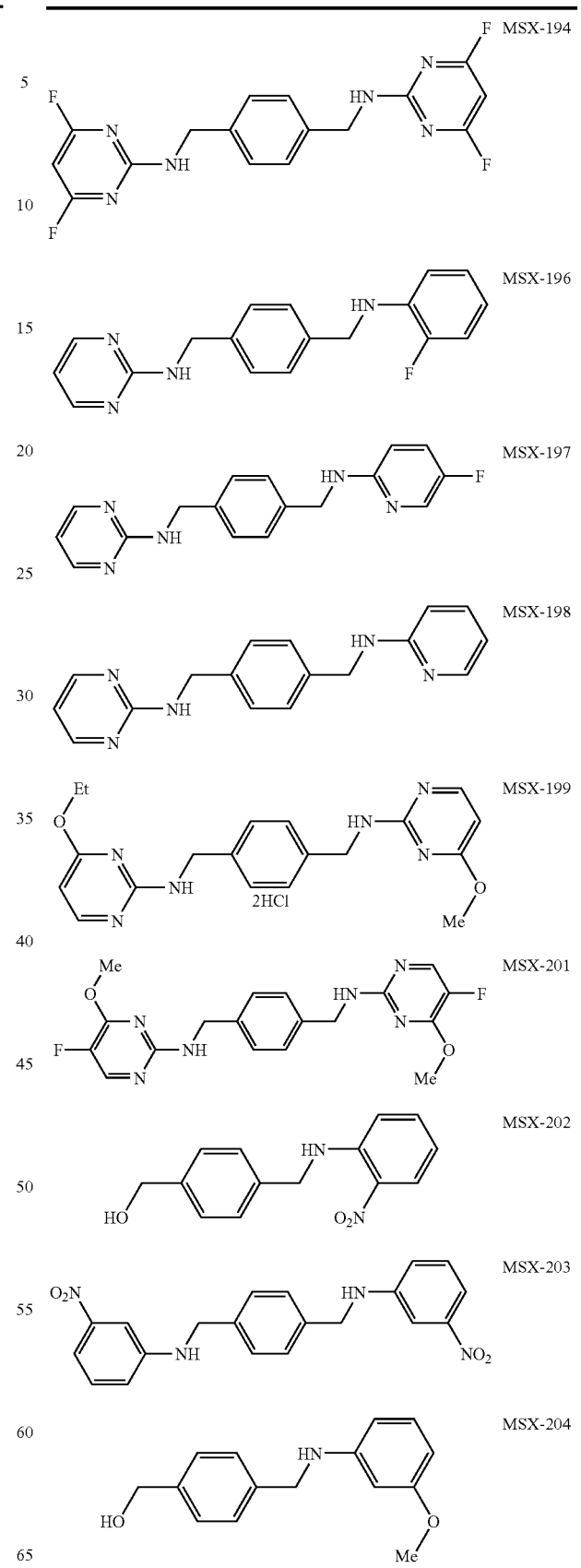

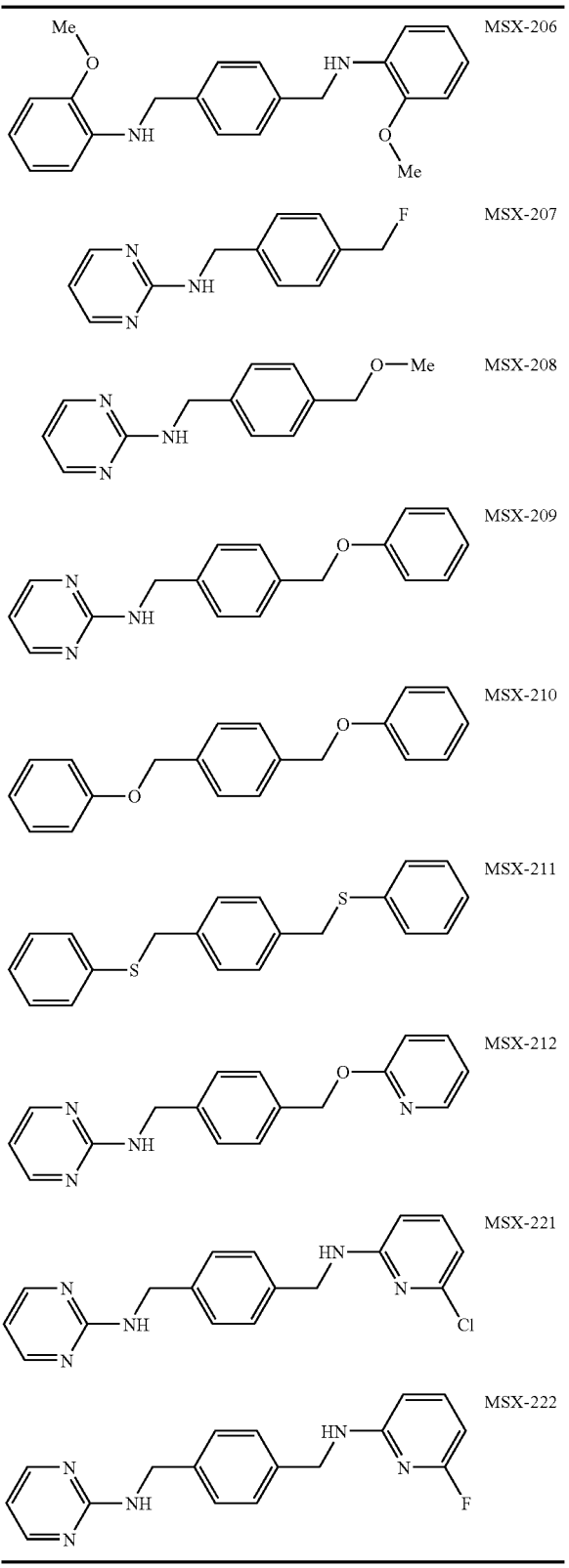

appropriate. Examples of pharmaceutically acceptable salts are organic acid addition salts formed with acids, which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The active compound can also be provided as a prodrug, which is converted into a biologically active form in vivo. A prodrug may be converted into the parent drug by various mechanisms, including enzymatic processes and metabolic hydrolysis. Harper, N. J. (1962) in Jucker, ed. *Progress in Drug Research*, 4:221-294; Morozowich et al. (1977) in E. B. Roche ed. *Design of Biopharmaceutical Properties through Prodrugs and Analogs*, APhA (Acad. Pharm. Sci.); E. B. Roche, ed. (1977) *Bioreversible Carriers in Drug in Drug Design, Theory and Application*, APhA; H. Bundgaard, ed. (1985) *Design of Prodrugs*, Elsevier; Wang et al. (1999) *Curr. Pharm. Design.* 5(4):265-287; Pauletti et al. (1997) *Adv. Drug. Delivery Rev.* 27:235-256; Mizen et al. (1998) *Pharm. Biotech.* 11:345-365; Gaignault et al. (1996) *Pract. Med. Chem.* 671-696; M. Asghamejad (2000) in G. L. Amidon, P. I. Lee and E. M. Topp, Eds., *Transport Proc. Pharm. Sys.*, Marcell Dekker, p. 185-218; Balant et al. (1990) *Eur. J. Drug Metab. Pharmacokinct.*, 15(2): 143-53; Balimane and Sinko (1999) *Adv. Drug Deliv. Rev.*, 39(1-3):183-209; Browne (1997). *Clin. Neuropharm.* 20(1): 1-12; Bundgaard (1979) *Arch. Pharm. Chemi.* 86(1): 1-39; H. Bundgaard, ed. (1985) *Design of Prodrugs*, New York: Elsevier; Fleisher et al. (1996) *Adv. Drug Delivery Rev*, 19(2): 115-130; Fleisher et al. (1985) *Methods Enzymol.* 112: 360-81; Farquhar D, et al. (1983) *J. Pharm. Sci.*, 72(3): 324-325; Han, H. K. et al. (2000) *AAPS Pharm Sci.*, 2(1): E6; Sadzuka Y. (2000) *Curr. Drug Metab.*, 1:31-48; D. M. Lambert (2000) *Eur. J. Pharm. Sci.*, 11 Suppl 2:S1 5-27; Wang, W. et al. (1999) *Curr. Pharm. Des.*, 5(4):265.

The active compound can also be provided as a lipid prodrug. Nonlimiting examples of U.S. patents that disclose suitable lipophilic substituents that can be covalently incorporated into the compound or in lipophilic preparations, include U.S. Pat. No. 5,149,794 (Sep. 22, 1992, Yatvin et al.); U.S. Pat. No. 5,194,654 (Mar. 16, 1993, Hostetler et al., U.S. Pat. No. 5,223,263 (Jun. 29, 1993, Hostetler et al.); U.S. Pat. No. 5,256,641 (Oct. 26, 1993, Yatvin et al.); U.S. Pat. No. 5,411,947 (May 2, 1995, Hostetler et al.); U.S. Pat. No. 5,463,092 (Oct. 31, 1995, Hostetler et al.); U.S. Pat. No. 5,543,389 (Aug. 6, 1996, Yatvin et al.); U.S. Pat. No. 5,543,390 (Aug. 6, 1996, Yatvin et al.); U.S. Pat. No. 5,543,391 (Aug. 6, 1996, Yatvin et al.); and U.S. Pat. No. 5,554,728 (Sep. 10, 1996; Basava et al.).

Method of Treatment

The compounds described herein, are particularly useful for the treatment or prevention of a disorder associated with CXCR4 receptor binding or activation, and particularly for the treatment of HIV or AIDS in a host in need thereof.

In one embodiment, a method of treating or preventing HIV infection or reduction of symptoms associated with AIDS is provided including administering a compound of at least one of Formula (I)-(XVII) to a host. In certain embodiments, the compound can be provided to a host before treat- Formulations In cases where compounds are sufficiently basic or acidic to form stable nontoxic acid or base salts, administration of the compound as a pharmaceutically acceptable salt may be ment of infection with another compound. In a separate embodiment, the compound is provided to a patient that has been treated for HIV infection to reduce the likelihood of recurrence, or reduce mortality associated with AIDS related symptoms. In another embodiment, the compound is administered to a host at high risk of suffering from HIV infections.

Host, including humans suffering from, or at risk for, HIV infection can be treated by administering an effective amount of the active compound or a pharmaceutically acceptable prodrug or salt thereof in the presence of a pharmaceutically acceptable carrier or diluent. The administration can be prophylactically for the prevention of HIV infection or reduction of symptoms associated with AIDS. The active materials can be administered by any appropriate route, for example, orally, parenterally, intravenously, intradermally, subcutaneously, or topically, in liquid or solid form. However, the compounds are particularly suited to oral delivery.

An exemplary dose of the compound will be in the range from about 1 to 50 mg/kg, preferably 1 to 20 mg/kg, of body weight per day, more generally 0.1 to about 100 mg per kilogram body weight of the recipient per day. The effective dosage range of the pharmaceutically acceptable salts and prodrugs can be calculated based on the weight of the parent compound to be delivered. If the salt, ester or prodrug exhibits activity in itself, the effective dosage can be estimated as above using the weight of the salt, ester or prodrug, or by other means known to those skilled in the art.

In one particular embodiment, a method for the treatment or prevention of HIV infection or AIDS is provided including providing an effective amount of a compound of Formula XIII, or a pharmaceutically acceptable salt, ester or prodrug thereof, to a host or cell in need of such treatment:

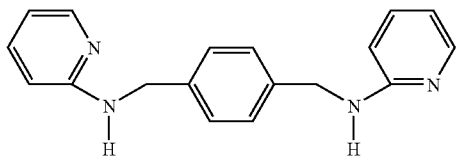

Formula XIII

In a particular subembodiment, the compound is a salt of a compound of Formula XIII, particularly a chloride salt.

In a separate embodiment, a method for the treatment or prevention of HIV infection or reduction of symptoms associated with AIDS by administering a compound of Formulas (I)-(XVII) to a host in need of treatment is provided. The compounds of the invention can be administered to a host in need thereof to reduce the severity of AIDS related disorders. In one embodiment of the invention, the host is a human.

In another embodiment, the invention provides a method of treating symptoms associated with other infections associated with CXCR4 receptor activation, for example, liver diseases associated with flavivirus or pestivirus infection, and in particular, HCV or HBV, by contacting a cell with a compound of Formula (I)-(XVII). The cell can be in a host animal, in particular in a human.

The compounds can treat or prevent HIV infection, or reduce the severity of AIDS related symptoms and diseases in any host. However, typically the host is a mammal and more typically is a human. In certain subembodiments the host has been diagnosed with AIDS prior to administration of the compound, however in other embodiments, the host is merely infected with HIV and asymptomatic.

Pharmaceutical Compositions

In one embodiment, pharmaceutical compositions including at least one compound of Formulas (I)-(XVII) are provided. In certain embodiments, at least a second active compound is administered in combination or alternation with the first compound. The second active compound can be an antiviral, particularly an agent active against a HIV and in a particular embodiment, active against HIV-1.

Host, including humans suffering from, or at risk of contracting, HIV can be treated by administering an effective amount of a pharmaceutical composition of the active compound.

The compound is conveniently administered in unit any suitable dosage form, including but not limited to one containing 7 to 3000 mg, preferably 70 to 1400 mg of active ingredient per unit dosage form. A oral dosage of 50-1000 mg is usually convenient. Ideally the active ingredient should be administered to achieve peak plasma concentrations of the active compound of from about 1 uM to 100 mM or from 0.2 to 700 uM, or about 1.0 to 10 uM.

The concentration of active compound in the drug composition will depend on absorption, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

A preferred mode of administration of the active compound is oral. Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

The compound can be administered as a component of an elixir, suspension, syrup, wafer, chewing gum or the like. A syrup may contain, in addition to the active compounds, sucrose as a sweetening agent and certain preservatives, dyes and colorings and flavors.

The compound or a pharmaceutically acceptable prodrug or salts thereof can also be mixed with other active materials that do not impair the desired action, or with materials that supplement the desired action, such as antibiotics, antifungals, anti-inflammatories, or antiviral compounds, or with additional chemotherapeutic agents. Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

In a preferred embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters and polylactic acid. Methods for preparation of such formulations will be apparent to those skilled in the art. The materials can also be obtained commercially from Alza Corporation. If administered intravenously, preferred carriers are physiological saline or phosphate buffered saline (PBS).

Liposomal suspensions (including liposomes targeted to infected cells with monoclonal antibodies to viral antigens) are also preferred as pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound or its monophosphate, diphosphate, and/or triphosphate derivatives is then introduced into the container. The container is then swirled by hand to free lipid material from the sides of the container and to disperse lipid aggregates, thereby forming the liposomal suspension.

Combination and Alternation Therapy

In one embodiment, the compounds described herein are administered in combination or alternation with another active compound.

In one embodiment, the second active compound is a compound that is used as an anti-HIV agent, including but not limited to a nucleoside or nonnucleoside reverse transcriptase inhibitor, a protease inhibitor, a fusion inhibitor, cytokine and interferon. The compound provided in combination or alternation can, as a nonlimiting example, be selected from the following lists:

| Brand Name | Generic Name |
| --- | --- |
| Agenerase | amprenavir |
| Combivir | lamivudine and zidovudine |
| Crixivan | indinavir, IDV, MK-639 |
| Emtriva | FTC, emtricitabine |
| Epivir | lamivudine, 3TC |
| Epzicom | abacavir/lamivudine |
| Fortovase | saquinavir |
| Fuzeon | enfuvirtide, T-20 |

-continued

| Brand Name | Generic Name |
| --- | --- |
| Hivid | zalcitabine, ddC, dideoxycytidine |
| Invirase | saquinavir mesylate, SQV |
| Kaletra | lopinavir and ritonavir |
| Lexiva | Fosamprenavir Calcium |
| Norvir | ritonavir, ABT-538 |
| Rescriptor | delavirdine, DLV |
| Retrovir | zidovudine, AZT, azidothymidine, ZDV |
| Reyataz | atazanavir sulfate |
| Sustiva | efavirenz |
| Trizivir | abacavir, zidovudine, and lamivudine |
| Truvada | tenofovir disoproxil/emtricitabine |
| Videx EC | enteric coated didanosine |
| Videx | didanosine, ddI, dideoxyinosine |
| Viracept | nelfinavir mesylate, NFV |
| Viramune | nevirapine, BI-RG-587 |
| Viread | tenofovir disoproxil fumarate |
| Zerit | stavudine, d4T |
| Ziagen | abacavir |

Further active agents include: GW5634 (GSK), (+)Calanolide A (Sarawak Med.), Capravirine (Agouron), MIV-150 (Medivir/Chiron), TMC125 (Tibotec), RO033-4649 (Roche), TMC114 (Tibotec), Tipranavir (B-I), GW640385 (GSK/Vertex), Elvucitabine (Achillion Ph.), Alovudine (FLT) (B-I), MIV-210 (GSK/Medivir), Racivir (Pharmasset), SPD754 (Shire Pharm.), Reverset (Incyte Corp.), FP21399 (Fuji Pharm.), AMD070 (AnorMed), GW873140 (GSK), BMS-488043 (BMS), Schering C/D (417690), PRO 542 (Progenics Pharm), TAK-220 (Takeda), TNX-355 (Tanox), UK-427,857 (Pfizer).

Further active agents include: Attachment and Fusion Inhibitors (i.e. AMD070, BMS-488043, FP21399, GW873140, PRO 542, Schering C, SCH 417690, TAK-220, TNX-355 and UK-427,857); Integrase Inhibitors; Maturation Inhibitors (i.e. PA457); Zinc Finger Inhibitors (i.e. azodicarbonamide (ADA)); Antisense Drugs (i.e. HGTV43 by Enzo Therapeutics, GEM92 by Hybridon); Immune Stimulators (i.e. Ampligen by Hemispherx Biopharma, IL-2 (Proleukin) by Chiron Corporation, Bay 50-4798 by Bayer Corporation, Multikine by Cel-Sci Corporation, IR103 combo); Vaccine-Like Treatment (i.e. HRG214 by Virionyx, DermaVir, VIR201 (Phase I/IIa)).

In one embodiment, the compounds of the invention are administered in combination with another active agent. The compounds can also be administered concurrently with the other active agent. In this case, the compounds can be administered in the same formulation or in a separate formulation. There is no requirement that the compounds be administered in the same manner. For example, the second active agent can be administered via intravenous injection while the compounds of the invention may be administered orally. In another embodiment, the compounds of the invention are administered in alternation with at least one other active compound. In a separate embodiment, the compounds of the invention are administered during treatment with an active agent, such as, for example, an agent listed above, and administration of the compounds of the invention is continued after cessation of administration of the other active compound.

The compounds of the invention can be administered prior to or after cessation of administration of another active compound. In certain cases, the compounds may be administered before beginning a course of treatment for viral infection or for secondary disease associated with HIV infections, for example. In a separate embodiment, the compounds can be administered after a course of treatment to reduce recurrence of viral infections.

Diseases

The compounds described herein, are particularly useful for the treatment or prevention of a disorder associated with CXCR4 receptor binding or activation, and particularly HIV viral infections. However, numerous other diseases have been associated with CXCR4 receptor signaling.

Human and simian immunodeficiency viruses (HIV and SIV, respectively) enter cells through a fusion reaction triggered by the viral envelope glycoprotein (Env) and two cellular molecules: CD4 and a chemokine receptor, generally either CCR5 or CXCR5. (Alkhatib G, Combadiere C, Croder C, Feng Y, Kennedy P E, Murphy P M, Berger E A. CC CKR5. a RANTES, MIP-1apha, MIP-1Beta receptor as a fusion cofactor for macrophage-tropic HIV-1. *Science*. 1996; 272: 1955-1988).

In approximately 50% of infected individuals, CXCR4-tropic (X4-tropic) viruses emerge later in HIV infection, and their appearance correlates with a more rapid CD4 decline and a faster progression to AIDS (Connor, et al. (1997) *J Exp. Med.* 185: 621-628). Dual-tropic isolates that are able to use both CCR5 and CXCR4 are also seen and may represent intermediates in the switch from CCR5 to CXCR4 tropism (Doranz, et al. (1996) *Cell*. 85: 1149-1158).

In a separate embodiment, a method for the treatment of, prevention of, or reduced severity of liver disease associated with viral infections including administering at least one compound described herein is provided.

Chronic hepatitis C virus (HCV) and hepatitis B virus (HBC) infection is accompanied by inflammation and fibrosis eventually leading to cirrhosis. A study testing the expression and function of CXCR4 on liver-infiltrating lymphocytes (LIL) revealed an important role for the CXCL12/CXCR4 pathway in recruitment and retention of immune cells in the liver during chronic HCV and HBV infection (Wald, et al. (2004) *European Journal of Immunology*. 34(4): 1164-1174).

High levels of CXCR4 and TGF-β have been detected in liver samples obtained from patients infected with HCV. (Mitra, et al. (1999) *Int. J. Oncol.* 14: 917-925). In vitro, TGF-β has been shown to up-regulate the expression of CXCR4 on naïve T cells and to increase their migration. The CD69/TGF-β/CXCR4 pathway may be involved in the retention of recently activated lymphocytes in the liver (Wald, et al. *European Journal of Immunology*. 2004; 34(4): 1164-1174).

EXAMPLES

Example 1

Peptide-Based CXCR4 Antagonist, TN14003, is a Novel-Imaging Probe Specific for CXCR4

Initially, experiments were performed to verify that TN14003 binds to the predicted SDF-1 binding sites on the CXCR4 receptor. In these studies, MDA-MB-231 cells were incubated in the absence (FIG. 1A, B) or presence (FIG. 1A, C) of 400 ng/ml of SDF-1α for 10 min, and then fixed in ice-cold acetone. Immunofluorescence of the biotin-labeled TN14003 was negative in both membrane and cytosol in the cells pretreated with SDF-1α for 10 min (FIG. 1A, C).

The utility of the biotinylated TN14003 as a probe of CXCR4 was explored coupled with immunofluorescence staining of cultured breast cancer cells and paraffin-embedded tissues from breast cancer patients. MDA-MB-231 had high levels of mRNA and protein for CXCR4 as shown by Northern blots and Western blots relative to MDA-MB-435 (FIG. 1B). When the biotinylated TN14003 was used to stain the two cell types, the high CXCR4-expressing MDA-MD-231 cells were brightly stained (FIG. 1C left), whereas the low CXCR4-expressing MDA-MB-435 was less (FIG. 1C right) consistent with the low surface CXCR4 expression in these cells.

Immunofluorescence staining with the biotinylated TN14003 on cancer patients' paraffin-embedded tissue sections demonstrated that TN14003 could be used to detect CXCR4 receptors on tumor cells from the archived paraffin-embedded tissue sections (FIG. 1D). A total of 41 patient tissues provided by Avon Tissue Bank for Translational Genomics Research at Grady Memorial Hospital in Atlanta, Ga., were stained and 0 out of 4 normal breast tissues, 9 out of 12 Ductal Carcinoma in situ (DCIS), and 23 out of 25 node-positive cases were positive for CXCR4. Many samples carrying the diagnoses of DCIS already acquired CXCR4 over-expression (FIG. 1D).

Example 2

TN14003 is a More Potent Inhibitor of CXCR4-Associated Signaling than AMD3100

Figure 2:
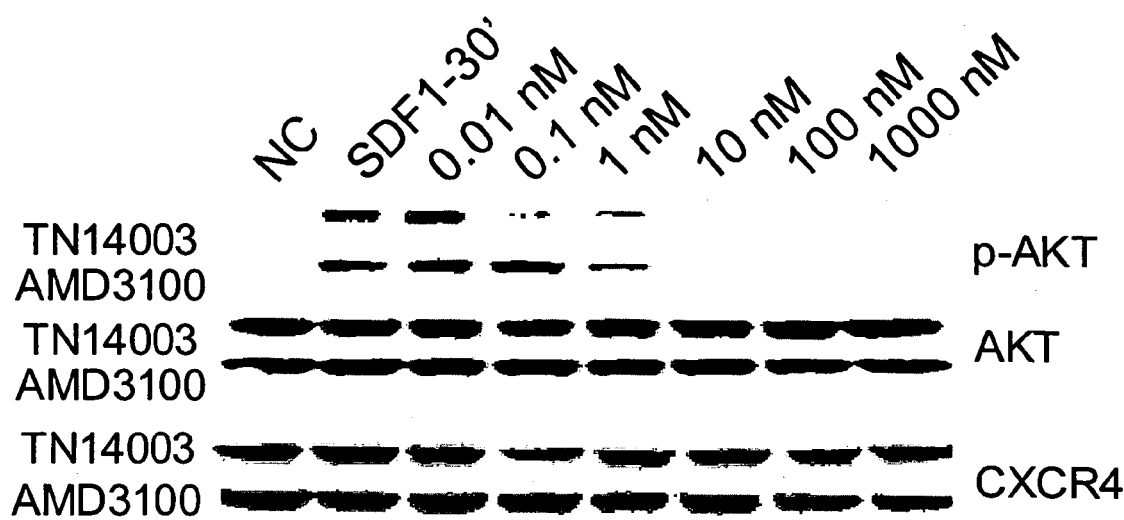
FIG. 2 is an image of a western blot showing phosphorylation of Akt. Incubating MDA-MB-231 cells with 100 ng/ml of SDF-1 for 30 min stimulated phosphorylation of Akt. This activation was blocked with TN14003 or AMD3100 in a dose-dependent manner.

CXCR4/SDF-1 interaction activates PI3K/Akt and Ras/Raf/MEK/Erk pathways in a Gαs protein (PTX-sensitive)-dependent manner. Experiments were conducted to determine the effect of blocking CXCR4/SDF-1 interaction by either TN14003 or AMD3100 at different concentrations (0, 0.01, 0.1, 1, 10, 100, 1000 nM) on phosphorylations of Akt and Erk1/2 signaling. Incubating cells with 100 ng/ml of SDF-1 for 30 minutes activated Akt. Akt activation was blocked by either sub-nano molar concentration of TN14003 or a few nano molar AMD3100 (FIG. 2). Erk1/2 phsophorylation was attenuated in the presence of sub-nano molar concentration of TN14003 or 100 nM AMD3100 (data not shown). However, the increase in Erk1/2 phosphorylation by SDF-1 was not significant as the increase in Akt phosphorylation. The results demonstrate that TN14003 is more potent than AMD3100 in inhibiting CXCR4-mediated signaling. Treating cells with SDF-1, TN14003, or AMD3100 did not affect CXCR4 protein levels.

Example 3

VEGF Promotor Regulation by CXCR4 and HIF-1α

Figure 3:
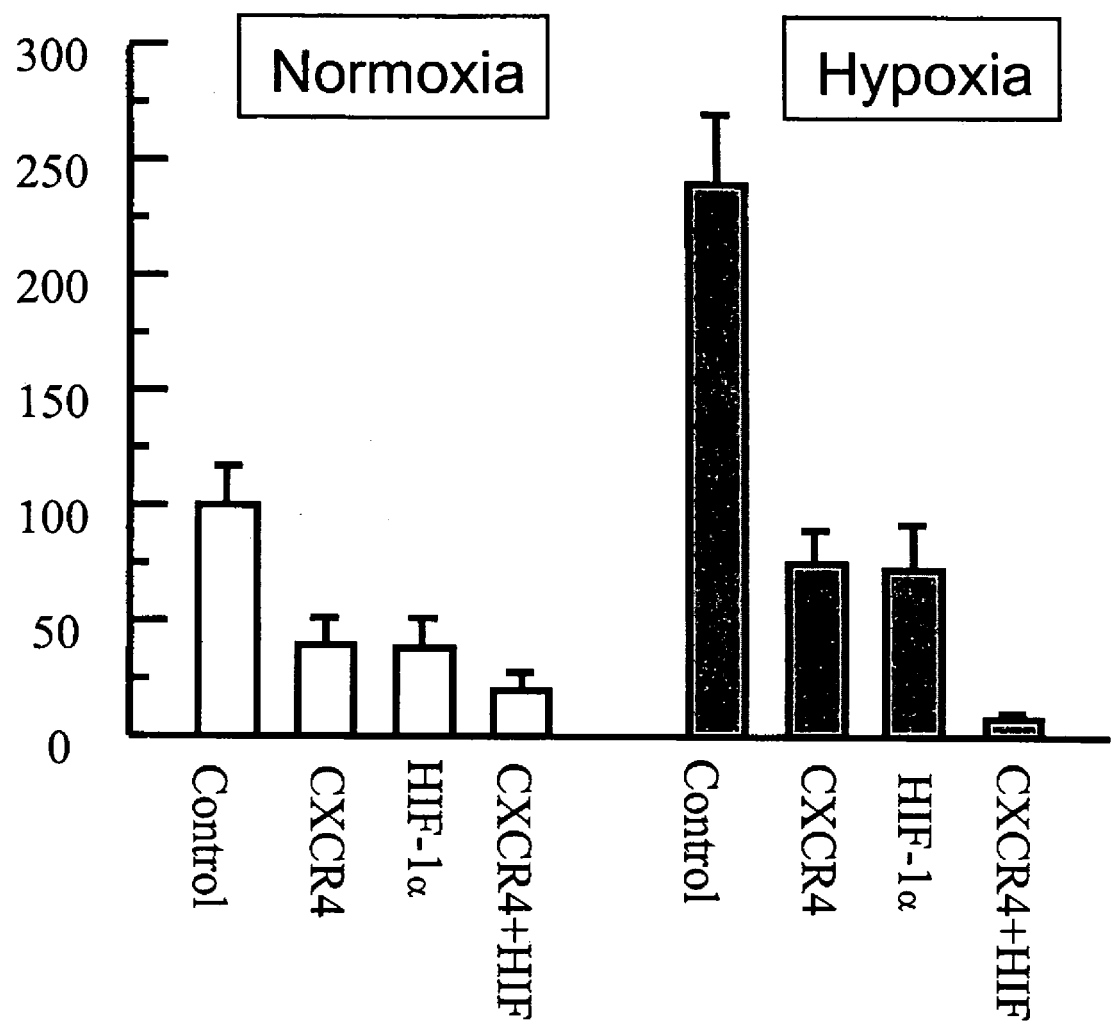
FIG. 3 is a graph of HRE activity. The graph shows that HRE-Luc MB-231 cells have moderately high HRE activity in normoxia that can be suppressed by either CXCR4 siRNA or HIF-1 siRNA. HRE acitivity increase 2.5 fold in hypoxia that can also be suppressed by either CXCR4 siRNA or HIF-1 siRNA.

To determine whether lowering CXCR4 levels might affect VEGF transcription compared to HIF-1α the hypoxia-reporting luciferase/LacZ plasmid from Dr. Van Meir's laboratory was used as a reporter system to detect hypoxia-responsive element (HRE) of VEGF promoter activity (Post, D. E. and Van Meir, E. G. (2001) *Gene Ther* 8: 1801-1807). The sequence of HIF-1α siRNA was 5'-UUCAAGUUGGAA-UUGGUAGdTdT-3'(SEQ ID NO: 1). Pooled cell clones were created with MDA-MB-231 cells stably transfected with this plasmid (called HRE-Luc MB-231). Unexpectedly, HRE activity in normoxia was moderately high in MDA-MB-231 cells that have high CXCR4 levels in normoxia (FIG. 3, left), which was not observed in other cell lines with low CXCR4 and HIF-1 levels (LN229, U87, 9L, and MDA-MB-435). This moderately high HRE activity in MDA-MB-231 cells was suppressed by CXCR4 siRNA or HIF-1α siRNA. The HRE activity significantly decreased with the combination treatment of CXCR4 siRNA and HIF-1α siRNA for 48 hours. As expected, the HRE activity increased 2.5-fold by hypoxia treatment (1% oxygen and 5% $CO_2$ in nitrogen). This elevated HRE activity was again suppressed by siRNA for CXCR4 or HIF-1α (FIG. 3, right).

Example 4

Screening of Novel Anti-CXCR4 Small Molecule by Competition Assay Using Biotin-Labeled TN14003 (Peptide-Based)

The molecular dynamic simulations of the rhodopsin-based homology model of CXCR4 shows that AMD3100 is a weak partial agonist because it interacts with CXCR4/SDF-1 binding by two aspartic acids while the peptide-based CXCR4 antagonist, T140 (similar to TN14003) strongly binds the SDF-1 binding site of CXCR4 in extracellular domains and regions of the hydrophobic core proximal to the cell surface (Trent, et al. (2003) *J Biol Chem* 278: 47136-47144). This structural information was used to create a library of compounds with multiple nitrogens throughout the molecular framework, but structurally different from AMD3100.

Figure 4:
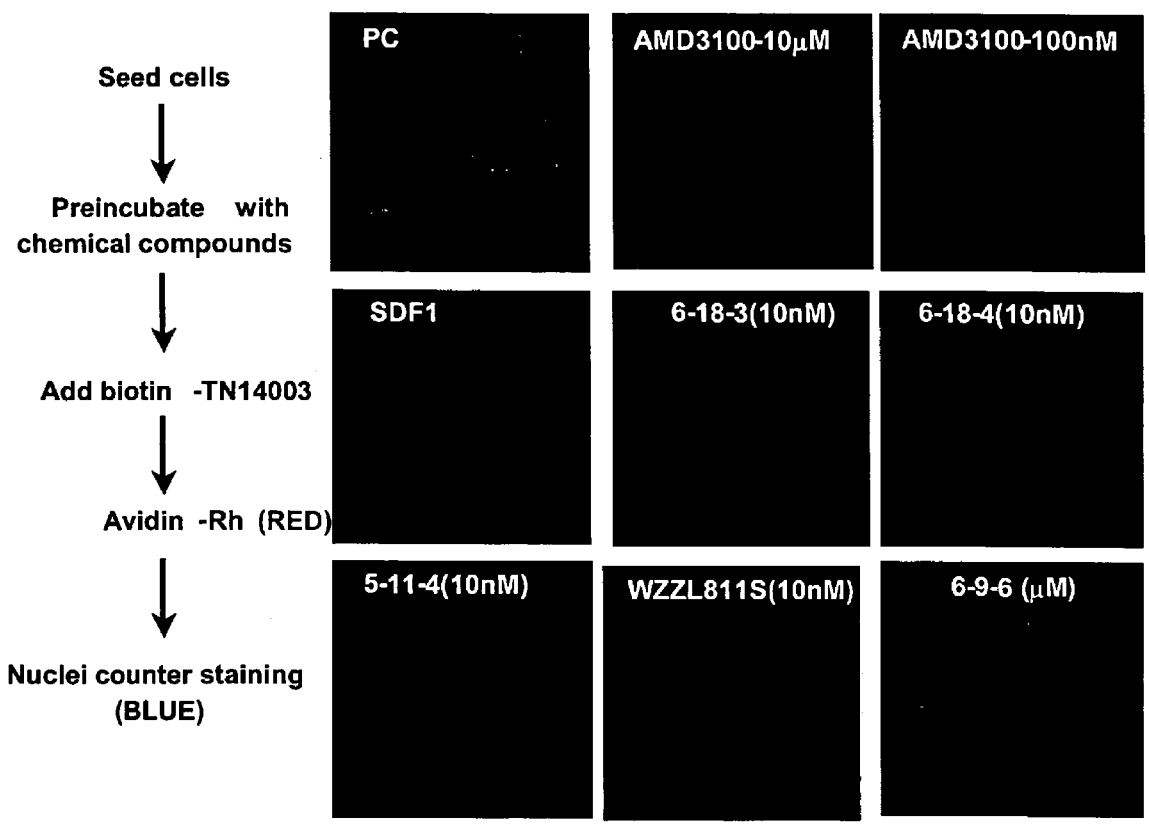
FIG. 4 shows images of a drug screen methodology utilizing biotin-labeled TN14003 as a reporter.
Figure 5:
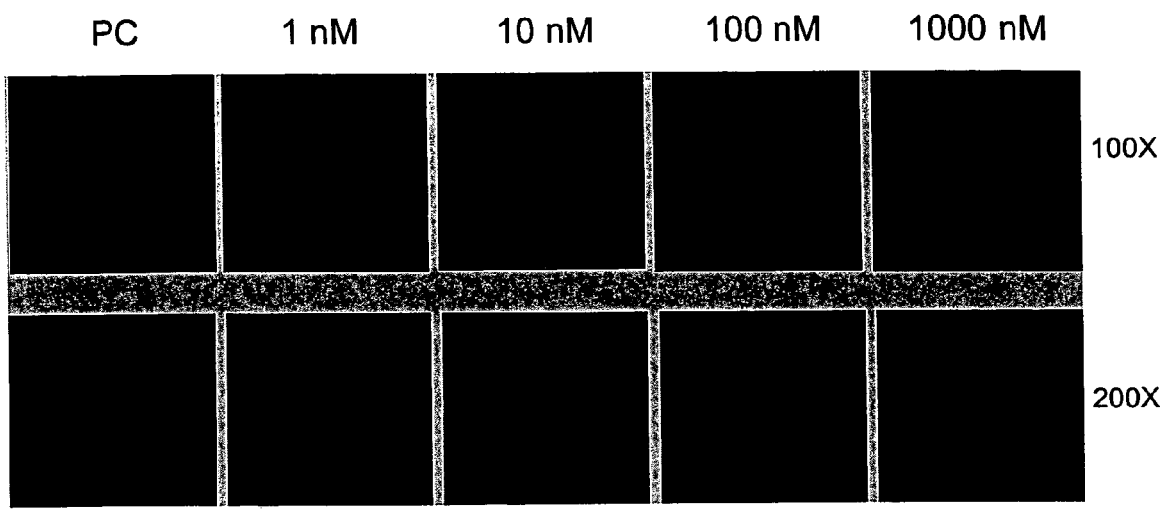
FIG. 5 shows images of stained cells. Biotin-labeled TN14003 was used to detect CXCR4 protein from the cells pre-incubated with various concentrations of WZZL811S. Results indicate that IC50 of WZZL811S is less than 1 nM.
Figure 6:
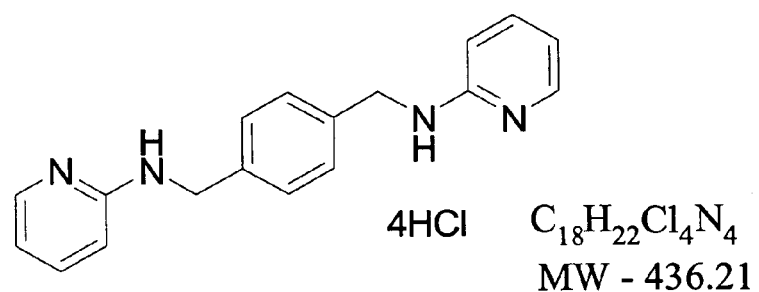
FIG. 6 shows the chemical structure of WZZL811S.

Using biotin-labeled TN14003 along with streptavidin-conjugated rhodamine allowed a determination of the binding efficiency of these chemicals to the SDF-1 binding site of CXCR4 on tumor cells and compared it to AMD3100-SDF-1 interactions (FIG. 4). The cells incubated with compounds with high affinities for the ligand-binding site showed only blue nuclei staining, whereas compounds with low affinity resulted in both CXCR4 in red (rhodamine) and blue nuclei staining. Cells were pre-incubated with different concentrations of AMD3100. The results indicated that 10 µM concentration was needed for AMD3100 to compete against biotin-labeled TN14003. On the other hand, some candidate compounds were as potent as TN14003 at very low concentrations. Therefore, one of these compounds, WZZL811S, was selected to study its therapeutic potential based on potency and low toxicity to cells (FIG. 6). FIG. 5 shows the binding affinity of WZZL811S to the ligand-binding site (approximately the same as TN14003 binding site) of CXCR4 on tumor cells at nano-molar concentration. WZZL811S did not decrease cell viability of MDA-MB-231 cells even at 100 µM (the highest concentration tested).

Example 5

Pharmacokinetics of a Novel Anti-HIF1α Compound

Figure 7:
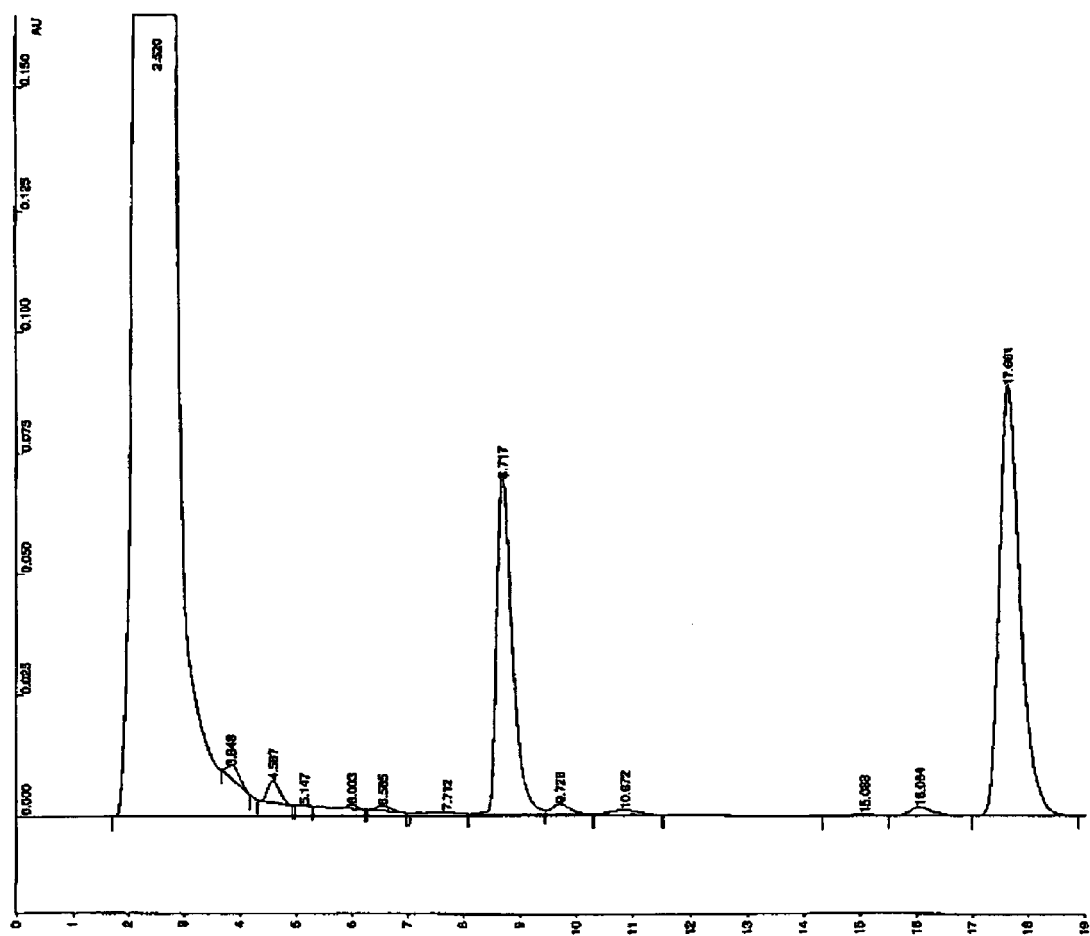
FIG. 7 shows a graph of the HPLC analysis performed as described in Example 8.

A pharmacokinetic study of a novel anti-HIF-1α small molecule was performed. A stably integrated hypoxia-reporter system of glioma cells transfected with the hypoxia-reporting plasmid (described above) was utilized. A natural product-like small molecule library of 10,000 compounds was screened and the "best hit" was identified. HPLC methodology was developed for quantitatively detecting KCN-1 in plasma and other biological samples. For the pharmacokinetic study, KCN-1 (100 mg/kg) was dissolved in DMSO and administered intravenously to mice. Plasma samples were collected at given time points (0.25, 0.5, 1, 2, 4 and 8 h) and KCN-1 levels were quantified by HPLC. The HPLC system consisted of a Varian Prostar gradient pump, a Prostar autosampler and a Prostar photo diode array detector. The column was a Luna 5µ C18 column (4.6 mm×250 mm, Phenomenex). The retention time of KCN1 and the internal standard were 8.7 and 17.7 min, respectively (FIG. 7).

Example 6

Test Compound Activity Against HIV Strains

A selected set of compounds were tested for their ability to inhibit the cellular entry of T-tropic HIV. The assay for this inhibition has been carried out on a contractural basis at Monogram Biosciences, Inc. using their well established Phenoscreen™ assay. Briefly, HIV strains of interest are tagged with a luciferase indicator gene to create an appropriate test vector. The test vector is amplified through transfection and the resulting virus is incubated in the presence of target host cells where intracellular florescence activity then becomes a measure of infection. Amplified virus is exposed to target host cells in the presence of a range of test drug concentrations to determine $IC_{50}$ measurements of entry inhibition. A modification of this test has been further reapplied as a novel drug assay that has been used in partnership with a number of pharmaceutical companies to test the effectiveness of novel entry inhibitors that target specific chemokines. It can used to detect activity against T-tropic, M-tropic, and dual-tropic viruses and Monogram Biosciences has a large bank of over 10,000 different virus strains to ultimately asses the range of applicability of our CXCR4 antagonists. Certain compounds have been tested to establish efficacy in a number of viral strains. Results are shown in Table 2 below.

TABLE 2

| Compound | Viral Entry Inhibition (µM) | | | | | | |
|---|---|---|---|---|---|---|---|
| | HXB2 | NL4-3 | Vrs-1 | Vrs-2 | Vrs-3 | Dual | SHIV |
| TN-14003 | 0.010 | 0.005 | 0.010 | NA | 0.025 | 0.025 | 0.007 |
| AMD-3100 | 0.013 | 0.008 | 0.013 | 0.015 | 0.043 | 0.030 | 0.013 |
| WZ-811-S | >15 | >15 | >15 | ~12 | >15 | >15 | >15 |

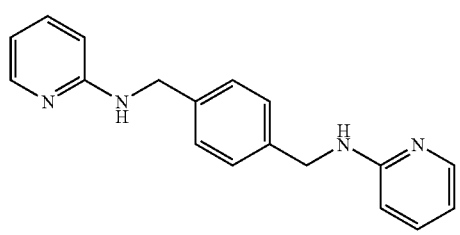

TABLE 2-continued
| Compound | | Viral Entry Inhibition (μM) | | | | | | |
|---|---|---|---|---|---|---|---|---|
| | | HXB2 | NL4-3 | Vrs-1 | Vrs-2 | Vrs-3 | Dual | SHIV |
| 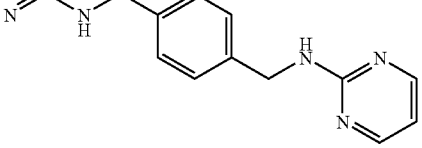 | WZ-40-MS | >15 | >15 | >15 | ~10 | >15 | >15 | ~12 |
| 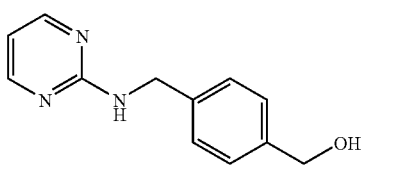 | WZ-41 | >15 | >15 | >15 | ~13 | >15 | >15 | ~15 |
| 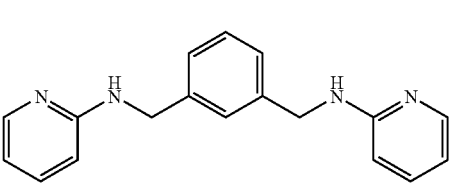 | WZ-48-S | >15 | >15 | >15 | ~11 | >15 | >15 | ~11 |
|  | WZ-81810 | >15 | >15 | >15 | ~10 | >15 | >15 | ~12 |
| 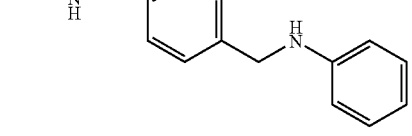 | WZ-814-S | ~15 | ~11 | ~11 | ~11 | ~11 | >15 | >15 |
| 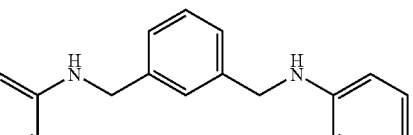 | WZ-8224 | 8.08 | 6.37 | 4.78 | 4.31 | 5.72 | 6.25 | 1.70 |
| 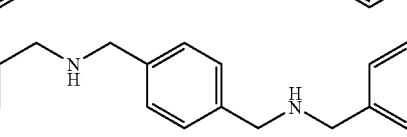 | WZ-8225 | ~11 | ~10 | ~11 | ~10 | ~10 | >15 | ~10 |
| 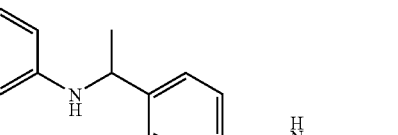 | WZ-9103 | ~13 | ~11 | >15 | ~15 | ~15 | >15 | 9.50 |

TABLE 2-continued
| Compound | | Viral Entry Inhibition (μM) | | | | | | |
|---|---|---|---|---|---|---|---|---|
| | | HXB2 | NL4-3 | Vrs-1 | Vrs-2 | Vrs-3 | Dual | SHIV |
| 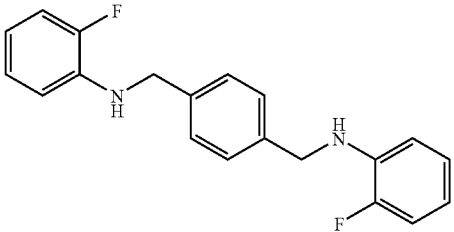 | WZ-51 | >15 | ~12 | ~10 | ~10 | ~10 | ~12 | 1.42 |
| 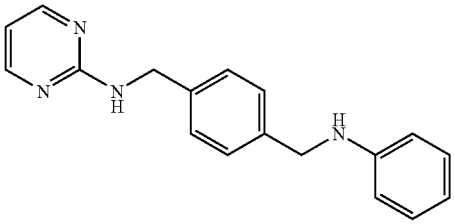 | WZ-67 | >15 | ~11 | >15 | ~11 | ~12 | >15 | ~10 |
| 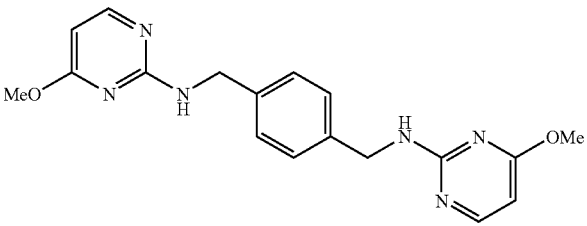 | WZ-72-S | >15 | ~15 | >15 | ~12 | >15 | >15 | 4.44 |
| 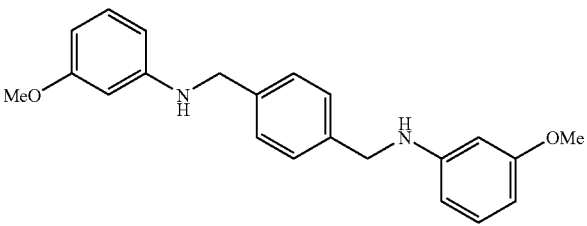 | WZ-77 | >15 | ~14 | >15 | ~11 | >15 | >15 | 8.96 |
In a competition screening using the native CXCR4 ligand SDF-1, the compounds showed the following interactions:
| Compound | IC$_{50}$ (nM) vs SDF-1 | t$_{1/2}$ (min) in mice |
|---|---|---|
| 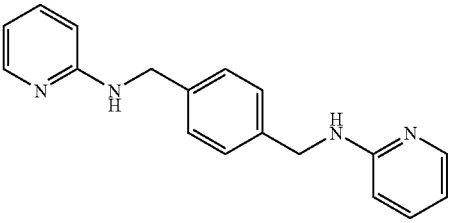 | <10 | |

-continued
| Compound | IC$_{50}$ (nM) vs SDF-1 | t$_{1/2}$ (min) in mice |
|---|---|---|
| 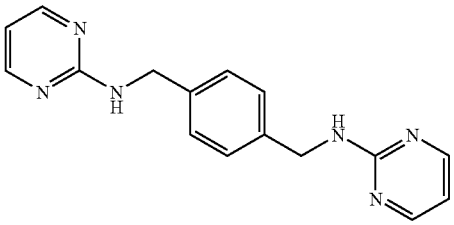 | <10 | 45 |
| 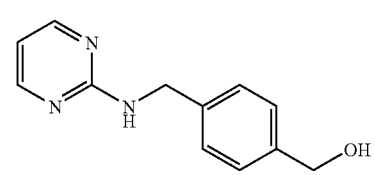 | <10 | |
| 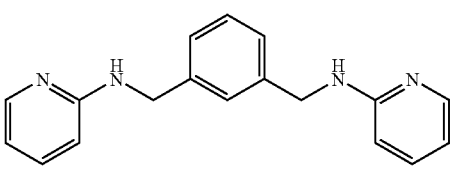 | <10 | |
| 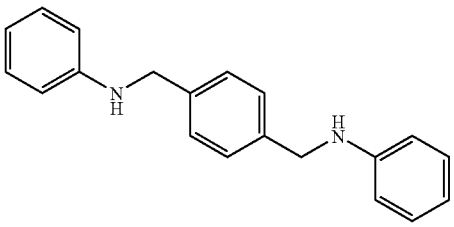 | <10 | 11 |
| 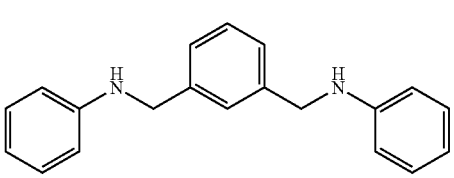 | <10 | <5 |
| 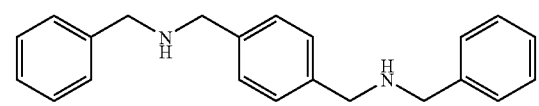 | <100 | |
| 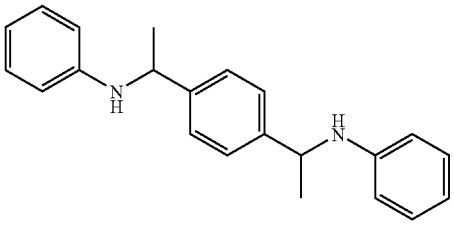 | <100 | 13.7 |
| 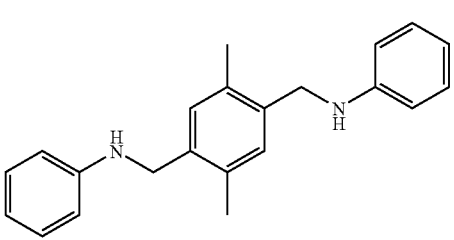 | >100 | |

| Compound | IC$_{50}$ (nM) vs SDF-1 | t$_{1/2}$ (min) in mice |
|---|---|---|
| 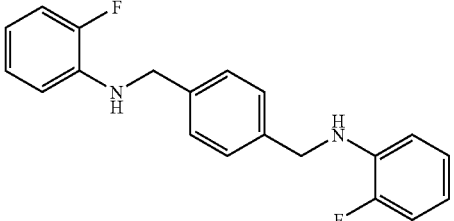 | <10 | |
| 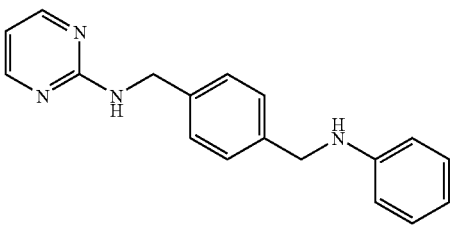 | 10 | 14 |
| 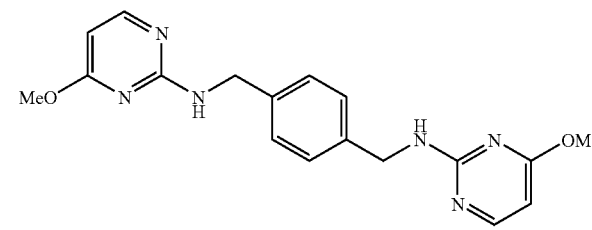 | 10 | |
| 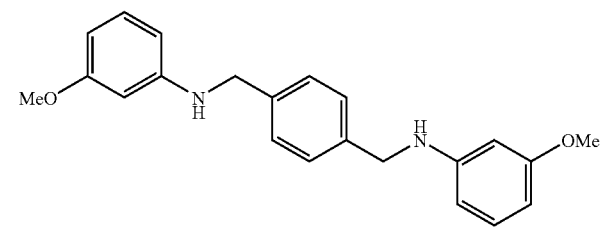 | 1 | 14.3 |

We claim:

1. A compound of Formula I, or a pharmaceutically acceptable salt or ester thereof:

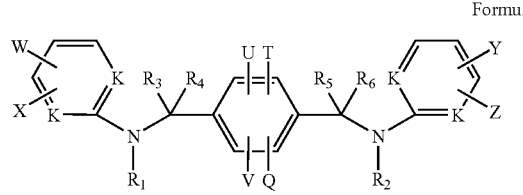

Formula I each K is independently N;

Each Q, T, U, V, W, X, Y and Z are each independently H, R, acyl, F, Cl, Br, I, CN, OH, OR, $NH_2$, $NO_2$, NHR, $NR_2$, SR, $S_2R$, S—NHR, $S_2$—NHR, S—NRR', $S_2$—NRR', NHacyl, $N(acyl)_2$, $CO_2H$, $CO_2R$, where R and R' are independently selected from straight chain, branched or cyclic alkyl or aralkyl, as well as aryl and heteroaryl groups;

$R^1$ and $R^2$ are hydrogen;

$R^3$, $R^4$, $R^5$ and $R^6$ are independently selected from H, straight chain, branched or cyclic alkyl, aralkyl, aryl heteroaryl, acyl and imidolyl groups.

2. The compound of claim 1 wherein the compound is selected from the group consisting of a compound of Formula I-15, I-16, I-19 and I-20, or a pharmaceutically acceptable salt or ester thereof:

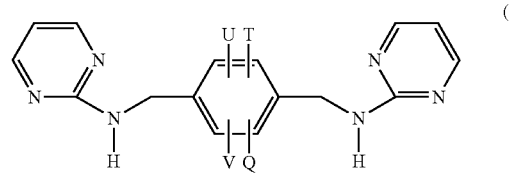
(I-15)

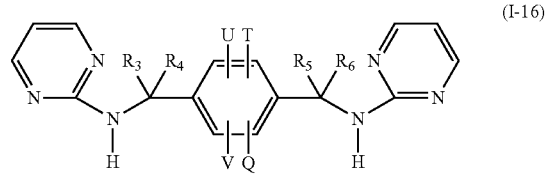
(I-16)

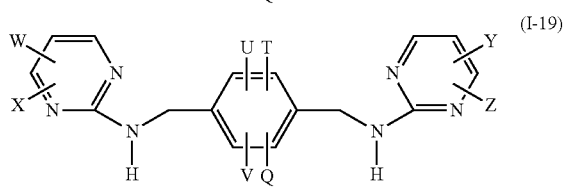
(I-19)

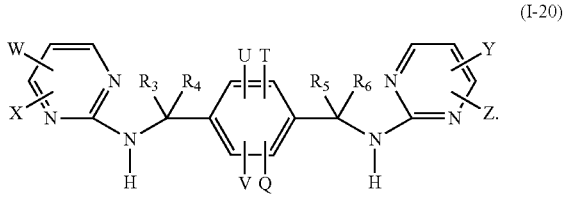
(I-20)

3. A compound of structure XVI, or a pharmaceutically acceptable salt thereof:

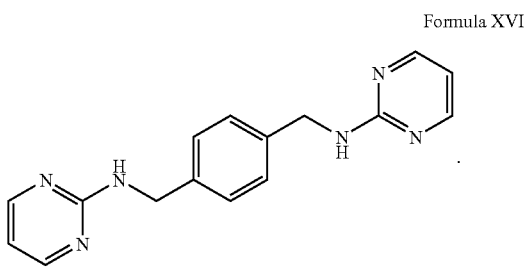

Formula XVI

* * * * *

SEQUENCE LISTING

<160> NUMBER OF SEQ ID NOS: 1

<210> SEQ ID NO 1
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: this is a combined DNA/RNA sequence
<220> FEATURE:
<221> NAME/KEY: misc_feature
<222> LOCATION: (20)..(21)
<223> OTHER INFORMATION: n=deoxythymidine

<400> SEQUENCE: 1
uucaaguugg aauugguagn n                    21